(12) United States Patent
Basi et al.

(10) Patent No.: US 7,871,615 B2
(45) Date of Patent: Jan. 18, 2011

(54) HUMANIZED ANTIBODIES THAT RECOGNIZE BETA AMYLOID PEPTIDE

(75) Inventors: Guriq Basi, Palo Alto, CA (US); Jose Saldanha, Enfield (GB); Frédérique Bard, Pacifica, CA (US)

(73) Assignees: Janssen Alzheimer Immunotherapy, Little Island Industrial Estate, Little Island, County Cork (IE); Wyeth LLC, Five Giralda Farms, Madison, NJ (US)

( * ) Notice: Subject to any disclaimer, the term of this patent is extended or adjusted under 35 U.S.C. 154(b) by 15 days.

(21) Appl. No.: 10/858,855

(22) Filed: Jun. 1, 2004

(65) Prior Publication Data

US 2005/0118651 A1 Jun. 2, 2005

Related U.S. Application Data

(60) Provisional application No. 60/474,654, filed on May 30, 2003.

(51) Int. Cl.
- C07K 16/44 (2006.01)
- C07H 21/00 (2006.01)
- G01N 33/53 (2006.01)
- C12P 21/04 (2006.01)

(52) U.S. Cl. ............... 424/133.1; 530/388.15
(58) Field of Classification Search ............. 424/133.1; 530/388.15
See application file for complete search history.

(56) References Cited

U.S. PATENT DOCUMENTS

| | | | |
|---|---|---|---|
| 4,666,829 A | 5/1987 | Glenner et al. | |
| 4,713,366 A | 12/1987 | Stevens | |
| 4,816,397 A | 3/1989 | Boss et al. | |
| 4,816,567 A | 3/1989 | Cabilly et al. | |
| 4,879,213 A | 11/1989 | Fox et al. | |
| 4,912,206 A | 3/1990 | Goldgaber et al. | |
| 5,004,697 A | 4/1991 | Pardridge | |
| 5,057,540 A | 10/1991 | Kensil et al. | |
| 5,096,706 A | 3/1992 | Flint | |
| 5,187,153 A | 2/1993 | Cordell et al. | |
| 5,192,753 A | 3/1993 | McGeer et al. | |
| 5,208,036 A | 5/1993 | Eppstein et al. | |
| 5,220,013 A | 6/1993 | Ponte et al. | |
| 5,225,539 A | 7/1993 | Winter | |
| 5,227,159 A | 7/1993 | Miller | |
| 5,231,000 A | 7/1993 | Majocha et al. | |
| 5,231,170 A | 7/1993 | Averback | |
| 5,245,015 A | 9/1993 | Fung et al. | |
| 5,258,498 A | 11/1993 | Huston et al. | |
| 5,262,332 A | 11/1993 | Selkoe | |
| 5,270,165 A | 12/1993 | Van Nostrand et al. | |
| 5,278,049 A | 1/1994 | Baker et al. | |
| 5,358,708 A | 10/1994 | Patel | |
| 5,385,887 A | 1/1995 | Yim et al. | |
| 5,387,742 A | 2/1995 | Cordell | |
| 5,434,170 A | 7/1995 | Andrulis, Jr. | |
| 5,441,870 A | 8/1995 | Seubert et al. | |
| 5,464,823 A | 11/1995 | Lehrer et al. | |
| 5,470,951 A | 11/1995 | Roberts | |
| 5,514,548 A | 5/1996 | Krebber et al. | |
| 5,530,101 A * | 6/1996 | Queen et al. | ............. 530/387.3 |
| 5,571,499 A | 11/1996 | Hafler et al. | |
| 5,571,500 A | 11/1996 | Hafler et al. | |
| 5,576,184 A | 11/1996 | Better et al. | |
| 5,583,112 A | 12/1996 | Kensil et al. | |
| 5,585,089 A | 12/1996 | Queen et al. | |
| 5,585,100 A | 12/1996 | Mond et al. | |
| 5,589,154 A | 12/1996 | Anderson | |
| 5,593,846 A | 1/1997 | Schenk et al. | |
| 5,601,827 A | 2/1997 | Collier et al. | |
| 5,605,811 A | 2/1997 | Seubert et al. | |
| 5,612,486 A | 3/1997 | McConlogue et al. | |
| 5,618,920 A | 4/1997 | Robinson et al. | |
| 5,622,701 A | 4/1997 | Berg | |
| 5,624,821 A | 4/1997 | Winter et al. | |
| 5,624,937 A | 4/1997 | Reel et al. | |
| 5,641,473 A | 6/1997 | Hafler et al. | |
| 5,641,474 A | 6/1997 | Hafler et al. | |
| 5,645,820 A | 7/1997 | Hafler et al. | |
| 5,648,260 A | 7/1997 | Winter et al. | |
| 5,652,334 A | 7/1997 | Roberts | |
| 5,677,425 A | 10/1997 | Bodmer et al. | |
| 5,679,348 A | 10/1997 | Nesburn et al. | |
| 5,688,651 A | 11/1997 | Solomon | |
| 5,693,761 A | 12/1997 | Queen et al. | |
| 5,693,762 A | 12/1997 | Queen et al. | |
| 5,702,906 A | 12/1997 | Rosenthal | |
| 5,721,130 A | 2/1998 | Seubert et al. | |
| 5,731,284 A | 3/1998 | Williams | |
| 5,733,547 A | 3/1998 | Weiner et al. | |
| 5,733,548 A | 3/1998 | Restifo et al. | |
| 5,736,142 A | 4/1998 | Sette et al. | |
| 5,744,132 A | 4/1998 | Warne et al. | |

(Continued)

FOREIGN PATENT DOCUMENTS

| | | |
|---|---|---|
| AU | 707083 | 7/1999 |
| EP | 285 159 A1 | 10/1988 |
| EP | 0 391 714 A2 | 10/1990 |

(Continued)

OTHER PUBLICATIONS

Search output from ATCC website (pp. 1-3).*
Fundamental Immunology 242 (William E. Paul, M.D. ed., 3d ed. 1993).*

(Continued)

*Primary Examiner*—Lynn Bristol
(74) *Attorney, Agent, or Firm*—Alston and Bird LLP

(57) ABSTRACT

The invention provides improved agents and methods for treatment of diseases associated with amyloid deposits of Aβ in the brain of a patient. Preferred agents include antibodies, e.g., humanized antibodies.

32 Claims, 13 Drawing Sheets

U.S. PATENT DOCUMENTS

| | | | |
|---|---|---|---|
| 5,744,368 A | 4/1998 | Goldgaber et al. |
| 5,750,349 A | 5/1998 | Suzuki et al. |
| 5,750,361 A | 5/1998 | Prusiner et al. |
| 5,753,624 A | 5/1998 | McMichael et al. |
| 5,766,846 A | 6/1998 | Schlossmacher et al. |
| 5,770,700 A | 6/1998 | Webb et al. |
| 5,776,468 A | 7/1998 | Hauser et al. |
| 5,780,587 A | 7/1998 | Potter |
| 5,786,180 A | 7/1998 | Konig et al. |
| 5,798,102 A | 8/1998 | McMichael et al. |
| 5,817,626 A | 10/1998 | Findeis et al. |
| 5,824,322 A | 10/1998 | Balasubramanian |
| 5,837,268 A | 11/1998 | Potter et al. |
| 5,837,473 A | 11/1998 | Maggio et al. |
| 5,837,672 A | 11/1998 | Schenk et al. |
| 5,846,533 A | 12/1998 | Prusiner |
| 5,849,298 A | 12/1998 | Weiner et al. |
| 5,851,996 A | 12/1998 | Kline |
| 5,854,204 A | 12/1998 | Findeis et al. |
| 5,854,215 A | 12/1998 | Findeis et al. |
| 5,858,981 A | 1/1999 | Schreiber et al. |
| 5,859,205 A | 1/1999 | Adair et al. |
| 5,866,129 A | 2/1999 | Chang et al. |
| 5,869,046 A | 2/1999 | Presta et al. |
| 5,869,054 A | 2/1999 | Weiner et al. |
| 5,869,093 A | 2/1999 | Weiner et al. |
| 5,877,399 A | 3/1999 | Hsiao et al. |
| 5,891,991 A | 4/1999 | Wasco et al. |
| 5,935,927 A | 8/1999 | Vitek et al. |
| 5,955,079 A | 9/1999 | Mond et al. |
| 5,955,317 A | 9/1999 | Suzuki et al. |
| 5,958,883 A | 9/1999 | Snow |
| 5,985,242 A | 11/1999 | Findeis et al. |
| 5,989,566 A | 11/1999 | Cobb et al. |
| 5,994,083 A | 11/1999 | Felici et al. |
| 6,022,859 A | 2/2000 | Kiessling et al. |
| 6,054,297 A | 4/2000 | Carter et al. |
| 6,057,367 A | 5/2000 | Stamler et al. |
| 6,114,133 A | 9/2000 | Seubert et al. |
| 6,121,022 A | 9/2000 | Presta et al. |
| 6,150,091 A | 11/2000 | Pandolfo et al. |
| 6,165,745 A | 12/2000 | Ward et al. |
| 6,175,057 B1 | 1/2001 | Mucke et al. |
| 6,180,370 B1 | 1/2001 | Queen et al. |
| 6,194,551 B1 | 2/2001 | Idusogie et al. |
| 6,210,671 B1 | 4/2001 | Co |
| 6,218,506 B1 | 4/2001 | Krafft et al. |
| 6,261,569 B1 | 7/2001 | Comis et al. |
| 6,262,335 B1 | 7/2001 | Hsiao et al. |
| 6,267,958 B1 | 7/2001 | Andya et al. |
| 6,270,757 B1 | 8/2001 | Warne |
| 6,277,375 B1 | 8/2001 | Ward |
| 6,284,221 B1 | 9/2001 | Schenk et al. |
| 6,284,533 B1 | 9/2001 | Thomas |
| 6,294,171 B2 | 9/2001 | McMichael |
| 6,303,567 B1 | 10/2001 | Findeis et al. |
| 6,331,440 B1 | 12/2001 | Nordstedt et al. |
| 6,339,068 B1 | 1/2002 | Krieg et al. |
| 6,372,716 B1 | 4/2002 | Bush et al. |
| 6,399,314 B1 | 6/2002 | Krishnamurthy |
| 6,407,213 B1 | 6/2002 | Carter et al. |
| 6,417,178 B1 | 7/2002 | Klunk et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,562,341 B2 | 5/2003 | Prusiner et al. |
| 6,582,945 B1 | 6/2003 | Raso |
| 6,610,493 B1 | 8/2003 | Citron et al. |
| 6,632,927 B2 | 10/2003 | Adair et al. |
| 6,639,055 B1 | 10/2003 | Carter et al. |
| 6,710,226 B1 | 3/2004 | Schenk |
| 6,713,450 B2 | 3/2004 | Frangione et al. |
| 6,727,349 B1 | 4/2004 | LaRosa et al. |
| 6,743,427 B1 | 6/2004 | Schenk |
| 6,750,324 B1 | 6/2004 | Schenk et al. |
| 6,761,888 B1 | 7/2004 | Schenk |
| 6,787,129 B1 | 9/2004 | Klein et al. |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk et al. |
| 6,808,712 B2 | 10/2004 | Schenk |
| 6,818,218 B2 | 11/2004 | Schenk |
| 6,866,849 B2 | 3/2005 | Schenk |
| 6,866,850 B2 | 3/2005 | Schenk |
| 6,875,434 B1 | 4/2005 | Schenk |
| 6,890,535 B1 | 5/2005 | Schenk |
| 6,905,686 B1 | 6/2005 | Schenk |
| 6,913,745 B1 | 7/2005 | Schenk |
| 6,923,964 B1 | 8/2005 | Schenk |
| 6,933,368 B2 | 8/2005 | Co et al. |
| 6,936,698 B2 | 8/2005 | Taylor |
| 6,946,135 B2 | 9/2005 | Schenk |
| 6,962,707 B2 | 11/2005 | Schenk |
| 6,962,984 B2 | 11/2005 | Ishiwata et al. |
| 6,972,127 B2 | 12/2005 | Schenk |
| 6,982,084 B2 | 1/2006 | Schenk |
| 7,014,855 B2 | 3/2006 | Schenk |
| 7,179,892 B2 | 2/2007 | Basi et al. |
| 7,189,819 B2 | 3/2007 | Basi et al. |
| 7,195,761 B2 | 3/2007 | Holtzman et al. |
| 7,256,273 B2 | 8/2007 | Basi et al. |
| 2001/0018053 A1 | 8/2001 | McMichael |
| 2001/0021769 A1 | 9/2001 | Prusiner |
| 2002/0009445 A1 | 1/2002 | Du et al. |
| 2002/0058267 A1 | 5/2002 | Ozenberger et al. |
| 2002/0077288 A1 | 6/2002 | Frangione |
| 2002/0086847 A1 | 7/2002 | Chain |
| 2002/0094335 A1 | 7/2002 | Chalifour et al. |
| 2002/0102261 A1 | 8/2002 | Raso |
| 2002/0132268 A1 | 9/2002 | Chang et al. |
| 2002/0133001 A1 | 9/2002 | Gefter et al. |
| 2002/0136718 A1 | 9/2002 | Raso |
| 2002/0160394 A1 | 10/2002 | Wu |
| 2002/0162129 A1 | 10/2002 | Lannfelt |
| 2002/0168377 A1 | 11/2002 | Schaetzl |
| 2002/0187157 A1 | 12/2002 | Jensen et al. |
| 2002/0197258 A1 | 12/2002 | Ghanbari et al. |
| 2003/0039645 A1 | 2/2003 | Adair et al. |
| 2003/0068316 A1 | 4/2003 | Klein et al. |
| 2003/0068325 A1 | 4/2003 | Wang |
| 2003/0073655 A1 | 4/2003 | Chain |
| 2003/0092145 A1 | 5/2003 | Jira et al. |
| 2003/0135035 A1 | 7/2003 | Shannon |
| 2003/0147882 A1 | 8/2003 | Solomon et al. |
| 2003/0165496 A1 | 9/2003 | Basi et al. |
| 2003/0166557 A1 | 9/2003 | Minna et al. |
| 2003/0166558 A1 | 9/2003 | Frangione et al. |
| 2003/0202972 A1 | 10/2003 | Andya et al. |
| 2003/0207828 A1 | 11/2003 | Ishiwata et al. |
| 2004/0043418 A1 | 3/2004 | Holtzman et al. |
| 2004/0081657 A1 | 4/2004 | Schenk |
| 2004/0082762 A1 | 4/2004 | Basi et al. |
| 2004/0087777 A1 | 5/2004 | Basi et al. |
| 2004/0171815 A1 | 9/2004 | Schenk et al. |
| 2004/0171816 A1 | 9/2004 | Schenk et al. |
| 2004/0197324 A1 | 10/2004 | Liu et al. |
| 2004/0213800 A1 | 10/2004 | Seubert et al. |
| 2004/0219146 A1 | 11/2004 | Schenk |
| 2004/0241164 A1 | 12/2004 | Bales et al. |
| 2004/0247590 A1 | 12/2004 | Schenk et al. |

| | | | | | | |
|---|---|---|---|---|---|---|
| 2004/0247591 A1 | 12/2004 | Schenk et al. | EP | 561 087 B1 | 8/1999 | |
| 2004/0247612 A1 | 12/2004 | Wang | EP | 639 081 B1 | 11/1999 | |
| 2004/0265301 A1 | 12/2004 | Schenk et al. | EP | 506 785 B1 | 3/2000 | |
| 2004/0265308 A1 | 12/2004 | Schenk | EP | 1 172 378 A1 | 1/2002 | |
| 2004/0265919 A1 | 12/2004 | Vanderstichele et al. | EP | 1 481 992 A2 | 12/2004 | |
| 2005/0009150 A1 | 1/2005 | Basi et al. | EP | 1 481 992 A3 | 12/2004 | |
| 2005/0013815 A1 | 1/2005 | Schenk | EP | 921 189 B1 | 1/2005 | |
| 2005/0019328 A1 | 1/2005 | Schenk | EP | 1 033 998 B1 | 10/2005 | |
| 2005/0019330 A1 | 1/2005 | Schenk | GB | 2 220 211 A | 1/1990 | |
| 2005/0048049 A1 | 3/2005 | Schenk | GB | 2 335 192 A | 9/1999 | |
| 2005/0059591 A1 | 3/2005 | Schenk et al. | JP | 62-267297 A | 11/1887 | |
| 2005/0059802 A1 | 3/2005 | Schenk et al. | JP | 07-132033 A | 5/1995 | |
| 2005/0118651 A1 | 6/2005 | Basi et al. | JP | 7-165799 A | 6/1995 | |
| 2005/0123534 A1 | 6/2005 | Adair et al. | WO | WO 88/10120 A1 | 12/1988 | |
| 2005/0123544 A1 | 6/2005 | Schenk et al. | WO | WO 89/01343 A1 | 2/1989 | |
| 2005/0136054 A1 | 6/2005 | Adair et al. | WO | WO 89/03687 A1 | 5/1989 | |
| 2005/0142132 A1 | 6/2005 | Schenk et al. | WO | WO 89/06242 A1 | 7/1989 | |
| 2005/0147613 A1 | 7/2005 | Raso | WO | WO 89/06689 A1 | 7/1989 | |
| 2005/0152878 A1 | 7/2005 | Solomon et al. | WO | WO 90/12870 A1 | 11/1990 | |
| 2005/0158304 A1 | 7/2005 | Schenk et al. | WO | WO 90/12871 A1 | 11/1990 | |
| 2005/0163788 A1 | 7/2005 | Schenk | WO | WO 91/08760 A1 | 6/1991 | |
| 2005/0169925 A1 | 8/2005 | Bardroff et al. | WO | WO 91/09967 A1 | 7/1991 | |
| 2005/0191292 A1 | 9/2005 | Schenk | WO | WO 91/12816 A1 | 9/1991 | |
| 2005/0191314 A1 | 9/2005 | Schenk | WO | WO 91/16819 A1 | 11/1991 | |
| 2005/0196399 A1 | 9/2005 | Schenk et al. | WO | WO 91/16928 A1 | 11/1991 | |
| 2005/0249725 A1 | 11/2005 | Schenk et al. | WO | WO 91/19810 A1 | 12/1991 | |
| 2005/0249727 A1 | 11/2005 | Schenk | WO | WO 91/01059 | * | 1/1992 |
| 2005/0255122 A1 | 11/2005 | Schenk | WO | WO 92/06187 A1 | 4/1992 | |
| 2006/0029611 A1 | 2/2006 | Schenk | WO | WO 92/06708 A1 | 4/1992 | |
| 2006/0034858 A1 | 2/2006 | Schenk | WO | WO 92/13069 A1 | 8/1992 | |
| 2006/0099206 A1 | 5/2006 | Sinacore | WO | WO 92/22653 A1 | 12/1992 | |
| 2006/0153772 A1 | 7/2006 | Jacobsen | WO | WO 93/02189 A1 | 2/1993 | |
| 2006/0160161 A1 | 7/2006 | Pavlikova et al. | WO | WO 93/04194 A1 | 3/1993 | |
| 2006/0165682 A1 | 7/2006 | Basi et al. | WO | WO 93/14200 A1 | 7/1993 | |
| 2006/0188512 A1 | 8/2006 | Yednock et al. | WO | WO 93/15760 A1 | 8/1993 | |
| 2006/0193850 A1 | 8/2006 | Warne et al. | WO | WO 93/16724 A1 | 9/1993 | |
| 2006/0198851 A1 | 9/2006 | Basi et al. | WO | WO 93/21950 A1 | 11/1993 | |
| 2006/0210557 A1 | 9/2006 | Luisi et al. | WO | WO 94/00153 A1 | 1/1994 | |
| 2006/0240486 A1 | 10/2006 | Johnson-Wood et al. | WO | WO 94/01772 A1 | 1/1994 | |
| 2006/0257396 A1 | 11/2006 | Jacobsen | WO | WO 94/03615 A1 | 2/1994 | |
| 2006/0280743 A1 | 12/2006 | Basi et al. | WO | WO 94/05311 A1 | 3/1994 | |
| 2007/0082367 A1 | 4/2007 | Godavarti et al. | WO | WO 94/09364 A1 | 4/1994 | |
| 2007/0134762 A1 | 6/2007 | Arumugham et al. | WO | WO 94/10569 A1 | 5/1994 | |
| 2007/0154480 A1 | 7/2007 | Schenk | WO | WO 94/28412 A1 | 12/1994 | |
| 2007/0161088 A1 | 7/2007 | Arumugham et al. | WO | WO 95/04151 A2 | 2/1995 | |
| 2007/0238154 A1 | 10/2007 | Basi et al. | WO | WO 95/05393 A2 | 2/1995 | |
| 2008/0050367 A1 | 2/2008 | Basi et al. | WO | WO 95/05853 A1 | 3/1995 | |
| 2008/0096818 A1 | 4/2008 | Schenk et al. | WO | WO 95/06407 A1 | 3/1995 | |

FOREIGN PATENT DOCUMENTS

| | | | |
|---|---|---|---|
| WO | WO 95/07301 A1 | 3/1995 | |
| WO | WO 95/08999 A1 | 4/1995 | |
| EP | 451 700 A1 | 10/1991 | |
| WO | WO 95/11008 A2 | 4/1995 | |
| EP | 276 723 B1 | 12/1993 | |
| WO | WO 95/11311 A1 | 4/1995 | |
| EP | 597 101 A1 | 5/1994 | |
| WO | WO 95/11994 A1 | 5/1995 | |
| EP | 613 007 A2 | 8/1994 | |
| WO | WO 95/12815 A1 | 5/1995 | |
| EP | 620 276 A1 | 10/1994 | |
| WO | WO 95/17085 A1 | 6/1995 | |
| EP | 626 390 A1 | 11/1994 | |
| WO | WO 95/23166 A1 | 8/1995 | |
| EP | 666 080 A1 | 8/1995 | |
| WO | WO 95/23860 A2 | 9/1995 | |
| EP | 359 783 B1 | 11/1995 | |
| WO | WO 95/31996 A1 | 11/1995 | |
| EP | 683 234 A1 | 11/1995 | |
| WO | WO 96/08665 A2 | 3/1996 | |
| EP | 440 619 B1 | 1/1996 | |
| WO | WO 96/18900 A1 | 6/1996 | |
| EP | 758 248 B1 | 2/1997 | |
| WO | WO 96/25435 A1 | 8/1996 | |
| EP | 758 901 B1 | 2/1997 | |
| WO | WO 96/28471 A1 | 9/1996 | |
| EP | 526 511 B1 | 5/1997 | |
| WO | WO 96/37621 A2 | 11/1996 | |
| EP | 782 859 A1 | 7/1997 | |
| WO | WO 96/39176 A1 | 12/1996 | |
| EP | 783 104 A1 | 7/1997 | |
| WO | WO 97/03192 A3 | 1/1997 | |
| EP | 594 607 B1 | 8/1997 | |
| WO | WO 97/08320 A1 | 3/1997 | |
| EP | 752 886 B1 | 1/1998 | |
| WO | WO 97/10505 A1 | 3/1997 | |
| EP | 845 270 A1 | 6/1998 | |
| WO | WO 97/17613 A1 | 5/1997 | |
| EP | 863 211 A1 | 9/1998 | |
| WO | WO 97/21728 A1 | 6/1997 | |
| EP | 868 918 A2 | 10/1998 | |
| WO | WO 97/32017 A1 | 9/1997 | |
| EP | 652 962 B1 | 12/1998 | |
| WO | WO 98/02462 A1 | 1/1998 | |
| | | | |
| | | | |
| WO | WO 98/05350 A1 | 2/1998 | |
| EP | 911 036 A2 | 4/1999 | |
| WO | WO 98/07850 A2 | 2/1998 | |

| | | |
|---|---|---|
| WO | WO 98/08868 A1 | 3/1998 |
| WO | WO 98/22120 A1 | 5/1998 |
| WO | WO 98/33815 A1 | 8/1998 |
| WO | WO 98/44955 A1 | 10/1998 |
| WO | WO 98/56418 A1 | 12/1998 |
| WO | WO 99/00150 A2 | 1/1999 |
| WO | WO 99/06066 A2 | 2/1999 |
| WO | WO 99/06587 A2 | 2/1999 |
| WO | WO 99/10008 A1 | 3/1999 |
| WO | WO 99/27911 A1 | 6/1999 |
| WO | WO 99/27944 A1 | 6/1999 |
| WO | WO 99/27949 A1 | 6/1999 |
| WO | WO 99/06545 A2 | 11/1999 |
| WO | WO 99/58564 A1 | 11/1999 |
| WO | WO 99/60021 A2 | 11/1999 |
| WO | WO 99/60024 A1 | 11/1999 |
| WO | WO 00/20027 A2 | 4/2000 |
| WO | WO 00/23082 A1 | 4/2000 |
| WO | WO 00/26238 A2 | 5/2000 |
| WO | WO 00/43039 A1 | 7/2000 |
| WO | WO 00/43049 A1 | 7/2000 |
| WO | WO 00/68263 A2 | 11/2000 |
| WO | WO 00/72870 A1 | 12/2000 |
| WO | WO 00/72876 A2 | 12/2000 |
| WO | WO 00/72876 A3 | 12/2000 |
| WO | WO 00/72880 A2 | 12/2000 |
| WO | WO 00/72880 A3 | 12/2000 |
| WO | WO 00/77178 A1 | 12/2000 |
| WO | WO 01/05355 A2 | 1/2001 |
| WO | WO 01/10900 A2 | 2/2001 |
| WO | WO 01/18169 A3 | 3/2001 |
| WO | WO 01/39796 A2 | 6/2001 |
| WO | WO 01/42306 A2 | 6/2001 |
| WO | WO 01/62284 A2 | 8/2001 |
| WO | WO 01/62801 A2 | 8/2001 |
| WO | WO 01/77167 A2 | 10/2001 |
| WO | WO 01/90182 A2 | 11/2001 |
| WO | WO 02/03911 A2 | 1/2002 |
| WO | WO 02/21141 A2 | 3/2002 |
| WO | WO 02/34777 A1 | 5/2002 |
| WO | WO 02/34878 A2 | 5/2002 |
| WO | WO 02/46237 A1 | 6/2002 |
| WO | WO 02/46237 A3 | 6/2002 |
| WO | WO 02/060481 A1 | 8/2002 |
| WO | WO 02/088306 A2 | 11/2002 |
| WO | WO 02/088307 A2 | 11/2002 |
| WO | WO 02/096457 A2 | 12/2002 |
| WO | WO 02/096937 A2 | 12/2002 |
| WO | WO 03/009817 A2 | 2/2003 |
| WO | WO 03/015691 A2 | 2/2003 |
| WO | WO 03/016466 A2 | 2/2003 |
| WO | WO 03/016467 A2 | 2/2003 |
| WO | WO 03/016467 A3 | 2/2003 |
| WO | WO 03/020212 A2 | 3/2003 |
| WO | WO 03/039485 A2 | 5/2003 |
| WO | WO 03/051374 A2 | 6/2003 |
| WO | WO 03/072036 A2 | 9/2003 |
| WO | WO 03/072036 A3 | 9/2003 |
| WO | WO 03/074081 A1 | 9/2003 |
| WO | WO 03/077858 A2 | 9/2003 |
| WO | WO 03/077858 A3 | 9/2003 |
| WO | WO 03/104437 A2 | 12/2003 |
| WO | WO 03/105894 A1 | 12/2003 |
| WO | WO 2004/013172 A2 | 2/2004 |
| WO | WO 2004/013172 A3 | 2/2004 |
| WO | WO 2004/031400 A2 | 4/2004 |
| WO | WO 2004/044204 A2 | 5/2004 |
| WO | WO 2004/044204 A3 | 5/2004 |
| WO | WO 2004/055164 A2 | 7/2004 |
| WO | WO 2004/069182 A2 | 8/2004 |
| WO | WO 2004/071408 A2 | 8/2004 |
| WO | WO 2004/080419 A2 | 9/2004 |
| WO | WO 2004/080419 A3 | 9/2004 |
| WO | WO 2004/108895 A2 | 12/2004 |
| WO | WO 2004/108895 A3 | 12/2004 |
| WO | WO 2005/014041 A2 | 2/2005 |
| WO | WO 2005/026211 A2 | 3/2005 |
| WO | WO 2005/026211 A3 | 3/2005 |
| WO | WO 2005/058940 A2 | 6/2005 |
| WO | WO 2005/058941 A2 | 6/2005 |
| WO | WO 2006/081587 A2 | 8/2006 |
| WO | WO 2006/081587 A3 | 8/2006 |
| WO | WO 2006/083689 A2 | 8/2006 |

OTHER PUBLICATIONS

Amit et al. Science 233: 747-753, 1986.*
Rudikoff et al (Proc Natl Acad Sci USA 1982 vol. 79 p. 1979.*
Coleman (Research in Immunol. 145:33-36, 1994).*
Panka et al (Proc Natl Acad Sci USA 85: 3080-3084.*
Bard et al. (PNAS 100(4):2023-2028 (Feb. 18, 2003)).*
Putative CDR determination for SEQ ID Nos. 2 and 4 (pp. 1-2).*
Studnicka et al. (Protein Eng. 7(6):805-814 (1994).*
Bard, Frédérique et al., "Epitope and isotype specificities of antibodies to β-amyloid peptide for protection against Alzheimer's disease-like neuropathology," *PNAS*, vol. 100(4):2023-2028 (2003).
U.S. Appl. No. 11/245,524, filed Oct. 7, 2005, Schenk.
U.S. Appl. No. 11/245,916, filed Oct. 7, 2005, Schenk.
U.S. Appl. No. 60/067,740, filed Dec. 2, 1997, Schenk.
U.S. Appl. No. 60/067,219, filed Dec. 3, 1997, Weiner et al.
U.S. Appl. No. 60/079,697, filed Mar. 27, 1998, Weiner et al.
U.S. Appl. No. 60/080,970, filed Jan. 11, 1999, Schenk.
Alberts et al., eds. *Molecular Biology of The Cell, Third Edition*, chapter 23, pp. 1208-1209 (1994).
Alberts et al., *Molecular Biology of the Cell, 2nd Edition*, pp. 266-267, Garland Publishing Inc., New York (1989).
Ankarcrona et al., "Biomarkers for apoptosis in Alzheimer's disease," *Int. J. Geriatric Psychiatry*, 20:101-105 (2005).
Auld et al., "Alzheimer's disease and the basal forebrain cholinergic system: relations to β-amyloid peptides, cognition, and treatment strategies," *Progress in Neurobiol.*, 68:209-245 (2002).
Bales et al., "Administration of an Anti-Aβ Fab Fragment to APP$^{V717F}$ Transgenic Mice Reduces Neuritic Plaque," Abstract P$-396, p. S587, presented at Poster Session P4: Therapeutics and Therapeutic Strategies-Therapeutic Strategies, Amyloid-Based.
Bickel et al., "Development and in Vitro Characterization of a Cationized Monoclonal Antibody against βA4 Protein: A Potential Probe for Alzheimer's Disease," *Bioconjugate Chem.*, 5:119-125 (1994).
Blasberg et al., "Regional Localization of Glioma-assoicated Antigen Defined by Monoclonal Antibody 81C6 in Vivo: Kinetics and Implications for Diagnosis and Therapy," *Cancer Research*, 47:4432-4443 (1987).
Brazil et al., "Effects of Incorporation of Immunoglobulin G and Complement Component C1q on Uptake and Degradation of Alzheimer's Disease Amyloid Fibrils by Microglia," *J. Biol. Chem.*, 275(22):16941-16947 (2000).
Bussiere et al., "Morphological Characterization of Thioflavin-S-Positive Amyloid Plaques in Transgenic Alzheimer Mice and Effect of Passive Aβ Immunotherapy on Their Clearance," *Am. J. Pathology*, 165(3):987-995 (2004).
Clayton et al.,"Synucleins in Synaptic Plasticity and Neurodegenerative Disorders," *J. Neurosci. Res.*, 58:120-129 (1999).
Coico et al., *Immunology A Short Course, Fifth Edition*, pp. 18-24 (2003).
Cox et al., "Adjuvants—a classification and review of their modes of action," *Vaccine*, 15(3):248-256 (1997).
Davis, S. S., "Nasal Vaccines," *Advanced Drug Delivery Reviews*, 51:21-42 (2001).
De Lustig et al., "Peripheral Markers and Diagnostic Criteria in Alzheimer's Disease: Critical Evaluations," *Rev. In Neurosciences*, 5:213-225 (1994).
Dewitt et al., "Astrocytes regulate microglial phagocytosis of senile plaque cores of Alzheimer's disease," *Experimental Neurology*, 149:329-340 (1998).
Dictionary.com definition of "prophylactic", pp. 1-3 downloaded from Internet Oct. 12, 2005.

Di Martino et al., "Production and Characterization of Antibodies to Mouse Scrapie-Amyloid Protein Elicited by Non-carrier Linked Synthetic Peptide Immunogens," *J. Molecular Recognition*, 4(2-3):85-91 (1991).

Du et al., "$\alpha_2$-Macroglobulin as a β-Amyloid Peptide-Binding Plasma Protein," *J. Neurochemistry*, 69(1):299-305 (1997).

European Search Report of May 22, 2006 for European Application 06075704.4-2107.

European Search Report of May 22, 2006 for European Application 06075479.3-2107.

Gupta et al., "Adjuvants for human vaccines—current status, problems and future prospects," *Vaccine*, 13(14):1263-1276 (1995).

Hara et al.. "Development of a safe oral Aβ vaccine using recombinant adeno-associated virus vector for Alzheimer's disease," *J. Alzheimer's Disease*, 6:483-488 (2004).

Harlow et al., eds., *Antibodies: A Laboratory Manual*, pp. 71-82 (1998).

Hirschfield et al., "Amyloidosis: new strategies for treatment," *The International Journal of Biochemistry & Cell Biology*, vol. 35:1608-1613 (2003).

Ida et al., "Analysis of Heterogeneous βA4 Peptides in Juman Cerebrospinal Fluid and Blood by a Newly Developed Sensitive Western Blot Assay," *J. Biol. Chem.*, 271(37):22908-22914 (1996).

Kajkowski et al., "β-Amyloid Peptide-induced Apoptosis Regulated by a Novel Protein Containing a G Protein Activation Module," *J. Biol. Chem.*, 276(22):18748-18756 (2001).

Kascsak at al., "Mouse Polyclonal and Monoclonal Antibody to Scrapie-Associated Fibril Proteins," *J. Virology*, 61(12):3688-3693 (1987).

Kofler et al., "Immunoglobulin $_k$ Light Chain Variable Region Gene Complex Organization and Immunoglobulin Genes Encoding Anti-DNA Autoantibodies in Lupus Mice," *J. Clin. Invest.*, 82:852-860 (1988).

Kuo et al., "Water-soluble Aβ (N-40, N-42) Oligomers in Normal and Alzheimer Disease Brains," *J. Biol. Chem.*, 271(8):4077-4081 (1996).

Kurashima et al., "Production of Monoclonal Antibody against Amyloid Fibril Protein and Its Immunohistochemical Application," *Appl. Pathol.*, 3(1-2):39-54 (1985).

LaDu et al., "Isoform-specific Binding of Apolipoprotein E to β-Amyloid," *J. Biol. Chem.*, 269(38):23403-23406 (1994).

Lavie et al., "EFRH-Phage Immunization of Alzheimer's Disease Animal Model Improves Behavioral Performance in Morris Water Maze Trials," *J. Molecular Neuroscience*, 24:105-113 (2004).

Licastro et al., "Is immunotherapy an effective treatment for Alzheimer's disease?," *Immunity & Aging*, 1:1-2 (2004).

Linke, "Monoclonal antibodies against amyloid fibril protein AA. Production, specificity, and use for immunohistochemical localization and classification of AA-type amyloidosis," *J. Histochemistry and Cytochemistry*, 32(3):322-328 (1982).

Lo et al., "High level expression and secretion of Fc-X fusion proteins in mammalian cells" *Protein Engineering*, 11(6):495-500 (1998).

Mandel et al., "Clinical trials in neurological disorders using AAV vectors: promises and challenges," *Curr. Opin. Mol. Ther.*, 6(5):482-490 (2004).

Manoj et al., "Approaches to Enhance the Efficacy of DNA Vaccines," *Critical Rev. Clin. Lab. Sci.*, 41(1):1-39 (2004).

Marhaug et al., "Monoclonal hybridoma antibodies to human amyloid related protein SAA," *Clin. Exp. Immunol.*, 50(2):390-396 (1982).

Marotta et al., "Overexpression of amyloid precursor protein A4 (β-amyloid) immunoreactivity in genetically transformed cells: Implications for a cellular model of Alzheimer amyloidosis," *PNAS*, 86:337-341 (1989).

Maury et al., "Immunohistochemical Localization of Amyloid in Finnish Hereditary Amyloidosis wtih Antibodies to Gelsolin Peptides," *Laboratory Investigation*, 64(3):400-404 (1991).

Okura et al., "Nonviral Aβ DNA vaccine therapy against Alzheimer's disease: Long-term effect and safety," *PNAS*, 103(25):9619-9624 (2006).

Parnetti et al., "Cognitive Enhancement Therapy for Alzheimer's Disease, The Way Forward," *Drugs*, 53(5):752-768 (1997).

PCT Search Report of Aug. 11, 2006 for application PCT/US2006/002837.

Peeters et al., "Comparison of four bifunctional reagents for coupling peptides to proteins and the effect of the three moieties on the immunogenicity of the conjugates," *J. Immunological Methods*, 120:133-143 (1989).

Phelps et al., "Development and Characterization of Monoclonal Antibodies Specific for Amylin," *Hybridoma*, 15(5):379-386. (1996).

Probert et al., "Spontaneous inflammatory demyelinating disease in transgenic mice showing central nervous system-specific expression of tunmor necrosis factor α," *PNAS*, 92:11294-11298 (1995).

Qu et al., "A$\beta_{42}$ gene vaccination reduces brain amyloid plaque burden in transgenic mice," *J. Neurological Sciences*, 244:151-158 (2006).

Schenk et al., "Current progress in beta-amyloid immunotherapy," *Current Opinion in Immunology*, vol. 16:599-606 (2004).

Schmitt et al., "Interactions of the alzheimer β amyloid fragment$_{(25-35)}$ with peripheral blood dendritic cells," *Mechanisms of Ageing and Development*, 94:223-232 (1997).

Shinkai et al., "Amyloid β-Proteins 1-40 and 1-42(43) in the Soluble Fraction of Extra- and Intracranial Blood Vessels," *Ann. Neurol.*, 38:421-428 (1995).

Small et al., "Cerebral metabolic and cognitive decline in persons at genetic risk for Alzheimer's disease," *PNAS* 97(11):6037-6042 (2000).

Souder et al., "Overview of Alzheimer's disease," *Nurs. Clin. N. Am.*, 39:545-559 (2004).

Trieb et al., "APP Peptides Stimulate Lymphocyte Proliferation in Normals, But Not in Patients With Alzheimer's Disease," *Neurobiology of Aging*, 17(4):541-547. (1996).

Urmoneit et al., "Cerebrovascular Smooth Muscle CElls Internalize Alzheimer Amyloid Beta Protein via a Lipoprotein Pathway: Implications for Cerebral Amyloid Angiopathy," *Laboratory Investigation*, 77(2):157-166 (1997).

Valleix et al., "Hereditary renal amyloidosis caused by a new variant lysozyme W64R in a French family," *Kidney International*, 61:907-912 (2002).

Van Den Dobbelsteen et al., "Characteristics of Immune Responses to Native and Protein Conjugated Pneumococcal Polysaccharide Type 14," *Scand. J. Immunol.*, 41:273-280 (1995).

Vickers, J. C., "A Vaccine Against Alzheimer's Disease," *Drugs Aging*, 19(7):487-494 (2002).

Vidanovic et al., "Effects of nonionic surfactants on the physical stability of immunoglobulin G in aqueous solution during mechanical agitation," *DIE Pharmazie*, 58(6):399-404 (2003).

Wang, W., "Instability, stabilization, and formulation of liquid protein pharmaceuticals," *Int. J. Pharmaceutics*, 185(2):129-188 (1999).

*Webster's New World Dictionary*, p. 1387, therapeutic (1988).

*Webster's New World Dictionary of American English*, Third College Edition, p. 1078 (1988).

Weiner, H. L., "Oral tolerance: immune mechanisms and treatment of autoimmune diseases," *Immunology Today*, 18:335-343 (1997).

Weinreb et al., "NACP, A Protein Implicated in Alzheimer's Disease and Learning, Is Natively Unfolded," *Biochemistry*, 35(43):13709-13715 (1996).

Wikipedia definition of "epitope" printed from internet on Apr. 26, 2006.

Wikipedia definition of "antigen" printed from internet on Apr. 26, 2006.

Wikipedia definition of "route of administration including parenteral" printed from internet on Apr. 26, 2006.

Yamada et al., "Generation and Characterization of Rat Monoclonal Antibodies Against Human Serum Amyloid A," *Scand. J. Immunol*, 46(2):175-179 (1997).

Zameer et al., "Single Chain Fv Antibodies against 25-35 Peptide Fragment of Amyloid-β: Potential Therapeutic for Alzheimer's Disease," Abstract P4-420, p. S593, presented at Poster Session P4:Therapeutics and Therapeutic Strategies-Therapeutic Strateies, Amyloid-Based.

Zhang et al., "A novel recombinant adeno-assoclated virus vaccine reduces behavioral impairment and β-amyloid plaques in a mouse model of Alzheimer's disease," *Neurobiology of Disease*, 14:365-379 (2003).
U.S. Appl. No. 60/254,465, filed Dec. 8, 2000, Holtzman et al.
U.S. Appl. No. 60/254,498, filed Dec. 8, 2000, Holtzman et al.
U.S. Appl. No. 09/724,842, filed Nov. 28, 2000, Chalifour et al.
U.S. Appl. No. 60/186,295, filed Mar. 1, 2000, Rasmussen et al.
U.S. Appl. No. 60/184,601, filed Feb. 24, 2000, Holtzman et al.
U.S. Appl. No. 60/169,687, filed Dec. 8, 1999, Chain.
U.S. Appl. No. 60/168,594, filed Nov. 29, 1999, Chalifour et al.
U.S. Appl. No. 09/441,140, filed Nov. 16, 1999, Solomon et al.
Aguzzi et al., "Prion research: the next frontiers," *Nature*, 389:795-798 (1997).
Akiyama et al., "Occurrence of the Diffuse Amyloid β-Protein (Aβ) Deposits With Numerous Aβ-Containing Glial Cells in the Cerebral Cortex of Patients With Alzheimer's Disease," *Glia*, 25:324-331 (1999).
Akiyama et al., "Inflammation and Alzheimer's disease," *Neurobiology of Aging*, 21:383-421 (2000).
Amit et al., "Three-Dimensional Structure of an Antigen-Antibody Complex at 2.8 Å Resolution," *Science*, 233:747-753 (1986).
Andersen et al., "Do nonsteroidal anti-inflammatory drugs decrease the risk for Alzheimer's disease?" *Neurology*, 45:1441-1445 (1995).
Anderson, J. P., "Exact cleavage site of Alzheimer amyloid precursor in neuronal PC-12 cells," *Neuroscience Letters*, 128(1):126-128 (1991).
Anderson, M. W., "Amending the amyloid hypothesis," *The Scientist*, 18(20):28-29 (2004).
Andrew et al., *Current Protocols in Immunology*, 2.7.1-2.9.8, John Wiley & Sons, Inc. (1997).
Arendiash et al., "Behavioral assessment of Alzheimer's transgenic mice following long-term Aβ vaccination: Task specificity and correlations between Aβ deposition and spatial memory," *DNA and Cell Biology*, 20(11):737-744 (2001).
Associated Press, "Immune cells may promote Alzheimer's, a study finds," *The Boston Globe* (Apr. 13, 1995).
Bacskai et al., "Imaging of amyloid-β deposits in brains of living mice permits direct observation of clearance of plaques with immunotherapy," *Nature Medicine*, 7(3):369-372 (2001).
Bacskai et al., "Non-Fc-mediated mechanisms are involved in clearance of amyloid-β in vivo by immunotherapy," *J. Neurosci.*, 22(18):7873-7878 (2002).
Balbach et al., "Amyloid fibril formation by Aβ$_{16-22}$, a seven-residue fragment of the Alzheimer's β- amyloid peptide, and structural characterization by solid state NMR," *Biochemistry*, 39:13748-13759 (2000).
Bard et al., "Peripherally administered antibodies against amyloid β-peptide enter the central nervous system and reduce pathology in a mouse model of Alzheimer disease," *Nature Medicine*, 6(8):916-919.
Bard et al., "Epitope and isotype specificities of antibodies to β-amyloid peptide for protection against Alzheimer's disease-like neuropathology," *PNAS*, 100(4):2023-2028 (2003).
Barrow et al., "Solution Conformations and aggregational Properties of Synthetic Amyloid Beta-Peptides of Alzheimer's Disease. Analysis of Circular Dichroism Spectra," *J. Mol. Biol.*, 225(4):1075-1093 (1992).
Bauer et al., "Interleukin-6 and α-2-macroglobulin indicate an acute-phase state in Alzheimer's disease cortices," *FEBS Letters*, 285(1):111-114 (1991).
Beasley, "Alzheimer's traced to proteins caused by aging," Reuters, Apr. 20, 2001 7:56 PM ET.
Bellotti et al., "Application of Monoclonal Anti-idiotypes in the Study of AL Amyloidosi: Therapeutic Implications," *Renal Failure*, 15(3):365-371 (1993).
Benjamini et al., from *Immunology A Short Course*, Second Edition, Chapter 4, Antibody Structure, pp. 49-65, 1991, published by Wiley-Liss, Inc., New York, New York.
Benjamini et al., from *Immunology A Short Course*, Second Edition, pp. 136-138, 143, 73-74, 372-373, and 400-401, 1991, published by Wiley-Liss, Inc., New York, New York.

Benkirane, et al, "Antigenicity and Immunogenicity of Modified Synthetic Peptides Containing D-Amino Acid Residues," *J. Biol. Chem.*, 268(23):26279-26285 (1993).
Bercovici et al., "Chronic Intravenous Injections of Antigen Induce and Maintain Tolerance in T Cell Receptor-Transgenic Mice," *Eur. J. Immunol.*, 29:345-354 (1999).
Bickel et al., "Site Protected, Cationized Monoclonal Antibody Against Beta Amyloid as a Potential Diagnostic Imaging Technique for Alzheimer's Diseases," *Soc. for Neuroscience Abstracts*, 18:764 (1992).
Blass, "Immunologic Treatment of Alzheimer's Disease," *New England J. Medicine*, 341(22):1694 (1999).
Bodmer et al., "Transforming Growth Factor-Beta Bound to Soluble Derivatives of the Beta Amyloid Precursor Protein of Alzheimer's Disease," *Biochem. Biophys. Res. Comm.*, 171(2):890-897 (1990).
Borchelt et al., "Accelerated Amyloid Deposition in the Brains of Transgenic Mice Coexpressing Mutant Presenilin 1 and Amyloid Precursor Proteins," *Neuron*, 19:939-945 (1997).
Boris-Lawrie et al., "Recent advances in retrovirus vector technology," *Cur. Opin. Genetic Develop.*, 3:102-109 (1993).
Bork et al., "Go hunting in sequence databases but watch out for the traps," *Trends in Genetics*, 12(10):425-427 (1996).
Bork, P., "Powers and Pitfalls in Sequence Analysis: The 70% Hurdle," *Genome Research*, 10:398-400 (2000).
Brenner, S. E., "Errors in genome annotation," *Trends in Genetics*, 15(4):132-133 (1999).
Brice et al., "Absence of the amyloid precursor protein gene mutation (APP717 : Val->Ile) in 85 cases of early onset Alzheimer's disease," *J. Neurology, Neurosurg. Psychiatry*, 56:112-115 (1993).
Burdick et al., "Assembly and aggregarbon properties of synthetic Alzheimer's A4/β amyloid peptide antigens," *J. Biol. Chem.*, 267:546-555 (1992).
Cameron, "Recent Advances in Transgenic Technology," *Molecular Biotechnology*, 7:253-265 (1997).
Caputo et al., "Therapeutic approaches targeted at the amyloid proteins in Alzheimer's disease," *Clin. Neuropharm.*, 15:414A-414B (1992).
Castillo et al., "Amylin / Islet Amyloid Polypeptide: Biochemistry, Physiology, Patho-Physiology," *Diabete & Metabolisme* (Paris), 21:3-25 (1995).
Center for Biologics Evaluation and Research, U.S. Food and Drug Administration, Thimerosal in Vaccines (Mercury in Plasma-Derived Products), web site contents found at : http://www.fda.gov/cber/vaccine/thimerosal.htm, last updated May 16, 2002.
Chao et al., "Transforming Growth Factor-β Protects human Neurons Against β-Amyloid-Induced Injury," *Soc. Neurosci. Abstracts*, 19:513-7 (1993).
Chapman, "Model behavior," *Nature*, 408:915-916 (2000).
Check, "Battle of the Mind," *Nature*, 422:370-372 (2003).
Chemical Abstract database, Abstract of "Injection of Newborn Mice with Seven Chemical Adjuvants to Help Determine Their Safety in Use in Biologicals," Chemical Abstract database. (Publication date unknown.).
Chimicon International, "Mouse Anti-Amyloid Beta Protein Monoclonal Antibody," Catalog # MAB1561.
Chen et al., "Neurodegenerative Alzheimer-like pathology in PDAPP 717V→F transgenic mice," *Progress in Brain Research*, 117:327-337 (1998).
Chen et al., "A learning deficit related to age and beta-amyloid plaques in a mouse model of Alzheimer's disease," *Nature*, 408(6815):975-979 (2000).
Chen et al., "An Antibody to β Amyloid Precursor Protein Inhibits Cell-substratum Adhesion in Many Mammalian Cell Types," *Neuroscience Letters*, 125:223-226 (1991).
Chishti et al., "Early-onset Amyloid Deposition and Cognitive Deficits in Transgenic Mice Expressing a Double Mutant Form of Amyloid Precursor Protein 695," *J. Biol.Chem.*, 276(24):21562-70 (2001).
Chothia et al., "Domain Association in Immunoglobulin Molecules," *J. Mol. Biol.*, 186:651-663 (1985).
Chromy et al., "Self-assembly of Aβ(1-42) into globular neurotoxins," *Biochemistry*, 42(44):12749-12760 (2003).

Chung et al., "Uptake, Degradation, and Release of Fibrillar and Soluble Forms of Alzheimer's Amyloid β-Peptide by Microglial Cells," *J. Biol. Chem.*, 274(45):32301-32308 (1999).

Cirrito et al., "Amyloid β and Alzheimer disease therapeutics: the devil may be in the details," *J. Clin. Invest.*, 112:321-323 (2000).

Citron at al., "Evidence that the 42- and 40-amino acid forms of amyloidβ protein are generated from the β-amyloid precursor protein by different protease activities," *PNAS*, 93(23):13170-13175 (1996).

Citron, M., "Alzheimer's disease: treatments in discovery and development," *Nat Neurosci.*, 5:1055-1057 (2002).

Co at al, "Chimeric and humanized antibodies with specifdly for the CD33 antigen," *J. Immunol.*, 148:1149-1154 (1992).

Coloma et al., "Transport Across the Primate Blood-Brain Barrier of a Genetically Engineered Chimeric Monoclonal Antibody to the Human Insulin Receptor," *Pharm. Res.*, 17:266-274 (2000).

Conway et al., "Acceleration of oligomerization, not fibrillization, is a shared property of both αsynuclein mutations linked to early-onset Parkinson's disease: Implications for pathogenesis and therapy," *PNAS*, 97(2):571-576 (2000).

Cordell, B., "β-Amyloid formation as a potential therapeutic target for Alzheimer's disease," *Ann. Rev. Pharmacol. Toxicol.*, 34:69-89 (1994).

Costa et al., "Immunoassay for transthyretin variants associated with amyloid neuropathy," *Scand. J. Immunol.*, 38:177-182 (1993).

Cribbs et al., "All-D-Erantiomers of Beta-Amyloid Exhibit Similar Biological Properties to All-L-Beta-Amyloids," *J. Biol. Chem.*, 272:7431-7436 (1997).

Daly, et at., "Detection of the membrane-retained carboxy-terminal tail containing polypeptides of the amyloid precursor protein in tissue from Alzheimer's Disease brain," *Life Sci.*, 63:2121-2131 (1998).

Das et al., "Amyloid-β Immunization Effectively Reduces Amyloid Deposition in FcRγ Knock-Out-Mice," *J. Neuroscience*, 23(24):8532-8538 (2003).

Demattos et al., "Peripheral anti-Aβ antibody alters CNS and plasma clearance and decreases Aβ burden in a mouse model of Alzheimer's disease," *PNAS*, 98(15):8850-8855 (2001).

Demattos et al., "Peripheral Anti Aβ Antibody Alters CNS And Plasma Aβ Clearance and Decreases Brain Aβ Burden in a Mouse Model of Alzheimer's Disease," *PNAS early edition*, 10.1073/pnas. 151261398 (2001).

Demattos et al., "Plaque-associated disruption of CSF and plasma amyloid-β (Aβ) equilibrium in a mouse model of Alzheimer's disease," *J. Neurochem.*, 81:229-236 (2002).

Demattos et al., "Brain to plasma amyloid-β efflux: a measure of brain amyoid burden in a mouse model of Alzheimer's disease," *Science*, 295(5563):2264-2267 (2002).

Dialog/Derwent, Abstract of WPI Acc No. 1997-054436/199706: Stable vaccine compsns.—comprise a macrocyclic lactone, a milbemycin, an avermectin, an antigen, a dispersing agent, an adjuvant, a water sol. organic solvent and saline or water, Derwent File 351: Dement WPI database. (Publication date unknown.).

Dickey et al., "Duration and specificity of humoral immune responses in mice vaccinated with the Alzheimer's disease-associated β-amyloid 1-42 peptide," *DNA and Cell Biology*, 20(11):723-729 (2001).

Dickson et al., "Neuroimmunology of Alzheimer's disease: a conference report," *Neurobiology of Aging*, 13(6):793-798 (1992), abstract only.

Diomede et al., "Activation effects of a prion protein fragment [PrP-(106-126)] on human leucocytes," *Biochem. J.*, 320:563-570 (1996).

Dodart, "Immunotherapy for Alzheimer's disease: will vaccination work?," *Trends in Molecular Medicine*, 9(3):85-87 (2003).

Dodart et al., "Immunization reverses memory deficits without reducing brain Aβ burden in Alzheimer's disease model," *Nat. Neurosci.*, 5(5):452-457 (2002).

Dodel et al., "Immunotherapy for Alzheimer's disease," *Lancet Neurol.*, 2(4):215-220 (2003).

Doerks et al, "Protein annotation: detective work for function prediction," *Trends in Genetics*, 14(6):248'250 (1998).

Dovey et al., "Functional gamma-secretase inhibitors reduce beta-amyloid peptide levels in brain," *J. Neurochem.*, 76(1):173-181 (2001).

Du et al., "Reduced levels of amyloid beta-peptide antibody in Alzheimer disease," *Neurology*, 57(5):801-5 (2001).

Duff et al., "Mouse model made," *Nature*, 373:476-477 (1995).

Duff et al., "Increased amyloid-β42(43) in brains of mice expressing mutant presenilin 1," *Nature*, 383(6602):710-713 (1996).

Dumery et al., "β-Amyloid protein aggregation: its implication in the physiopathology of Alzheimer's disease," *Pathol. Biol.*, 49:72-85 (2001).

Eck et al., *Goodman and Gilman's The pharmacological basis of therapeutics*, Chapter 5, pp. 77-101 (1996).

El-Agnaf et al., "The influence of the central region containing residues 19-25 on the aggregation properties and secondary structure of Alzheimer's beta-amyloid peptide," *Eur. J. Biochem.*, 256(3):560-569 (1998).

Elan, "Elan and AHP Provide an Update on the Phase 2A Clinical Trial of AN-1792," Press Release. (Jan. 18, 2002).

Elan, "Elan and Wyeth Provide Update on Status of Alzheimer's Collaboration," Press Release (Mar. 1, 2002).

Elizan et al., "Antineurofilament antibodies in a postencephalitic and idiopathic Parkinson's disease," *J. Neurol. Sciences*, 59:341-347 (1983).

Eriksen et al., "NSAIDs and enantiomers of flurbiprofen target γ-secretase and lower Aβ42 in vivo," *J. Clin. Invest.*, 112(3):440-449 (2003).

Esiri, "Is an effective immune intervention for Alzheimer's disease in prospect?", *Trends in Pharm, Sci.*, 22:2-3 (2001).

Esler et at., "Point substitution in the central hydrophobic cluster of a human β-amyloid congener disrupts peptide folding and abolishes plaque competence," *Biochemistry*, 35:13914-13921 (1996).

Felsenstein et al., "Processing of the β-amyloid precursor protein carrying the familial, Dutch-type, and a novel recombinant C-terminal mutation," *Neuroscience Letters*, 152:185-189 (1993).

Felsenstein et al., "Transgenic Rat and In-Vitro Studies of B-Amyloid Precursor Protein Processing;" *Alzheimer's and Parkinson's Diseases*, Hanin et al. Ed., pp. 401-409, Plenum Press, New York, (1995).

Finch et al., "Evolutionary Perspectives on Amyloid and Inflammatory Features of Alzheimer Disease," *Neurobiology of Aging*, 17(5):809-815 (1996).

Findeis et al., "Modified peptide inhibitors of amyloid B-peptide polymerization," *Biochemistry*, 38:6791-6800 (1999).

Findeis, M. A., "Approaches to discovery and characterization of inhibitors of amyloid β-peptide polymerization," *Biochem. Biophys. Acta*, 1502(1):76-84 (2000).

Fisher et al., "Expression of the amyloid precursor protein gene in mouse oocytes and embryos," *PNAS*, 88:1779-1782 (1991).

Flanders et al., "Altered expression of transforming growth factor-β in Alzheimer's disease," *Neurology*, 45:1561-1569 (1995).

Flood et al., "An amyloid β-Protein fragment, A β [12-28J, equipotently impairs post-training memory processing when injected into different limbic system structures," *Brain Res*, 663(2):271-276 (1994).

Flood, et al, "Topography of a binding site for small amnestic peptides deduced from structure-activity studies: Relation to amnestic effect of amyloid B protein," *PNAS*, 91:380-384 (1994).

Fonseca et al., "The Presence of Isoaspartic Acid in β-Amyloid Plaques Indicates Plaque Age," *Experimental Neurology*, 157(2):277-288 (1999).

Foote et al., "Antibody Framework Residues Affecting the Conformation of the Hypervariable Loops," *J. Mol. Biol.*, 224:487-499 (1992).

Frautschy et al., "Effects of injected Alzheimer β-amyloid cores in rat brain," *PNAS*, 88:8362-8366 (1991).

Frazer et al., "Immunoglobulins: Structure and Function," chapter 3, pp. 37-74 from *Fundamental Immunology, fourth edition*, W.E. Paul, eds., Lippincott-Raven publishers, Philadelphia (1999).

Frenkel et al., "Generation of auto-antibodies towards Alzheimer's disease vaccination" *Vaccine*, 19:2615-2619 (2001).

Frenkel et al., "High affinity binding of monoclonal antibodies to the sequential epitope EFRH of β-amyloid peptide is essential for modulation of fibrillar aggregation," *J. of Neuroimmunology*, 95:136-142 (1999).

Frenkel et al., "Immunization against Alzheimer's β-amyloid plaques via EFRH phage administration," *PNAS*, 97:11455-11459 (2000).

Frenkel et al., "N-terminal EFRH sequence of Alzheimer's β-amyloid peptide represents the epitope of its anti-aggregating antibodies," *J. of Neuroimmunology*, 88:85-90 (1998).

Frenkel, et al., "Modulation of Alzheimer's β-amyloid neurotoxicity by site-directed single chain antibody," *J. of Neuroimmunology*, 106:23-31 (2000).

Frenkel et al., "Reduction of β-amyloid plaques in brain of transgenic mouse model of Alzheimer's disease by EFRH-phage immunization," *Vaccine*, 21(11-12):1060-1065 (2003).

Frenkel et al., "Towards Alzheimer's β-amyloid vaccination," *Biologicals*, 29(3-4):243-247 (2001).

Friedland et al., "Development of an anti-Aβ monoclonal antibody for in vivo imaging of amyloid angiopathy in Alzheimer's disease," *Mol. Neurology*, 9:107-113 (1994).

Friedland, et al., "Neuroimaging of Vessel Amyloid in Alzheimer's Disease," in *Cerebrovascular Pathology in Alzheimer's Disease*, eds. de la Torre and Hachinski, New York Academy of Sciences, New York, New York (1997).

Furlan et al., "Vaccination with amyloid-β peptide induces autoimmune encephalomyelitis in C57/BL6 mice," *Brain*, 126:285-291 (2003).

Games et al., "Alzheimer-type neuropathology in transgenic mice overexpressing V717F β-amyloid precursor protein," *Nature*, 373(6514):523-527 (1995).

Games et al., "Prevention and Reduction of AD-type Pathology in PDAPP Mice Immunized with $A\beta_{1-42}$," *Annals of the New York Academy of Science*, 920:274-284 (2000).

Gandy et al., "Amyloidogenesis in Alzheimer's disease: some possible therapeutic opportunities," *TiPS*, 13:108-113 (1992).

Gardella et al., "Intact Alzheimer amyloid precursor protein (APP) is present in platelet membranes and is encoded by platelet mRNA," *Biochem. Biophys. Res. Comm.*, 173:1292-1298 (1990).

Gaskin et al., "Human antibodies reactive with beta-amyloid protein in Alzheimer's disease," *J. Exp. Med.*, 177:1181-1186 (1993).

Geddes, "N-terminus truncated β-amyloid peptides and C-terminus truncated secreted forms of amyloid precursor protein: distinct roles in the pathogenesis of Alzheimer's disease," *Neurobiology of Aging*, 20:75-79 (1999).

Gelinas et at, "Immunotherapy for Alzheimer's disease," *PNAS*, 101(suppl. 2):14657-14662 (2004).

Genbank Accession No. AAB48800, "Anti-DNA immunoglobulin light chain IgG [Mus musculus]," Sep. 14, 2001.

Genbank Accession No. CAA46659, "IgE antibody light chain(VJ)," Jun. 15, 1993.

Genbank Accession No. X65775.1, "M.musculus DNA for IgE antibody light chain (VJ)," Jun. 15, 1993.

Genbank Accession No. AAD26773, "Immunoglobulin heavy chain VH3609-JH3 region [Mus musculus]," Apr. 22, 1999.

Ghiso et al., "Epitope map of two polyclonal antibodies that recognize amyloid lesions in patients with Alzheimer's disease" *Biochem. J.*, 282 (Pt 2):517-522 (1992).

Giulian et al., "Specific domains of β-amyloid from Alzheimer plaque elicit neuron killing in human microglia," *J Neurosci.*, 16 (19):6021-6037 (1996).

Giulian, et al., "The HHQK Domain of b-Amyloid Provides a Structural Basis for the Immunopathology of Alzheimer's Disease," *J. Biol. Chem..*, 273:29719-29726 (1998).

Glenn et al., "Skin immunization made possible by cholera toxin," *Nature*, 391:851 (1998).

Glenner et al., "Alzheimer's Disease and Downs Syndrome: Sharing of A Unique Cerebrovascular Amyloid Fibril Protein," *Biochem. Biophys. Res. Comm.*, 122(3): 1131-1135 (1984).

Glenner et al., "Alzheimer's Disease: Initial Report of the Purification and Characterization of a Novel Cerebrovascular Amyloid Protein," *Biochem. Biophys. Res. Comm.*, 120(3): 885-890 (1994).

Goate et al., "Segregation of a missense mutation in the amyloid precursor protein gene with familial Alzheimer's disease," *Nature*, 349:704-706 (1991).

Goldfarb et al., "The Transmissible Spongiform Encephalopathies," *Ann. Rev. Med.*, 46:57-65 (1995).

Goldsby et al., "Vaccines," Chapter 18 from *Immunology, 4th Edition*, W.H. Freeman and Company, New York, pp. 449-465 (2000).

Goldsteins et al., "Goldsteins ei al., Exposure of cryptic epitopes on transthyretin only in amypoid and in amyloidogenic mutants," *PNAS*, 96:3108-3113 (1999).

Gong et al., "Alzheimer's disease-affected brain: presence of oligomeric Aβ ligands (ADDLs) suggests a molecular basis for reversible memory loss," *PNAS*, 100(18):10417-10422 (2003).

Gonzales-Fernandez et al., "Low antigen dose favors selection of somatic mutants with hallmarks of antibody affinity maturation," *Immunology*, 93:149-153 (1998).

Gorevic et al., "Ten to fourteen residue peptides of Alzheimer's disease protein are sufficient for amyloid fibril formation and its characteristic X ray diffraction pattern" *Biochem. and Biophy. Res. Commun.*, 147(2):854-862 (1987).

Gortner, *Outlines of Biochemistry*, pp. 322-323, John Wiley & Sons, Inc., New York (1949).

Gozes et al., "Neuroprotective strategy for Alzheimer disease: Intranasal administration of a fatty neuropeptide," *PNAS*, 93:427-432 (1996).

Gravina et al., "Amyloid β Protein (Aβ) in Alzheimer's Disease," *J. Biol. Chem.*, 270(13):7013-7016 (1995).

Greenberg et al., "Alzheimer disease's double-edged vaccine," *Nat. Med.*, 9(4):389-390 (2003).

Grubeck-Loebenstein, et al., "Immunization with β-amyloid: could T-cell activation have a harmful effect?", *TINS*, 23:114 (2000).

Gupta et al., "Differences in the immunogenicity of native and formalized cross reacting material (CRM197) of diptheria toxin in mice and guinea pigs and their implications on the development and control of diphtheria vaccine based on CRMs," *Vaccine*, 15(12/13): 1341-1343 (1997).

Haass et al. "Amyloid beta-peptide is produced by cultured cells during normal metabolism," *Nature*, 359(6393):322-325 (1992).

Haass et al., "Protofibrils, the unifying toxic molecule of neurodegenerative disorders?," *Nature Neuroscience*, 4(9):859-860 (2001).

Haass, C., "New hope for Alzheimer disease vaccine," *Nat Med.*, 8(11):1195-1196 (2002).

Haga et al., "Synthetic Alzheimer amyloid β/A4 peptides enhance production of complement C3 component by cultured microglial cells," *Brain Research*, 601:88-94 (1993).

Hanan and Solomon, "Inhibitory effect of monoclonal antibodies on Alzheimer's β-amyloid peptide aggregation," *Int. J. Exp. Clin. Invest.*, 3:130-133 (1996).

Hanes et al., "New advances in microsphere-based single-dose vaccines," *Advanced Drug Delivery Reviews*, 28: 97-119 (1997).

Hardy, "Amyloid, the presenilins and Alzheimer's disease," *TINS*, 20(4): 154-159 (1997).

Hardy, John, "New Insights into the Genetics of Alzheimer's Disease," *Annals of Med.*, 28:255-258 (1996).

Harigaya, et al., "Modified amyloid β protein ending at 42 or 40 with different solubility accumulates in the brain of Alzheimer's disease," *Biochem. Biophys, Res. Comm.*, 211:1015-1022 (1995).

Harrington et al., "Characterization of an epitope specific to the neuron-specific isoform of human enolase recognized by a monoclonal antibody raised against a synthetic peptide corresponding to the C-terminus of β/A4-protein," *Biochimica Biophysica Acta*, 1158:120-128 (1993).

Hazama, et al., "Intranasal Immunization Against Herpes Simplex Virus Infection by Using a Recombinant Glycoprotein D Fused With Immunomodulating Proteins, the B Subunit of *Escherichia coli* Heat-Labile Enterotoxin and Interleukin-2," *Immunology*, 78:643-649 (1993).

He et al., "Humanization and pharmacokinetics of a monoclonal antibody with specificity for both E- and P-selectin," *J. Immunol*, 160:1029-1035 (1998).

Helmuth, "Further Progress on a β-Amyloid Vaccine," *Science*, 289:375 (2000).

Herlyn et al., "Monoclonal antibodies in cell-mediated cytotoxicity against human melanoma and colorectal carcinoma," *Eur. J. Immunol.*, 9:657-659 (1979).

Hilbich et al., "Aggregation and secondary structure of synthetic amyloid βA4 peptides of Alzheimer's disease," *J. Mol. Biol.*, 218:149-163 (1991).

Hilbich et al., "Substitutions of hydrophobic amino acid reduce the amyloidogenicity of Alzheimer's disease βA4 peptides" *J. Mol. Biol.*, 228:460-473 (1992).

Hilbich et al., "Human and rodent sequence analogs of Alzheimer's amyloid βA4 share similar properties and can be solubilized in buffers of pH 7.4," *Eur. J. Biochem.*, 201:61-69 (1991).

Hock et al., "Antibodies against β-Amyloid Slow Cognitive Decline in Alzheimer's Disease," *Neuron*, 38:542-554 (2003).

Hock et al., "Generation of antibodies specific for β-amyloid by vaccination of patients with Alzheimer disease," *Nat. Med.*, 8(11):1270-1275 (2002).

Holtzman et al., "Aβ immunization and anti-Aβ antibodies: potential therapies for the prevention and treatment of Alzheimer's disease," *Advanced Drug Delivery Reviews*, 54:1603-1613 (2002).

Hsiao et al., "Correlative Memory Deficits, Aβ Elevation, and Amyloid Plaques in Transgenic Mice," *Science*, 274: 99-102 (1996).

Huberman et al., "Correlation of cytokine secretion by mononuclear cells of Alzheimer's patients and their disease stage," *J. Neuroimmunolooy*, 52:147-152 (1994).

Human Immunology & Cancer Program brochure, from The University of Tennessee Medical Center/Graduate School of Medicine, Knoxville, Tennessee (publication date unknown).

Hyman et al., "Molecular Epidemiology of Alzheimer's Disease," *N. E. J. Medicine*, 333(19):1283-1284 (1995).

Ikeda, et al., "Immunogold labeling of cerebrovascular and neuritic plaque amyloid fibrils in Alzheimer's disease with an anti-β protein monoclonal antibody," *Lab. Invest.*, 57:446-449 (1987).

Irizarry et al., "Aβ Deposition Is Associated with Neuropil Changes, but not with Overt Neuronal Loss in the Human Amyloid Precursor Protein V717F (PDAPP) Transgenic Mouse," *J. Neuroscience*, 17(18):7053-7059 (1997).

Irizarry et al., "Alzheimer disease therapeutics," *J. Neuropathol. Exp. Neurol.*, 60(10):923-928 (2001).

Itagaki et al., "Relationship of microglia and astrocytes to amyloid deposits of Alzheimer's disease," *J. Neuroimmunology*, 24:173-182 (1989).

Iwatsubo et al., "Visualization of Aβ42(43) and Aβ40 in Senile Plaques with End-Specific Aβ Monoclonals: Evidence That an Initially Deposited Species Is Aβ 42(43)," *Neuron*, 13:45-53 (1994).

Jahrling et al., "Opsonization of Alphaviruses in Hamsters," *J. Medical Virology*, 12:1-16 (1983).

Jakes et al., "Characterisation of an Antibody Relevant to the Neuropathology of Alzheimer Disease," *Alzheimer Disease and Associated Disorders*, 9(1):47-51 (1995).

Jansen et al., "Immunotoxins: Hybrid Molecules Combining High Specificity and Potent Cytotoxicity," *Immun. Rev.*, 62: 185-216 (1982).

Janus et al., "A beta peptide immunization reduces behavioural impairment and plaques in a model of Alzheimer's disease," *Nature*, 408(6815):979-982 (2000).

Janus et al., "Transgenic mouse models of Alzheimer's Disease," *Physiol. Behav.*, 73(5):873-886 (2001).

Jen, et al., "Preparation and purification of antisera against different regions or isoforms of b-amyloid precursor protein," *Brain Research Protocols*, 2:23-30 (1997).

Joachim et al., "Antibodies to Non-beta Regions of the Beta-amyloid Precursor Protein Detect a Subset of Senile Plaques," *Am. J. of Pathology*, 138:373-384 (1991).

Jobling et al., "Analysis of structure and function of the B subunit of cholera toxin by the use of site-directed mutagenesis," *Molecular Microbiology*, 5(7):1755-1767 (1991).

Johnson-Wood et al., "Amyloid precursor protein processing and $A\beta_{42}$ deposition in a transgenic mouse model of Alzheimer disease " *PNAS*, 94:1550-1555 (1997).

Johnstone et al., Nuclear and Cytoplasmic Localization of the β-Amyloid Peptide (1-43) in Transfected 293 Cells, *Biochem. Biophys. Res. Comm.*, 220:710-718 (1996).

Jorbeck et al., "Artificial *Salmonella* Vaccines: *Salmonella typhimurium* O-antigen-Specific Oligosaccharide-Protein Conjugates Elicit Opsonizing Antibodies that Enhance Phagocytosis," *Infection and Immunity*, 32(2):497-502 (1981).

Jung et al., "Alzheimer's Beta-amyloid Precursor Protein Is Expressed on the Surface of Immediately Ex Vivo Brain Cells: a Flow Cytometric Study," *J. Neurosci. Res.*, 46:336-348 (1996).

Kalaria, R. N., "Serum amyloid P and related molecules associated with the acute-phase response in Alzheimer's disease," *Res. Immunology*, 143:637-641 (1992).

Katzav-Gozansky et al., "Effect of monoclonal antibodies in preventing carboxypeptidase A aggregation," *Biotechnol. Appl. Biochem.*, 23:227-230 (1996).

Kawabata et al., "Amyloid plagues, neurofibrillary tangles and neuronal loss in brains of transgenic mice overexpressing a C-terminal fragment of human amyloid precursor protein," *Nature*, 354:476-478 (1991).

Kayed et al., "Conformational Transitions of Islet Amyloid Polypeptide (IAPP) in Amyloid Formation In Vitro" *J. Mol. Biol.*, 287:781-796 (1999).

Kelly, J. W., "Alternative conformations of amyloidogenic proteins govern their behavior," *Current Opinion in Structural Biology*, 6:11-17 (1996).

Kettleborough et al., "Humanization of a mouse monoclonal antibody by CDR-grafting: the importance of framework residues on loop conformation," *Protein Engineering*, 4(7):773-783 (1991).

Kida, et al., "Early amyloid-β deposits show different immunoreactivity to the amino- and carboxy-terminal regions of b-peptide in Alzheimer's disease and Down's syndrome brain," *Neuroscience Letters*, 193:105-108 (1995).

Klein et at., "Targeting small Aβ oligomers: the solution to an Alzheimer's disease conundrum?," *Trends in Neurosciences*, 24(4):219-224 (2001).

Kofler et al., "Mechanism of Allergic Cross-Reactions-III. cDNA Cloning and Variable-Region Sequence Analysis of Two IgE Antibodies Specific for Trinitrophenyl," *Mol. Immunology*, 29(2):161-166 (1992).

Konig et al., "Development and Characterization of a Monoclonal Antibody 369.2B Specific for the Carboxyl-Terminus of the βA4," *Annals of NY Acad. Sci.*, 777:344-355 (1996).

Kotilinek et al., "Reversible memory loss in a mouse transgenic model of Alzheimer's disease," *J. Neurosci.*, 22(15):6331-6335 (2002).

Koudinov et al., "The soluble form of Alzheimer's amyloid beta protein is complexed to high density lipoprotein 3 and very high density lipoprotein in normal human plasma," *Biochem. & Biophys. Res. Comm*, 205:1164-1171 (1994).

Kovács et al., "Mutations of the Prion Protein Gene Phenotypic Spectrum," *J. Neurol.*, 249:1567-1582 (2002).

Krishnan et al., "Correlation Between the Amino Acid Position of Arginine in VH-CDR3 and Specificity for Native DNA Among Autoimmune Antibodies," *J. Immunol.*, 157(6):2430-2439 (1996).

Kuo et al., "High levels of circulating Abeta42 are sequestered by plasma proteins in Alzheimer's disease," *Biochem. Biophys. Res. Comm.*, 257(3):787-791 (1999).

Lambert et al., "Diffusible, nonfibrillar ligands derived from Aβ1-42 are potent central nervous system neurotoxins" *PNAS*, 95:6448-6453 (1998).

Lambert et al., "Vaccination with soluble Aβ oligomers generates toxicity-neutralizing antibodies," *J. Neurochem.*, 79:595-605 (2001).

Lampert-Etchells et al., "Regional Localization of Cells Containing Complement C1q and C4 mRNAs in the Frontal Cortex During Alzheimer's Disease," *Neurodegeneration*, 2:111-121 (1993).

Landolfi et al., "The Integrity of the Ball-and Socket Joint Between V and C Domains Is Essential for Complete Activity of a Humanized Antibody," *J. Immunology*, pp. 1748-1754 (2001).

Langer, "New Methods of Drug Delivery," *Science*, 249:1527-1532 (1990).

Lannfelt et al., "Alzheimer's disease: molecular genetics and transgenic animal models, " *Behavioural Brain Res.*, 57:207-213 (1993).

Lansbury, Peter T., "Inhibition of amyloid formation: a strategy to delay the onset of Alzheimer's disease," *Curr. Ops. in Chemical Biology*, 1:260-267 (1997).

Lee et al., "Aβ immunization: Moving Aβ peptide from brain to blood," *PNAS*, 98(16):8931-8932 (2001).

Lemere et al., "Mucosal Administration of Aβ Peptide Decreases Cerebral Amyloid Burden In Pd-App Transgenic Mice," *Society for Neuroscience Abstracts*, 25(part )I, Abstract 519.6, 29th Annual Meeting, (Oct. 23-28, 1999).

Lemere, et al., "Nasal Aβ treatment induces anti-Aβ antibody production and decreases cerebral amyloid burden in PD-APP mice," *Annals of the NY Acad. Sci.*, 920:328-331 (2000).

Lemere et al., "Intranasal immunotherapy for the treatment of Alzheimer's disease: *Escherichia coli* LT and LT(R192G) as mucosal adjuvants," *Neurobiology of Aging*, 23(6):991-1000 (2002).

Leverone of al., "Aβ1-15 is less immunogenic than Aβ-40/42 for intranasal immunization of wild-type mice but may be effective for 'boosting'," *Vaccine*, 21:2197-2206 (2003).

Levitt, M., "Molecular dynamics of native protein," *J. Mol . Biol.*, 168:595-620 (1983).

Levy et al., "Immunization for Alzheimer's disease: A shot in the arm or a whiff?," *American Neurological Assoc*, 48:553-554 (2000).

Li et al., "Thermal Stabilization of Carboxypeptidase A as a Function of PH and Ionic Milieu," *Biochem. Mol. Biol. Int.*, 43(3):601-611 (1997).

Livingston et al., "The Hepatitis B Virus-Specific CTL Responses Induced in Humans by Lipopeptide Vaccination Are Comparable to Those Elicited by Acute Viral Infection," *J. Immunol.*, 159:1383-1392 (1997).

Lopez et al., "Serum auto-antibodies in Alzheimer's disease," *Acta. Neurol. Scand.*, 84:441-444 (1991).

Lue et al., "Soluble β-amyloid Peptide Concentration as a Predictor of Synaptic Change in Alzheimer's Disease," *Am. J. Pathol.*, 155:853-562 (1999).

Maggio et al., "Brain Amyloid—A Physicochemical Perspective," *Brain Pathology*, 6:147-162 (1996).

Majocha et al., "Development of a Monoclonal Antibody Specific for β/A4 Amyloid in Alzheimer's Disease Brain for Application to In Vitro Imaging of Amyloid Angiopathy," *The J. of Nuclear Med.*, 33:2184-2189 (1992).

Mak, et al., "Polyclonals to b-amyloid (1-42) identify most plaque and vascular deposits in Alzheimer cortex, but not striatum," *Brain Research*, 667:138-142 (1994).

Mann, et al., "Amyloid β protein (Aβ) deposition in chromosome 14-linked Alzheimer's disease: Predominance of $A\beta_{42(43)}$," *Annals of Neurology*, 40:149-156 (1996).

Mann, et al., "The extent of amyloid depsoition in brain in patients with Down's syndrome does not depend upon the apolipoprotein E genotype," *Neuroscience Letters*, 196:105-108 (1995).

Marshall, E., "Gene Therapy's Growing Pains," *Science*, 269:1050-1055 (1995).

Masliah et al., "β-Amyloid peptides enhance α-synuclein accumulation and neuronal deficits in a transgenic mouse model linking Alzheimer's disease and Parkinson's disease," *PNAS*, 98(21):12245-12250 (2001).

Masliah et al., "Comparison of Neurodegenerative Pathology in Transgenic Mice Overexpressing V717F β-Amyloid Precursor Protein and Alzheimer's Disease," *J. Neuroscience*, 16(18):5795-5811 (1996).

Masters et al., "Amyloid Plaque core protein in Alzheimer Disease and Down Syndrome," *PNAS*, 82:4245-4249 (1985).

Mattson, "Cellular actions of beta-amyloid precursor protein and its soluble and fibrillogenic derivatives," *Physiol Rev.*, 77(4):1081-132 (1997).

Mattson et al., "Good and bad amyloid antibodies," *Science*, 301(5641):1845-1849 (2003).

McGee et al., "The encapsulation of a model protein in poly (D, L lactide-co-glycolide) microparticles of various sizes: an evaluation of process reproducibility," *J. Micro. Encap.*, 14(2):197-210 (1997).

McGeer, et al., "Immunohistochemical localization of beta-amyloid precursor protein sequences in Atzheimer and normal brain tissue by light and electron microscopy," *J. of Neuroscience Res.*, 31:428-442 (1992).

McLaurin et al., "Therapeutically effective antibodies against amyloid-β peptide target amyloid-βresidues and 4-10 and inhibit cytotoxicity and fibrillogenesis," *Nat Med.*, 8(11):1263-1269 (2002).

McLean et al., "Soluble pool of Aβ amyloid as a determinant of severity of neurodegeneration in Alzheimer's disease," *Amer. Neurological Assoc*, 46:860-866 (1999).

McNeal et al., "Stimulation of local immunity and protection in mice by intramuscular immunization with triple- or double-layered rotavirus particles and QS-21," *Virology*, 243:158-166 (1998).

Meda et al., "Activation of microglial cells by β-amyloid protein and interferon-γ," *Nature*, 374:647-650 (1995).

Mena, et al., "Monitoring pathological assembly of tau and β-amyloid proteins in Alzheimer's disease," *Acta Neuropathol.*, 89:50-56 (1995).

Merluzzi, et al., "Humanized antibodies as potential drugs for therapeutic use," *Adv Clin Path.*, 4(2):77-85 (2000).

Miller et al., "Antigen-driven Bystander Suppression after Oral Administration of Antigens," *J. Exp. Med.*, 174:791-798 (1991).

Monsonego et al., "Immune hyporespoinsiveness to amyloid β-peptide in amyloid precursor protein transgenic mice: Implications for the pathogenesis and treatment of Alzheimer's disease," *PNAS*, 98(18):10273-10278 (2001).

Monsonego et al., "Increased T cell reactivity to amyloid β protein in older humans and patients with Alzheimer's disease," *J. Clin. Invest.*, 112(3):415-422 (2003).

Monsonego et al., "Immunotherapeutic approaches to Alzheimer's disease," *Science*, 302(5646):834-838 (2003).

Morgan, et al., "A beta peptide vaccination prevents memory loss in an animal model of Alzheimer's disease," *Nature*, 408(6815):982-985 (2000).

Mori et al., "Mass Spectrometry of Purified Amyloid β Protein in Alzheimer's Disease," *J. Biol. Chem.*, 267(24):17082-17088 (1992).

Morris, et al., "The Consortium to Establish a registry for Alzheimer's Disease (CERAD)," *Neurology*, 39:1159-1165 (1989).

Munch et al., "Potentional neurotoxic Inflammatory response to Aβ vaccination in humans," *J. Neural Transm.*, 109:1081-1087 (2002).

Munson eds., *Principals of Pharmacology: Basic Concepts & Clinical Applications*, pp. 47-48, Chapman & Hall, New York, New York (1995).

Murphy et al., "Development of a Monoclonal Antibody Specific for the COOH-Terminal of β-Amyloid 1-42 and Its Immunohistochemical Reactivity in Alzheimer's Disease and Related Disorders," *Am. J. Pathology*, 144(5):1082-1088 (1994).

Mutschler et al., *Drug Actions: Basic Principles and Therapeutic Aspects* pp. 7, 11-12, Medpharm Scientific Publishers, Stuttgart, Germany (1995).

Nakamura et al., "Histopathological studies on senile plaques and cerebral amyloid angiopathy in aged cynomologus monkeys," *Exp. Anim.*, 43:711-718 (1995).

Nakamura, et al., "Carboxyl end-specific monoclonal antibodies to amyloid β protein (Aβ) subtypes (Aβ40 and Aβ42(43) differentiate Ab in senile plaques and amyloid angiopathy in brains of aged cynomolgus monkeys," *Neuroscience Letters*, 201:151-154 (1995).

Nakayama et al., "Histopathological studies of senile plaques and cerebral amyloidosis in cynomolgus monkeys," *J. of Med. Primatology*, 27:244-252 (1998).

Nalbantoglu, J., "Beta-amyloid protein in Alzheimer's disease," *Can. J. Neurol. Sci.*, 18(3 suppl.):424-427 (1991), abstract only.

Naslund et al., "Correlation between elevated levels of amyloid β peptide in the brain and cognitive decline," *J. Am. Med. Assoc.*, 283:1571 (2000).

Nathanson et at., "Bovine Spongiform Encephalopathy (BSE): Causes and Consequences of a Common Source Epidemic," *Am. J. Epidemiol.*, 145(11):959-969 (1997).

New York Times National, "Anti-Inflammatory Drugs May Impede Alzheimer's," (Feb. 20, 1994).

Newcombe et al., "Solubility characteristics of isolated amyloid fibrils," *Biochim. Biophys. Acta.* 104:480-486 (1965).

Ngo et al., "Computational Complexity, Protein Structure Prediction, and the Levinthal Paradox," pp. 492-495 from Chapter 14 of *The Protein Folding Problem and Tertiary Structure Prediction*, Merz et al., eds., Birkhauser Boston (1994).

Nicoll et al., "Neuropathology of human Alzheimer's disease after immunization with amyloid-β peptide: a case report," *Nature Medicine*, 9(4):448-452 (2003).

Niemann, "Transgenic farm animals get off the ground;" *Transgenic Research*, 7:73-75 (1998).

Novotny et al., "Structural invariants of antigen binding: Comparison of immunoglobulin $V_L$-$V_H$ and $V_L$-$V_L$ domain dimmers," *PNAS*, 82:4592-4596 (1985).

Orkin et al., *Report and Recommendations of the Panel to Assess the NIH Investment in Research on Gene Therapy*, Dec. 7, 1995.

Orlandi et al., "Cloning immunoglobulin variable domains for expression by the polymerase chain reaction," *PNAS*, 86:3833-3837 (1989).

Paganetti et al., "Amyloid precursor protein truncated at any of the γ-secretase sites is not cleaved to βamyloid," *J. Neurosci. Res.*, 46(3):283-293 (1996).

Palha et al., "Antibody recognition of amyloidogenic transthyretin variants in serum of patients with familial amyloidiotic polyneuropathy," *J. Mol. Med.*, 7:703-707 (2001).

Pallitto et al., "Recognition sequence design for peptidyl modulators of β-amyloid aggregation and toxicity," *Biochemistry*, 38(12):3570-3578 (1999).

Pan et al., "Antibodies to β-Amylold Decrease the Blood-to-Brain Transfer of β-Amyloid Peptide," *Exp. Biol. Med.*, 227(8):609-615 (2002).

Panka et al., "Variable region framework differences result in decreased or increased affinity of variant anti-digoxin antibodies," *PNAS*, 85:3080-3084 (1998).

Pardridge et al., "Chimeric peptides as a vehicle for peptide pharmaceutical delivery through the blood-brain barrier," *Biochem. Biophys. Res. Comm.*, 146:307-313 (1987).

Paresce et al., "Microglial cells influence aggregates of the Alzheimer's disease amyloid beta-protein via a scavenger receptor," *Neuron*, 17:553-565 (Sep. 1996).

Paul et al., "Transdermal immunization with large proteins by means of ultradeformable drug carriers," *Eur. J. Immunol.*, 25: 3521-3524 (1995).

Paul, W. E., eds., *Fundamental Immunology*, Third Edition, pp. 292-295, Raven Press, New York (1993).

PCT Search Report of Dec. 14, 2004 for application PCT/US04/02856.

Persson et al., "IgG subclass-associated affinity differences of specific antibodies in humans," *J. Immunology*, 140(11):3875-3879 (1988), abstract only.

Perutz et al., "Amyloid fibers are water-filed nanotubes," *PNAS*, 99(8):5591-5595 (2002).

Peterson, et al., "Recombinant Antibodies: Alternative Strategies for Developing and Manipulating Murine-Derived Monoclonal Antibodies," *Laboratory Animal Science*, 46(1):8-14 (1996).

Pfeifer et al., "Cerebral hemorrhage after passive anti-Aβ immunotherapy," *Science*, 298(5597):1379 (2002).

Philippe, et al. "Generation of a monoclonal antibody to the carboxy-terminal domain of tau by immunization with the amino-terminal domain of the amyloid precursor protein," *J. of Neuroscience Res.*, 46:709-719 (1996).

Poduslo et al., "Permeability of proteins at the blood-brain barrier in the normal adult mouse and double transgenic mouse model of Alzheimer's disease," *Neurobiol. Dis.*, 8(4):555-567 (2001).

Prieels et al., "Synergistic adjuvants for vaccines," *Chemical Abstracts*, 120(8):652, col. 1, abstract 86406t (1994).

Prusiner et al., "Ablation of the prion protein (PrP) gene in mice prevents scrapie and facilitates production of anti-PrP antibodies," *PNAS*, 90:10608-10612 (1993).

Queen et al., "A humanized antibody that binds to the interleukin 2 receptor," *PNAS*, 86:10029-10033 (1989).

Quon et al, "Formation of β-Amyloid protein deposits in brains of transgenic mice," *Nature*, 352:239-241 (1991).

Racke et al., "Exacerbation of Cerebral Amyloid Angiopathy-Assoiclated Microhemorrhage in Amyloid Precursor Protein Trasngenic Mice by Immunotherapy Is Dependent on Antibody Recognition of Deposited Forms of amyloid β," *J. Neurosci.*, 25(3):629-636 (2005).

Ragusi et al., "Redistribution of Imipramine from Regions of the Brain Under the Influence of Circulating Specific Antibodies," *J. Neurochem.*, 70(5):2099-2105 (1998).

Raso, "Immunotherapy of Alzheimer's Disease," *Immunotherapy Weekly*, Abstract (Apr. 2, 1998).

Raso, V.A., Grant application # 1 R43 AGI 5746-01 (non-redacted version), "Immunotherapy of Alzheimer's Disease" (publication date unknown).

Raso, V.A., Grant application # 1 R43 AGI 5746-01 (redacted version), "Immunotherapy of Alzheimer's Disease" (publication date unknown).

Research Corporation Technology News, "THP and SangStat Partner to Develop Humanized Polyclonal Antibody Drugs," Nov. 11, 2002.

"Researchers Develop Blood Test to Diagnose Alzheimer's-Type Changes in Mice," downloaded from www.businesswire.com on Dec. 15, 2004.

Rogers et al., "Complement activation by β-amyloid in Alzheimer Disease," *PNAS*, 89:1-5 (1992).

Rossor et al., "Alzheimer's Disease Families with Amyloid Precursor Protein Mutations," *Annals of New York Academy of Sciences*, 695:198-202 (1993).

Rudikoff et al., "Single amino acid substitution altering antigen-binding specificity," *PNAS*, 79:1979-1983 (1982).

Rudinger, "Characteristics of the Amino Acids as Components of a Peptide Hormone Sequence," in *Peptide Hormones*, J.A. Parson, ed. University Park Press, Baltimore, pp. 1-7 (1976).

Saido et al., "Spatial Resolution of Fodrin Proteolysis in Postischemic Brain," *J. Biol. Chem.*, 268(33):25239-25243 (1993).

Saido et al., "Spatial Resolution of the Primary β-Amyloidogenic Process Induced in Postischemic Hippocampus," *J. Biol. Chem.*, 269(21):15253-15257 (1994).

Saito et al., "Vector-mediated delivery of $^{125}$I-labeled β-amyloid peptide $Ab^{1-40}$ through the blood-brain barrier and binding to Alzheimer disease amyloid of the $A\beta^{1-40}$ vector complex," *PNAS*, 92:10227-10231 (1995).

Saitoh, N. et al., "Immunological analysis of Alzheimer's disease using anti- β-protein monoclonal antibodies," *Sapporo Med. J.*, 60:309-320 (1991).

Sasaki et al., "Human choroid plexus is an uniquely involved area of the brain in amyloidosis: a histochemical, immunohistochemical and ultrastructural study," *Brain Res.*, 755:193-201 (1997).

Schenk et al, "Immunization with amyloid-β attenuates Alzheimer-disease-like pathology in the PDAPP mouse," *Nature*, 400:173-177 (1999).

Schenk et al., "Therapeutic Approaches Related to Amyloid-β Peptide and Alzheimer's Disease," *J. Med. Chem.*, 38(21):4141-4154 (1995).

Schenk et al., "β-peptide immunization," *Arch. Neurol.*, 57:934-936 (2000).

Schenk et al., "Immunotherapy with beta-amyloid for Alzheimer's disease: a new frontier," *DNA Cell Biol.*, 20(11):679-81 (2001).

Schenk, D., "Amyloid-β immunotherapy for Alzheimer's disease: the end of the beginning," *Nature Reviews*, 3:824-828 (2002).

Schmid, R. E., "Study suggest Alzheimer vaccine fix," from www.msnbc.com/news, pp. 1-5 (2002).

Schwarzman et al., "Transthyretin sequesters amyloid β protein and prevents amyloid formation," *PNAS*, 91:8368-8372 (1994).

Seidl et al., "Predominant $V_H$ genes expressed in innate antibodies are associated with distinctive antigen-binding sites," *PNAS*, 96:2262-2267 (1999).

Sela et al, "Different roles of D-amino acids in immune phenomena," *FASEB J.* 11(6):449-456 (1999).

Selkoe, "Alzheimer's Disease: A Central Role for Amyloid," *J. Neuropathol. Exp, Neurol.*, 53(5): 438-447 (1994).

Selkoe, "Physiological production of the β-amyloid protein and the mechanism of Alzheimer's disease," *Trends in Neurosciences*, 16(10): 403-409 (1993).

Selkoe, "The cell biology of beta-amyloid precursor protein and presenilin in Alzheimer's disease," *Trends Cell Biol.*, 8(11):447-53 (1998).

Selkoe, D.J., "Imaging Alzheimer's Amyloid," *Nat. Biotech.*, 18:823-824 (2000).

Selkoe, Dennis J., "Alzheimer's Disease: Genotypes, Phenotype, and Treatments," *Science*, 275:630-631 (1997).

Selkoe, Dennis J., "Amyloid Protein and Alzheimer's Disease . . . ," *Scientific American*, pp. 68-78 (1991).

Selkoe, Dennis J., "In the Beginning . . . ," *Nature*, 354:432-433 (1991).

Selkoe, Dennis J., "The Molecular pathology of Alzheimer's Disease," *Neuron*, 6:487.498 (1991).

Selkoe, D. J., "Alzheimer's disease is a synaptic failure," *Science*, 298(5594):789-791 (2002).

Sergeant et al., "Truncated beta-amyloid peptide species in pre-clinical Alzheimer's disease as new targets for the vaccination approach," *J. Neurochem.*, 85(6):1581-1591 (2003).

Seubert et al., "Isolation and quantification of soluble Alzheimer's β-peptide from biological fluids," *Nature*, 359: 325-327 (1992).

Shiosaka, S., "Attempts to make models for Alzheimer's disease," *Neuroscience Res.*, 13:237-255 (1992).

Sigmund, "Viewpoint: Are Studies in Genetically Altered Mice Out of Control,"*Aderioscler Thromb Vasc Biol.*, 20:1425-1429 (2000).

Sigurdsson et al., "A safer vaccine for Alzheimer's disease?," *Neurobiology of Aging*, 23:1001-1008 (2002).

Sigurdsson et al., "Anti-priori antibodies for prophylaxis following prion exposure in mice," *Neurosciences Letters*, 336:185-187 (2003).

Sigurdsson et al., "Immunization Delays the Onset of Prion Disease in Mice," *American Journal of Pathology*, 161:13-17 (2002).

Sigurdsson, et al., "In vivo reversal of amyloid-beta lesions in rat brain," *J Neuropathol Exp Neurol.*, 59(1):11-17 (2000).

Sigurdsson et al., "Immunization with a Nontoxic/Nonfibrillar Amyloid-β Homologous Peptide Reduces Alzheimer's Disease-Associated Pathology in Trasngenic Mice," *Am. J. Pathology*, 159(2):439-447 (2001).

Simmons, L., "Secondary structure of amyloid β peptide correlates with neurotoxic activity in vitro," *Molecular Pharmacology*, 45:373-379 (1994).

Singh, K. S., "Neuroautoimmunity: Pathogenic Implications for Alzheimer's Disease," *Gerontology*, 43:79-94 (1997).

Singh, V. K., "Studies of neuroimmune markers in Alzheimer's disease," *Mol. Neurobiology*, 9(1-3):73-81 (1994), abstract only.

Sinha, et al., "Recent advances in the understanding of the processing of APP to beta amyloid peptide,". *Ann N Y Acad Sci.*, 920:206-8 (2000).

Sipe, "Amyloidosis," *Annu. Rev. Biochem.*, 61:947-975 (1992).

Skolnick and Fetrow, "From genes to protein structure and function: novel applications of computational approaches in the genomic era," *Trends in Biotech*, 18(1):34-39 (2000).

Small et al., "Alzheimer's disease and Abeta toxicity: from top to bottom," *Nat Rev Neurosci.*, 2(8):595-598 (2001).

Smith et al., "The challenges of genome sequence annotation or 'The devil is in the details,'" *Nature Biotechnology*, 15:1222-1223 (1997).

Smits et al., "Prion Protein and Scrapie Susceptibility,"*Vet. Quart.*, 19(3):101-105 (1997).

Solomon and et al., "Modulation of The Catalytic Pathway of Carboxypeptidase A by Conjugation with Polyvinyl Alcohols," *Adv. Mol. Cell Biology*, 15A:33-45 (1996).

Solomon et al., "Activity of monoclonal antibodies in prevention of in vitro aggregation of their antigens," abstract from Department of Molecular Microbiology and Biotechnology, Tel Aviv University, Tel Aviv, Israel (publication date unknown).

Solomon et al., "Disaggregation of Alzheimer β-amyloid by site-directed mAb," *PNAS*, 94:4109-4112 (1997).

Solomon et al., "Monoclonal antibodies inhibit in vitro fibrillar aggregation of the Alzheimer β-amyloid peptide," *PNAS*, 93:452-455 (1996).

Solomon et al., "The Amino Terminus of the β-Amyloid Peptide Contains an Essential Epitope for Maintaining Its Solubility," from *Progress in Alzheimer's and Parkinson's Diseases*, edited by Fisher et al., Plenum Press, New York, pp. 205-211 (1995).

Solomon, A., "Pro-Rx (Protein Therapeutics)," University of Tennessee Medical Center (publication date unknown).

Solomon, B., "New Approach Towards Fast Induction of Anti β-Amyloid Peptide Immune Response," Department of Molecular Microbiology & Biotechnology, Tel-Aviv University, Ramat Aviv, Tel-Aviv, Israel (publication date unknown).

Solomon, B., "Immunological approaches as therapy for Alzhelmer's disease," *Expert Opin. Biol. Ther.*, 2(8):907-917 (2002).

Solomon, B., "Generation and brain delivery of anti-aggregating antibodies against β-amyloid plaques using phage display technology," *J. Neural Transm. Suppl.*, 62:321-325 (2002).

Solomon, B., "Immunotherapeutic strategies for prevention and treatment of Alzheimer's disease," *DNA and Cell Biology*, 20(11):697-703 (2001).

Soto et al., "Beta sheet breaker peptides inhibit fibrillogenesis in a rat brain model of amyloidosis: implications for Alzheimer's therapy," *Nature Medicine.*, 4(7):822-826 (1998).

Soto et al., "The α-helical to β-strand transition in the amino-terminal fragment of the amyloid β-peptide modulates amyloid formation," *J. Biol. Chem*, 270(7):3063-3067 (1995).

Southwick et al., "Assessment of Amyloid β protein in Cerebrospinal fluid as an Aid in the Diagnosis of Alzheimer's Disease," *J. Neurochemistry*, 66:259-265 (1996).

Spooner et al., "The generation and characterization of potentially therapeutic Aβ antibodies in mice: differences according to strain and immunization protocol," *Vaccine*, 21:290-297 (2002).

St. George-Hyslop et al., "Antibody clears senile plaques," *Nature*, 40:116-117 (1999).

Stein et al., "Lack of Neurodegeneration in Transgenic Mice Overexpressing Mutant Amyloid Precursor Protein is Associated with Increased Levels of Transthyretin and Activation of Cell Survival Pathways," *The Journal of Neuroscience*, 22(17):7380-7388 (2002).

Stern et al., "Antibodies to the β-amyloid peptide cross-react with conformational epitopes in human fibrinogen subunits from peripheral blood," *FEBS Letters*, 264(1):43-47 (1990).

Stoute et al., "A Preliminary Evaluation of a Recombinant Circumsporozoite Protein Vaccine Against *Plasmodium Falciparum Malaria*", *N. Engl. J. Med.*, 336(2):86-91 (1997).

Strbak et al., "Passive Immunization and Hypothalamic Peptide Secretion", *Neuroendocrinology*, 58:210-217 (1993).

Sturchler-Pierrat et al., "Two amyloid precursor protein transgenic mouse models with Alzheimer disease-like pathology," *PNAS*, 94: 13287-13292 (1997).

Su et al., "Intravascular infusions of soluble β-amyloid compromise the blood-brain barrier, activate CNS Glial cells and induce peripheral hemorrhage," *Brain Research*, 818:105-107 (1999).

Suo et al., "Soluble Alzhelmers β-amyloid constricts the cerebral vasculature in vivo" *Neuroscience Letters*, 257:77-80 (1998).

Szendrei, et al., "The effects of aspartic acid-bond isomerization on in vitro properties of the amyloid β-peptide as modeled with N-terminal decapeptide fragments," *Int. J. Peptide Protein Res.*, 47:289-296 (1996).

Tabaton et al., "Soluble amyloid β-protein is a marker of Alzheimer amyloid in brain but not in cerebrospinal fluid," *Biochem. and Biophys. Res. Comm.*, 200(3):1598-1603 (1994).

Tal et al., "Complete Freund's Adjuvant Immunization Prolongs Survival in Experimental Prion Disease in Mice," *Journal of Neuroscience Research*, 71:286-290 (2003).

Tan et al., "Amyloidosis " *Histopathology*, 25:403-414 (1994).

Tanaka et al., "NC-1900, an active fragment analog of arginine vasopressin, improves learning and memory deficits induced by beta-amyloid protein in rats," *European J. Pharmacology*, 352:135-142 (1998).

Teller et al., "Presence of soluble amyloid β-peptide precedes amyloid plaque formation in Down's syndrome" *Nature Medicine*, 2(1):93-95 (1996).

Tennent et al., "Serum amyloid P component prevents proteolysis of the amyloid fibrils of Alzheimer's disease and systemic amyloidosis," *PNAS*, 92:4299-4303 (1995).

Thorsett, E.D. et al., "Therapeutic approaches to Alzheimer's disease," *Curr. Op. in Chem. Biology*, 4:377-382 (2000).

Tjernberg et al., "A molecular model for Alzheimer amyloid β-peptide fibril formation," *J. Biol. Chem.*, 274(18):12619-12625 (1999).

Tjernberg et al., "Arrest of β-amyloid fibril formation by a pentapeptide ligand," *J. Biol. Chem.*, 271:8545-8548 (1996).

Tjernberg, et al, "Controlling amyloid beta-peptide fibril formation with protease-stable ligands," *J. Biol Chem.*, 272(19):12601-12605 (1997).

Town et al., "Characterization of murine immunoglobulin G antibodies against human amyloid-$\beta_{1-42}$" *Neurosci. Lett*, 307:101-104 (2001).

Trieb et al., "Is Alzheimer beta amyloid precursor protein (APP) an autoantigen? Peptides corresponding to parts of the APP sequence stimulate T lymphocytes in normals, but not in patients with Alzheimer's disease," *Immunobiology*, 191(2-3):114-115 Abstract C.37, (1994).

Tsuzuki et al., "Amyloid β protein in rat soleus in choroquine-induced myopthy using end-specific antibodies for Aβ40 and Aβ42: immunohistochemical evidence for amyloid β protein," *Neuroscience Letters*, 2002:77-80 (1995).

Van Gool et al., "Concentrations of amyloid-β protein in cerebrospinal fluid increase with age in patients free from neurodegenerative disease," *Neuroscience Letters*, 172:122-124 (1994).

Van Regenmortel et al, "D-peptides as immunogens and diagnostic reagents," *Curr. Opin. Biotechnol.*, 9(4):377-382 (1998).

Vehmas et al., "beta-Amyloid peptide vaccination results in marked changes in serum and brain Abeta levels in APPswe/PS1 DeltaE9 mice, as detected by SELDI-TOF-based ProteinChip® technology," *DNA Cell Biol.*, (11):713-721 (2001).

Velazquez et al., "Aspartate residue 7 in amyloid β-protein is critical for classical complement pathway activation: Implications for Alzheimer's disease pathogenesis," *Nature Medicine*, 3(1):77-79 (1997).

Verbeek et al., "Accumulation of Intercellular Adhesion Molecule-1 in Senile Plaques in Brain Tissue of patients with Alzheimer's Disease," *Amer. Journ. Pathology*, 144(1):104-116 (1994).

Verma et al., "Gene therapy—promises, problems and prospects," *Nature*, 389:239-242 (1997).

Vershigora A. E. *Obshchaya Immynologiya*, pp. 35, 229-231 and 152-153.

Walker et al., "Labeling of Cerebral Amyloid In Vivo with a Monoclonal Antibody," *J. Neuropath. Exp. Neurology*, 53(4):377-383 (1994).

Walsh et al., "Naturally secreted oligomers of amyloid β protein potently inhibit hippocampal long-term potentiation in vivo," *Nature*, 416(6880):535-539 (2002).

Wang et al., "The levels of soluble versus insoluble brain Aβ distinguish Alzheimer's disease from normal and pathologic aging," *Experimental Neurology*, 158:328-337 (1999).

Wang et al., "Soluble oligomers of β amyloid (1-42) inhibit long-term potentiation but not long-term depression in rate dentate gyrus," *Brain Research*, 924:133-140 (2002).

Washington University in St. Louis School of Medicine, "Study gives Clues to Working of Anti-Alzheimer Antibody," downloaded from www.medicine.wustl.edu/~wumpa/news on Dec. 15, 2004.

Weiner et al., "Nasal administration of amyloid-β peptide decreases cerebral amyloid burden in a mouse model of Alzheimer's disease," *Annals of Neurology*, 48:567-579 (2000).

Weiner et al., "Oral Tolerance: Immunologic Mechanisms and Treatment of Animal and Human Organ-Specific Autoimmune Diseases by Oral Administration of Autoantigens," *Annu. Rev. Immunol.*, 12:809-837 (1994).

Weissmann et al., "Bovine spongiform encephalopathy and early onset variant Creutzfeldt-Jakob disease," *Curr. Opin. Neurobiol.*, 7:695-700 (1997).

Weldon et al., "Neurotoxicity of Aβ Peptide: Confocal Imaging of Cellular Changes Induced by—Amyloid in Rat CNS In Vivo," *Society for Neuroscicence Abstracts*, 22(Part 1) (1996).

Wells, J. A., "Additivity of Mutational Effects in Proteins," *Biochemistry*, 29(37):8509-8517 (1990).

Wen, G.Y., "Alzheimer's Disease and Risk Factors," *J. Food Drug Analysis*, 6(2):465-476 (1998).

Wengenack et al., "Targeting Alzheimer amyloid plaques in vivo," *Nature Biotech.*, 18:868-872 (2000).

White et al., "Immunotherapy as a therapeutic treatment for neurodegenerative disorders," *J. Neurochem.*, 87(4):801-808 (2003).

Winter et al., "Humanized antibodies" *Immunology Today*, 14(6):243-246 (1996).

Wisconsin Alumni Research Foundation, "Injection of Newborn Mice with Seven Chemical Adjuvants to Help Determine Their Safety in Use in Biologicals", U.S. Govt. Res. Develop. Rep., 70(24), 56. (Publication date unknown.).

Wisniewski et al., "Alzheimer's disease and soluble A beta," *Neurobiol. Aging*, 15(2):143-52 (1994).

Wisniewski et al., "Therapeutics in Alzheimer's and Prion Diseases," *Biochemical Society Transactions*, 30(4):574-587 (2002).

Wong et al., "Neuritic Plaques and Cerebrovascular Amyloid in Alzheimer Disease are Antigenically Related" *PNAS*, 82:8729-8732 (1985).

Wood et al., "Amyloid precursor protein processing and Aβ42 deposition in a transgenic mouse model of Alzheimer disease," *PNAS*, 94: 1550-1555 (1997).

Wood et al., "Prolines and amyloidogenicily in fragments of the Alzheimer's peptide β/A4" *Biochemistry*, 34:724-730 (1995).

Wu, et al., "Drug targeting of a peptide radiopharmaceutical through the primate blood-brain barrier in vivo with a monoclonal antibody to the human insulin receptor," *J. Clin. Invest.*, 100:1804-1812 (1997).

Wu et al., "An Analysis of the Sequences of the Variable Regions of Bence Jones Proteins and Myeloma Light Chains and their Implications for Antibody Complementarity," *J. Exp. Med.*, 132-211-250 (1970).

Xu et al., "Increased incidence of anti-β-amyloid autoantibodies secreted by Epstein-Barr virus transformed B cell lines from patients with Alzheimer's disease," *Mechanisms of Ageing and Development*, 94:213-222 (1997).

Yamaguchi et al., Diffuse plaques associated with astroglial amyloid β protein, possibly showing a disappearing stage of senile plaques, *Acta Neuropathol.*, 95:217-222 (1998).

Yang et al., "Effects of Racemization on the Aggregational Properties of the Amyloid β-Peptide in Alzheimer's Disease," abstract # 255 from American Chemical Society 214th National Meeting (1997).

Younkin, "Amyloid β vaccination: reduced plaques and improved cognition," *Nature Medicine*, 7:18-19 (2001).

Zlokovic et al., "Clearance of amyloid β-peptide from brain: transport or metabolism?," *Nature Medicine*, 6(7):718-719 (2000).

Zlokovic et al., "Glycoprotein 330/megalin: probable role in receptor-mediated transport of apolipoprotein J alone and in a complex with Alzheimer disease amyloid beta at the blood-brain and blood-cerebrospinal fluid barriers," *PNAS*, 93(9):4229-4334 (1996) abstract only.

Borenstein, S., "New Alzheimer's vaccine to be tested on people soon, Early experiments on mice halted condition; considered safe for humans," *Free Press*, Jul. 23, 2001.

Broadwell et al, "Serum proteins bypass the blood-brain fluid barriers for extracellular entry to the central nervous system," *Exp. Neurol.*, 120(2)245-263 (1993).

Brookmeyer et al, "Projections of Alzheimer's Disease in the United States and the Public Health Impact of Delaying Disease Onset," *Am. J. Public Health*, 88:1337-1342 (1998).

Cassell et al., "Demography and Epidemiology of Age-Associated Neuronal Impairment," chapter 4, pp. 31-50 from *Funcitional Neurobiology of Aging*, Hof et al., eds., Academic Press (2001).

Das et al., "Reduced effectiveness of Aβ-42 immunization in APP transgenic mice with significant amyloid deposition," *Neurobiology of Aging*, 22:721-727 (2001).

European Search Report of Jan. 16, 2007 for European Application 04776252.1-2405.

Fox et al., "Presymptomatic cognitive deficits in individuals at risk of familial Alzheimer's disease," *Brain*, 121:1631-1639 (1998).

Fukutani et al., "Cerebeller pathology in sporadic and familial Alzheimer's disease including APP 717 (Val->lle) mutation cases: A morphometric investigation," *J. Neurologic Sci.*, 149:177-184 (1997).

Kalback et al., "APP Transgenic Mice Tg2576 Accumulate Aβ Peptides That Are Distinct from the Chemically Modified and Insoluble Peptides Deposited in Alzheimer's Disease Senile Plagues," *Biochemistry*, 41:922-928 (2002).

Klyubin et al., "Anti-Aβ Antibodies Prevent Block of Long-Term Potentiation in the CA1 Area of Rat Hippocampus InVivo by naturally Produced Aβ Oligomers," *Neurobiology of Aging*, 25:S224-S225, abstract P2-004, pp. S224-S225 (2004).

Kuby, J., eds., p. 123 from *Immunology, Third Edition*, W.H. Freeman & co., (1997).

Kuo et al., "Comparative Analysis of Amyloid-β Chemical Structure and Amyloid Plaque Morphology of Transgenic Mouse and Alzheimer's Disease Brains," *J. Biol. Chem.*, 276(16):12991-12998 (2001).

Merriam-Webster online medical dictionary, entry for "cure", accessed Sep. 5, 2006.

Okie, S., "Promising Vaccine Targets Ravager of Minds," *Washington Post*, p. A01, May 8, 2001.

Pardridge et al., "The Blood-Brain Barrier: Bottleneck in Brain Drug Development," *J. Am. Soc. Exp. Neurotherapeutics*, 2:3-14 (2005).

PCT Search Report of Aug. 8, 2006 for application PCT/US2005/045515.

Press Release, "Alzheimer's vaccine developer awarded Potamkin Prize," American Academy of Neurology, May 7, 2001.

Rosenberg, R. N., "The Potamkin Prize for Pick's, Alzheimer's Disease and Related Disorders," pp. 1-5.

Saldanha et al., "A single backmutation in the human kIV framework of a previously unsuccessfully humanized antibody restores the binding activity and increases the secretion in cos cells," *Molecular Immunology*, 36:709-719 (1999).

Signet Laboratories, Inc., Product data sheet for mouse monoclonal done 6E10, revised Jul. 13, 2005.

Travis, J., "A Vaccine for Alzheimer's Disease?®," *Science News Online*, 156(2) pp. 1-3 downloaded from internet (1999).

UniProtKB/Swiss-Prot entry P18525, pp. 1-3 downloaded from http://www.expasy.org/cgi-bin/niceprot.pl/printable?ac=P18525 on Feb. 8, 1997, "HV54_Mouse" (Nov. 1, 1990).

Van Leuven, F., "Single and multiple transgenic mice as models for Alzheimer's disease," *Progress in Neurobiology*, 61:305-312 (2000).

Zhang et al., "Specialized Applications, Purification of Recombinant Proteins and Study of Protein Interaction by Epitope Tagging," *Current Protocols In Mol. Biol.*, Supp 41, pp. 10.15.1 through 10.15.9 (1998).

U.S. Appl. No. 12/037,045, filed Feb. 25, 2008, Seubert.
U.S. Appl. No. 60/999,423, filed Oct. 17, 2007, Black.
U.S. Appl. No. 11/894,789, filed Aug. 20, 2007, Basi.
U.S. Appl. No. 11/894,754, filed Aug. 20, 2007.
U.S. Appl. No. 11/894,714, filed Aug. 20, 2007, Basi.
U.S. Appl. No. 11/894,665, filed Aug. 20, 2007, Schenk.
U.S. Appl. No. 11/893,123, filed Aug. 20, 2007.
U.S. Appl. No. 11/893,110, filed Aug. 20, 2007.
U.S. Appl. No. 11/893,103, filed Aug. 20, 2007.
U.S. Appl. No. 11/893,094, filed Aug. 20, 2007.
U.S. Appl. No. 11/842,120, filed Aug. 20, 2007, Schenk.
U.S. Appl. No. 11/842,116, filed Aug. 20, 2007, Schenk.
U.S. Appl. No. 11/842,113, filed Aug. 20, 2007, Schenk.
U.S. Appl. No. 11/842,101, filed Aug. 20, 2007, Schenk.
U.S. Appl. No. 11/842,056, filed Aug. 20, 2007, Basi.
U.S. Appl. No. 11/842,042, filed Aug. 20, 2007, Basi.
U.S. Appl. No. 11/842,023, filed Aug. 20, 2007, Basi.
U.S. Appl. No. 11/841,993, filed Aug. 20, 2007, Arumugham.
U.S. Appl. No. 11/841,950, filed Aug. 20, 2007, Arumugham.
U.S. Appl. No. 11/841,919, filed Aug. 20, 2007, Arumugham.
U.S. Appl. No. 11/841,897, filed Aug. 20, 2007, Arumugham.
U.S. Appl. No. 11/841,882, filed Aug. 20, 2007, Arumugham.
U.S. Appl. No. 11/841,857, filed Aug. 20, 2007, Warne et al.
U.S. Appl. No. 11/841,849, filed Aug. 20, 2007, Arumugham.
U.S. Appl. No. 11/841,794, filed Aug. 20, 2007, Warne et al.
U.S. Appl. No. 11/841,832, filed Aug. 20, 2007, Warne et al.
U.S. Appl. No. 60/793,014, filed Apr. 18, 2006.
U.S. Appl. No. 11/396,417, filed Mar. 30, 2006, Schenk.
U.S. Appl. No. 11/396,391, filed Mar. 30, 2006, Schenk.
U.S. Appl. No. 11/358,951, filed Feb. 22, 2006, Solomon et al.
U.S. Appl. No. 60/736,119, filed Nov. 10, 2005, Jacobson.
U.S. Appl. No. 60/736,045, filed Nov. 10, 2005, Johnson-Wood.
U.S. Appl. No. 60/735,687, filed Nov. 10, 2005, Jacobson.
U.S. Appl. No. 60/691,821, filed Jun. 17, 2005, Godavarti.
U.S. Appl. No. 09/980,568, filed Mar. 12, 2005, Hirtzer.
U.S. Appl. No. 60/648,639, filed Jan. 28, 2005, Luisi et al.
U.S. Appl. No. 60/648,631, filed Jan. 28, 2005, Luisi et al.
U.S. Appl. No. 60/637,253, filed Dec. 16, 2004, Jacobson.
U.S. Appl. No. 60/637,138, filed Dec. 16, 2004, Jacobson.
U.S. Appl. No. 60/636,842, filed Dec. 15, 2004, Jacobson.
U.S. Appl. No. 60/636,810, filed Dec. 15, 2004, Jacobson.
U.S. Appl. No. 60/636,776, filed Dec. 15, 2004, Basi.
U.S. Appl. No. 60/636,687, filed Dec. 15, 2004, Johnson-Wood.
U.S. Appl. No. 60/636,684, filed Dec. 15, 2004, Basi.
U.S. Appl. No. 60/622,525, filed Oct. 26, 2004, Pavliakova.
U.S. Appl. No. 60/616,474, filed Oct. 5, 2004, Sinacore.
U.S. Appl. No. 60/530,481, filed Dec. 17, 2003, Arumugham.
U.S. Appl. No. 60/474,654, filed May 30, 2003, Basi.
U.S. Appl. No. 60/444,150, filed Feb. 1, 2003, Yednock.
U.S. Appl. No. 09/979,701, filed Mar. 13, 2002, Schenk.
U.S. Appl. No. 60/363,751, filed Mar. 12, 2002, Basi.
U.S. Appl. No. 60/251,892, filed Dec. 6, 2000, Basi et al.
U.S. Appl. No. 09/724,929, filed Nov. 28, 2000, Weiner.
U.S. Appl. No. 09/724,921, filed Nov. 28, 2000, Weiner.
U.S. Appl. No. 09/724,575, filed Nov. 28, 2000, Schenk.
U.S. Appl. No. 09/724,291, filed Nov. 28, 2000, Schenk.
U.S. Appl. No. 09/724,288, filed Nov. 28, 2000, Schenk.
U.S. Appl. No. 09/724,273, filed Nov. 28, 2000, Schenk.
U.S. Appl. No. 09/723,765, filed Nov. 28, 2000, Schenk.
U.S. Appl. No. 09/723,544, filed Nov. 28, 2000, Schenk.
U.S. Appl. No. 09/724,495, filed Nov. 27, 2000, Schenk.
U.S. Appl. No. 09/724,319, filed Nov. 27, 2000, Schenk.
U.S. Appl. No. 09/723,766, filed Nov. 27, 2000, Hirtzer.
U.S. Appl. No. 09/723,760, filed Nov. 27, 2000, Schenk.
U.S. Appl. No. 09/723,725, filed Nov. 27, 2000, Hirtzer.
U.S. Appl. No. 09/723,713, filed Nov. 27, 2000, Schenk.
U.S. Appl. No. 09/585,656.
U.S. Appl. No. 09/580,019, filed May 26, 2000, Schenk.
U.S. Appl. No. 09/580,015, filed May 26, 2000, Schenk.
U.S. Appl. No. 09/579,690, filed May 26, 2000, Brayden.
U.S. Appl. No. 09/497,553, filed Feb. 3, 2000, Schenk.
U.S. Appl. No. 60/139,408, filed Jun. 16, 1999, Raso.
U.S. Appl. No. 60/137,047, filed Jun. 1, 1999, Hirtzer.
U.S. Appl. No. 60/137,010, filed Jun. 1, 1999, Schenk.
U.S. Appl. No. 60/136,655, filed May 28, 1999, Brayden.
U.S. Appl. No. 09/322,289, filed May 28, 1999, Schenk.
U.S. Appl. No. 09/204,838, filed Dec. 3, 1998, Weiner.
U.S. Appl. No. 60/925,228.

Aisen, P., "Inflammation and Alzheimer's Disease: Mechanisms and Therapeutic Strategies," *Gerontology*, 43:143-149 (1997).

Akiyama et al., "The amino-terminally truncated forms of amyloid β-protein in brain macrophages in the ischemic lesions of Alzheimer's disease patients," *Neuroscience Letters*, 219:115-118 (1996).

Alberts et al., eds. *Molecular Biology of The Cell, Third Edition*, chapter 23, pp. 1216-1218 (1994).

American Type Culture Collection (ATCC) Search Results for "1KTR, 1ETZ, 1JRH", http://www.atcc.org/, pp. 1-3, Feb. 22, 2007.

Askelof et al., "Protective immunogenicity of two synthetic peptides selected from the amino acid sequence of *Bordetella pertussis* toxin subunit S1," *PNAS*, 87:1347-1351 (1990).

Ard et al., "Scavenging of Alzheimer's Amyloid β-Protein by Microglia in Culture," *J. Neuroscience Research*, 43:190-202 (1996).

Bales et al., "Cholinergic dysfunction in a mouse model of Alzheimer disease is reversed by an anti-Aβ antibody," *J. Clin. Invest.*, 116(3):825-832 (2006).

Bending, "Humanization of Rodent Monoclonal Antibodies by CDR Grafting," *A Companion to Methods in Enzymology*, 8:83-93 (1995).

Ben-Yedidia et al., "Design of peptide and polypeptide vaccines," *Current Opinion in Biotechnology*, 8:442-448 (1997).

Britt et al., "Formulation of an immunogenic human cytomegalovirus vaccine: responses in mice," *J. Infect. Dis.*, 171:18-25 Abstract (1995).

Casadesus et al., "The Estrogen Myth: Potential Use of Gonadotropin-Releasing Hormone Agonists for the Treatment of Alzheimer's Disease," *Drugs R D*, 7(3):187-193 (2006).

Casey, S.O., "Posterior Reversible Encephalopathy Syndrome: Utility of Fluid-attenuated Inversion Recovery MR Imaging in the Detection of Cortical and Subcortical Lesions," *Amer J Neuroradiol*, 21:1199-1206 (2000).

Casset et al., "A Peptide Mimetic of an Anti-CD4 Monoclonal Antibody By Rational Design," *Biochemical and Biophysical Research Commiunications*, 307:198-205 (2003).

Chakrabarti et al., "Vaccinia Virus Expression Vector: Coexpression of B-Galactosidas Provides Visual Screening of Recombinant Virus Plaques," *Molecular and Cellular Biology*, 5(12):3403-3409 (1985).

Chang et al., "Adjuvant activity of incomplete Freund's adjuvant," *Advanced Drug Delivery Reviews*, 32:173-186 (1998).

Clark et al., *Chemical Immunology Antibody Engineering IgG Effector Mechanisms*, 65:88-110 (1997).

Colman, "Effects of Amino Acid Sequence Changes On Antibody-Antigen Interactions," *Research In Immunology*, 145:33-36 (1994).

Colombian Patent Application No. 98071271, Technical Opinion of Jean Paul Vernot submitted on Jun. 22, 2005 as evidence with the brief amending the nullity action (with English translation) (drafted Nov. 2004).

Comery et al., "Passive Immunization Against β-Amyloid Leads to Acute Cognition Improvement," *Society for Neuroscience*, abstract, Washington DC, Nov. 12-16, 2005.

Corey-Bloom et al., "Clinical features distinguishing large cohorts with possible AD, probable AD, and mixed dementia," *J. Am. Geriatr. Soc.*, 41(1):31-37 Abstract (1993).

De Felice et al., "β-Amyloid production, aggregation, and clearance as targets for therapy in Alzheimer's disease," *Cell Mol. Neurobiol.*, 22(5/6):545-563 (2002).

De La Cruz et al, "Immumogenicity [sic] and Epitope Mapping of Foreign Sequences via Genetically Engineered Filamentous Phage," *J Biol Chem*, 263(9):4318-4322 (1988).

Disis et al., "Granulocyte-macrophage colony-stimulating factor: An effective adjuvant for protein and peptide-based vaccines," *Blood*, 88(1):202-210 (1996).

Drew et al., "Vaccination by cholera toxin conjugated to a herpes simplex virus type 2 glycoprotein D peptide," *Journal of General Virology*, 73:2357-2366 (1992).

Ecuador Patent Application No. SP 98-2764, English translation of Expert Report submitted Apr. 19, 2007 in support of the Appeal filed on Jul. 29, 2005.

European Examination Report of Mar. 9, 2007 for European Application 01995364.5-1222.

European Examination Report of Sep. 26, 2007 for European Application 04720353.4-1222.

European Examination Report of Oct. 8, 2007 for European Application 01995364.5-1222.

Geylis et al., "Immunotherapy of Alzheimer's disease 9AD): From murine models to anti-amyloid beta 9Ab) human monoclonal antibodies," *Autoimmunity Rev.*, 5:33-39 (2000).

Gibson et al., "Abnormalities in Alzheimer's Disease Fibroblasts Bearing the APP670/671 Mutation," *Neurobiology of Aging*, 18(6):573-580 (1997).

Gilman, S. et al., "Clinical Effects of Aβ Immunization (AN1792) in Patients with AD in an Interrupted Trial," *Neurology*, 64:1553-1562 (2005).

Gross et al., "Microvascular specializations promoting rapid interstitial solute dispersion in nucleus tractus solitarius," *Am J Physiol Regul Integr Comp Physiol*, 259:R1131-R1138 (1990).

Harlow et al., eds., *Antibodies: A Laboratory Manual*, pp. 71-82 (1988).

Harlow et al., eds., *Antibodies: A Laboratory Manual*, p. 98 (1988).

Holmes et al., "Long-term Effects of Aβ$_{42}$ Immunisation in Alzheimer's Disease: Follow-up of a Randomised, Placebo-controlled Phase I Trial," *Lancet*, 372: 216-223 (2008).

Hopp et al., "Prediction of protein antigenic determiniants from amino acid sequences," Proc. Natl. Acad. Sci. USA 78:3824-3828 (1981).

Hussain et al., "Selective Increases in Antibody Isotopes and Immunoglobulin G Subclass Responses to Secreted Antigens in Tuberculosis Patients and Healthy Household Contacts of the Patients," *Clinical and Diagnostic Laboratory Immunology*, 2(6): 726-732 (1995).

Hyslop et al., "Will Anti-amyloid Therapies Work For Alzheimer's Disease?," *Lancet*, 372:180-182 (2008).

Idusogie et al., "Mapping of the C1q Binding Site on Rituxan, a Chimeric Antibody with a Human IgG1 Fc," *J. Immunology*, 164:4178-4184 (2000).

Jansen et al., "Use of Highly Encapsulated *Streptococcus pneumoniae* Strains in a Flow-Cytometric Assay for Assessment of the Phagocytic Capacity of Serotype-Specifid Antibodies," *Clinical & Diagnostic Lab. Immunol.*, 5(5):703-710 (1998).

Khatoon et al., "Levels of Normal and abnormally phosphorylated tau in different cellular and regional compartments of Alzheimer's disease and control brains," *FEBS Letters*, 351:80-84 (1994).

Kimchi et al., "Analysis of cerebral amyloid angiopathy in a transgenic mouse model of Alzheimer disease using in vivo multiphoton microscopy," *J. Neuropath Exp. Neurol.*, 60(3):274-279 (2001).

Kuby, J., eds., pp. 108-109, 131-132 from *Immunology, Third Edition*, W.H. Freeman & co., (1997).

Liu et al., "Amyloid β peptide alters intracellular vesicle trafficking and cholesterol homeostasis," *Proc. Natl. Acad. Sci.*, 95:13266-13271 (1998).

MacCallum et al., Antibody-antigen Interactions: *Contact Analysis and Binding Site Topography*, 262:732-745 (1996).

Mamikonyan et al., "Anti-Aβ$_{1-11}$ Antibody Binds to Different β-Amyloid Species, Inhibits Fibril Formation, and Disaggregates Preformed Fibrils but Not the Most Toxic Oligomers," *J Biol Chem*, 282(31) 22376-22386 (2007).

Manning et al., "Genetic Immunization with Adeno-Associated Virus Vectors Expressing Herpes Simplex Virus Type 2 Glycoproteins B and D," *Journal of Virology*, 71(10):7960-7962 (1997).

Masliah et al., "Amyloid Protien Precursor Stimulates Excitatory Amino Acid Transport," *The Journal of Biological Chemisrty*, 273(20):12548-12554 (1998).

Morgan et al., "The N-terminal end of the C$_H$2 domain of chimeric human IgG1 anti-HLA-DR is necessary for C1q, FcγRII and FcγRII binding," *Immunology*, 86:319-324 (1995).

Nashar et al., "Current progress in the development of the B subunits of cholera toxin and *Escherichia coli* heat-labile enterotoxin as carries for the oral delivery of herterologous antigens and epitopes," *Vaccine*, 11(2):235-40 (1993), abstract only.

PCT International Preliminary Examination Report of Feb. 9, 2004 for application PCT/US01/46587.

PCT Written Opinion of Dec. 14, 2004 for application PCT/US04/02856.

PCT International Preliminary Report on Patentability (Chapter I) of Sep. 16, 2005 with Written Opinion of May 9, 2005 for application PCT/US04/007503.

PCT International Preliminary Report on Patentability (Chapter II) of Dec. 21, 2006 for application PCT/US2006/002837.

PCT International Preliminary Report on Patentability (Chapter I) of Jul. 31, 2007 with Written Opinion for application PCT/US2006/004741.

PCT Written Opinion of Aug. 11, 2006 for application PCT/US2006/002837.

PCT International Preliminary Report on Patentability (Chapter II) of Apr. 27, 2006 for application PCT/US04/007503.

PCT Search Report of Apr. 6, 2006 and Written Opinion of Apr. 8, 2006 for application PCT/US04/44093.

PCT Search Report of Oct. 1, 2007 and Written Opinion of Oct. 1, 2007 for application PCT/US07/09499.

Perez et al., "The β-Amyloid Precursor Protein of Alzheimer's Disease Enhances Neuron Viability and Modulates Neuronal Polarity," *J. Neurosci.*, 17(24):9407-9414 (1997).

Piera et al., "Cytokines as adjuvants: effects on the immunogenicity of NeuAc alpha 2-GalNAc alpha-O-Ser/Thr (sialyl-Tn)," *Int. J. Cancer*, 55(1):148-152 (1993).

Pluckthun, A., "Mono- and Bivalent Antibody Fragments Produced in *Escherichia coli*: Engineering, Folding and Antigen Binding," *Immunological Reviews*, 130:151-188 (1992).

PNAS Information for Authors (revised Jan. 1997), Retrieved Apr. 21, 2008 from http://web.archive.org/web/19970610092808/www.pnas.org/iforc.shtml.

Putative CDR determination for SEQ Id Nos. 2 and 4 (pp. 1-2), Jun. 10, 2004.

Rammensee, H.G., "Chemistry of peptides associated with MHC class I and class II molecules," *Current Opinion in Immunology*, 7:85-96 (1995).

Rodriguez et al., "Enfermedad de Azlheimer. Situacion Actual γ Estrategias Terapeuticas" (Alzheimer Disease: present situation and therapeutic strategies), *Rev Cubana Med* [online], 38(2):134-142 (1999).

Rolph et al., "Recombinant viruses as vaccines and immunological tools," *Immunity to Infection*, 9:517-521 (1997).

Roses, A.D., "Apoplipoprotein E alleles as risk factors in Alzheimer's disease," *Annu. Rev. Med.*, 47:387-400 (1996).

Seubert et al., "Antibody Capture of Soluble Aβ does not Reduce Cortical Aβ Amyloidosis in the PDAPP Mouse," *Neurodegenerative Diseases*, 5:65-71 (2008).

Small, "The Role of the Amyloid Protien Precursors (APP) in Alzheimer's Disease: Does the Normal Function of APP Explain the Topography of Neurodegeneration?," *Neurochemical Research*, 23(5):795-806 (1997).

Solomon et al., "Fast induction of anti-β-amyloid peptide immune response," *Research and Practice in Alzheimer's Disease*, 6:260-264 (2002).

Soto et al., "The conformation of Alzheimer's beta peptide determines the rate of amyloid formation and its resistance to proteolysis," *Biochem. J.*, 314:701-707 (1996).

Spellerberg et al., "DNA Vaccines Against Lymphoma," Journal of Immunology, 159:1885-1892 (1997).

Staunton et al., "Primary structures of ICAM-1 demonstrates interaction between members of the immunoglobulin and intergrin supergene families," *Cell* 52(6):925-33 (1988), abstract only.

Supplementary Partial European Search Report of Apr. 10, 2007 for European Application 04720353.4-1222.

Tang et al., "Genetic immunization is a siple method for eliciting an immune response," *Nature*, 356:152-154 (1992).

Travis, J., "Saving the Mind Faces High Hurdles," *Science*, 309:731-734 (2005).

Ulvestad et al., "Fc Receptors for IgG on Cultured Human Microglia Mediate Cytotoxicity and Phagocytosis of Antibody-coated Targets," *Journal of Neuropathology and Experimental Neurology*, 53(1):27-36 (1994).

Vanderstichele et al., "Standardization of Measurement of B-amyloid(1-42) in Cerebrospinal Fluid and Plasma:," *Int. J. Exp. Clin. Invest.*, 7(4):245-258 (2000).

Winblad et al., "Hints of a therapeutic Vaccine for Alzheimer's?" *Neuron*, 38:517-519 (2003).

Whitcomb et al., "Characterization of saturable binding sites for circulating pancreatic polypeptide in rat brain," *Am J Pysiol Gastrointest Liver Physiol*, 259:G687-G691 (1990).

Wu et al., "Expression of immunogenic epitopes of hepatitis B surface antigen with hybrid flagellin proteins by a vaccine strain of *Salmonella*," *PNAS*, 86:4726-4730 (1989).

Wyeth, Annual Review 2005: Creating Value . . . Advancing Health (Feb. 27, 2006).

Xiang et al., "Manipulation of the immune response to a plasmid-encoded viral antigen by coinoculation with plasmids expressing cytokines," *Immunity*, 2(2):129-135 Abstract (1995).

Yankner et al., "Neurotrophic and Neurotoxic effects of Amyloid β Protein: Reversal by Tachykinin Neuropeptides," *Science*, 250:279-282 (1990).

U.S. Appl. No. 09/201,430, Office Action mailed Dec. 21, 1999.
U.S. Appl. No. 09/201,430, Office Action mailed May 10, 2000.
U.S. Appl. No. 09/204,838, Office Action mailed Mar. 17, 2000.
U.S. Appl. No. 09/322,289, Office Action mailed Sep. 29, 2000.
U.S. Appl. No. 09/497,553, Office Action mailed Oct. 3, 2003.
U.S. Appl. No. 09/580,015, Office Action mailed Feb. 11, 2002.
U.S. Appl. No. 09/580,018, Office Action mailed Mar. 12, 2002.
U.S. Appl. No. 09/580,019, Office Action mailed Mar. 12, 2002.
U.S. Appl. No. 09/723,544, Office Action mailed Sep. 23, 2002.
U.S. Appl. No. 09/723,760, Office Action mailed Mar. 12, 2002.
U.S. Appl. No. 09/723,765, Office Action mailed Mar. 12, 2002.
U.S. Appl. No. 09/723,766, Office Action mailed Mar. 5, 2002.
U.S. Appl. No. 09/723,766, Office Action mailed Jun. 11, 2002.
U.S. Appl. No. 09/724,273, Office Action mailed Jul. 2, 2002.
U.S. Appl. No. 09/724,273, Office Action mailed Nov. 8, 2005.
U.S. Appl. No. 09/724,288, Office Action mailed Mar. 12, 2002.
U.S. Appl. No. 09/724,288, Office Action mailed May 3, 2004.
U.S. Appl. No. 09/724,319, Office Action mailed Jul. 21, 2003.
U.S. Appl. No. 09/724,495, Office Action mailed Sep. 24, 2002.
U.S. Appl. No. 09/724,495, Office Action mailed Mar. 13, 2003.
U.S. Appl. No. 09/724,551, Office Action mailed Jul. 2, 2002.
U.S. Appl. No. 09/724,552, Office Action mailed May 6, 2002.
U.S. Appl. No. 09/724,567, Office Action mailed Mar. 27, 2002.
U.S. Appl. No. 09/724,575, Office Action mailed Mar. 27, 2002.
U.S. Appl. No. 09/724,921, Office Action mailed Apr. 30, 2002.
U.S. Appl. No. 09/724,929, Office Action mailed Mar. 22, 2002.
U.S. Appl. No. 09/724,940, Office Action mailed Mar. 13, 2003.
U.S. Appl. No. 09/724,953, Office Action mailed Mar. 26, 2002.
U.S. Appl. No. 09/724,961, Office Action mailed Mar. 12, 2002.
U.S. Appl. No. 09/979,701, Office Action mailed Feb. 15, 2005.
U.S. Appl. No. 09/979,701, Office Action mailed Sep. 15, 2005.
U.S. Appl. No. 09/979,952, Office Action mailed Aug. 7, 2003.
U.S. Appl. No. 09/980,568, Office Action mailed May 29, 2003.
U.S. Appl. No. 10/010,942, Office Action mailed Sep. 24, 2003.
U.S. Appl. No. 10/232,030, Office Action mailed Dec. 2, 2004.
U.S. Appl. No. 10/388,214, Office Action mailed May 31, 2005.
U.S. Appl. No. 10/388,389, Office Action mailed Nov. 22, 2005.
U.S. Appl. No. 10/429,216, Office Action mailed Dec. 28, 2005.
U.S. Appl. No. 10/544,093, Office Action, mailed Jun. 16, 2008.
U.S. Appl. No. 10/625,854, Office Action mailed Nov. 10, 2005.
U.S. Appl. No. 10/703,713, Office Action mailed Nov. 5, 2004.
U.S. Appl. No. 10/704,070, Office Action mailed Nov. 5, 2004.
U.S. Appl. No. 10/771,174, Office Action mailed Sep. 14, 2006.
U.S. Appl. No. 10/777,792, Office Action mailed Mar. 2, 2006.
U.S. Appl. No. 10/788,666 , Office Action mailed Jan. 12, 2005.
U.S. Appl. No. 10/789,273, Office Action mailed Sep. 22, 2006.
U.S. Appl. No. 10/822,968, Office Action mailed Mar. 22, 2006.
U.S. Appl. No. 10/823,463, Office Action mailed Feb. 4, 2005.
U.S. Appl. No. 10/828,548, Office Action mailed Feb. 4, 2005.
U.S. Appl. No. 10/828,548, Office Action mailed Sep. 29, 2005.
U.S. Appl. No. 10/858,855, Office Action mailed Jun. 22, 2006.
U.S. Appl. No. 10/923,267, Office Action mailed Jul. 21, 2006.
U.S. Appl. No. 10/923,469, Office Action mailed Mar. 29, 2007.
U.S. Appl. No. 10/923,474, Office Action mailed Feb. 15, 2005.
U.S. Appl. No. 10/928,926, Office Action mailed Jan. 12, 2007.
U.S. Appl. No. 10/934,819, Office Action mailed Oct. 14, 2005.
U.S. Appl. No. 11/058,757, Office Action mailed May 3, 2005.
U.S. Appl. No. 11/058,757, Office Action mailed Aug. 24, 2005.
U.S. Appl. No. 11/244,678, Office Action mailed Apr. 18, 2007.
U.S. Appl. No. 11/245,524, Office Action mailed May 15, 2007.
U.S. Appl. No. 11/245,916, Office Action mailed Jan. 13, 2006.
U.S. Appl. No. 11/260,047, Office Action mailed Oct. 26, 2006.
U.S. Appl. No. 11/303,478, Office Action mailed Apr. 1, 2008.
U.S. Appl. No. 11/304,072, Office Action mailed Dec. 20, 2006.
U.S. Appl. No. 11/304,986, Office Action mailed Jan. 2, 2008.
U.S. Appl. No. 11/305,889, Office Action mailed Jul. 25, 2008.
U.S. Appl. No. 11/305,889, Office Action mailed May 4, 2007.
U.S. Appl. No. 11/305,899, Office Action mailed Apr. 4, 2008.
U.S. Appl. No. 11/342,353, Office Action mailed Mar. 26, 2008.
U.S. Appl. No. 11/342,353, Office Action mailed Jul. 9, 2008.
U.S. Appl. No. 11/454,772, Office Action mailed Feb. 27, 2007.
U.S. Appl. No. 09/201,430, Office Action mailed Jan. 17, 2001.
U.S. Appl. No. 09/201,430, Examiner Interview Summary mailed May 30, 2001.
U.S. Appl. No. 09/204,838, Office Action mailed Dec. 21, 2000.
U.S. Appl. No. 09/322,289, Office Action mailed Jun. 19, 2001.
U.S. Appl. No. 09/322,289, Examiner Interview Summary mailed Jun. 27, 2006.
U.S. Appl. No. 09/497,553, Office Action mailed Nov. 29, 2005.
U.S. Appl. No. 09/580,018, Office Action mailed May 20, 2003.
U.S. Appl. No. 09/723,384, Office Action mailed Oct. 9, 2002.
U.S. Appl. No. 09/723,384, Examiner Interview Summary mailed Mar. 28, 2003.
U.S. Appl. No. 09/723,544, Office Action mailed Aug. 11, 2003.
U.S. Appl. No. 09/723,713, Office Action mailed Mar. 26, 2002.
U.S. Appl. No. 09/723,760, Office Action mailed Dec. 19, 2002.
U.S. Appl. No. 09/723,762, Office Action mailed Oct. 2, 2001.
U.S. Appl. No. 09/723,765, Office Action mailed Dec. 3, 2002.

U.S. Appl. No. 09/723,765, Examiner Interview Summary mailed Mar. 18, 2003.
U.S. Appl. No. 09/723,765, Examiner Interview Summary mailed Jan. 25, 2006.
U.S. Appl. No. 09/723,765, Examiner Interview Summary mailed Oct. 8, 2008.
U.S. Appl. No. 09/723,766, Office Action mailed Nov. 1, 2002.
U.S. Appl. No. 09/724,102, Office Action mailed Oct. 3, 2001.
U.S. Appl. No. 09/724,273, Office Action mailed Apr. 21, 2003.
U.S. Appl. No. 09/724,288, Office Action mailed Dec. 11, 2002.
U.S. Appl. No. 9/724,319, Office Action mailed Apr. 26, 2004.
U.S. Appl. No. 09/724,319, Examiner Interview Summary mailed Jul. 19, 2004.
U.S. Appl. No. 09/724,319, Examiner Interview Summary mailed Apr. 9, 2008.
U.S. Appl. No. 09/724,477, Office Action mailed Oct. 2, 2001.
U.S. Appl. No. 09/724,489, Office Action mailed Oct. 2, 2002.
U.S. Appl. No. 09/724,495, Office Action mailed Jan. 16, 2004.
U.S. Appl. No. 09/724,551, Office Action mailed Jun. 3, 2003.
U.S. Appl. No. 09/724,552, Office Action mailed Jun. 3, 2003.
U.S. Appl. No. 09/724,552, Examiner Interview Summary mailed Dec. 3, 2003.
U.S. Appl. No. 09/724,567, Office Action mailed Nov. 15, 2002.
U.S. Appl. No. 09/724,575, Office Action mailed Nov. 21, 2002.
U.S. Appl. No. 09/724,575, Examiner Interview Summary mailed May 6, 2005.
U.S. Appl. No. 09/724,921, Office Action mailed Jan. 28, 2003.
U.S. Appl. No. 09/724,929, Office Action mailed Jul. 22, 2003.
U.S. Appl. No. 09/724,940, Office Action mailed Dec. 24, 2003.
U.S. Appl. No. 09/724,953, Office Action mailed Nov. 27, 2002.
U.S. Appl. No. 09/724,961 Office Action mailed May 16, 2003.
U.S. Appl. No. 09/724,961, Examiner Interview Summary mailed Dec. 3, 2003.
U.S. Appl. No. 09/979,701, Office Action mailed Jan. 10, 2006.
U.S. Appl. No. 09/979,952, Office Action mailed Dec. 30, 2003.
U.S. Appl. No. 09/980,568, Office Action mailed Feb. 23, 2004.
U.S. Appl. No. 10/010,942, Office Action mailed May 26, 2004.
U.S. Appl. No. 10/010,942, Examiner Interview Summary mailed Nov. 18, 2004.
U.S. Appl. No. 10/010,942, Examiner Interview Summary mailed Jan. 19, 2005.
U.S. Appl. No. 10/010,942, Examiner Interview Summary mailed Feb. 22, 2006.
U.S. Appl. No. 10/010,942 ,Examiner Interview Summary mailed May 10, 2006.
U.S. Appl. No. 10/010,942 ,Examiner Interview Summary mailed May 11, 2006.
U.S. Appl. No. 10/010,942, Examiner Interview Summary mailed May 11, 2006.
U.S. Appl. No. 10/232,030, Office Action mailed Oct. 14, 2005.
U.S. Appl. No. 10/232,030, Examiner Interview Summary mailed Feb. 17, 2006.
U.S. Appl. No. 10/388,214, Office Action mailed Jan. 31, 2006.
U.S. Appl. No. 10/388,214, Examiner Interview Summary mailed Oct. 2, 2006.
U.S. Appl. No. 10/388,214, Examiner Interview Summary mailed Nov. 6, 2006.
U.S. Appl. No. 10/388,389, Examiner Interview Summary mailed May 22, 2006.
U.S. Appl. No. 10/388,389, Examiner Interview Summary mailed May 31, 2006.
U.S. Appl. No. 10/429,216, Office Action mailed Apr. 11, 2006.
U.S. Appl. No. 10/625,854, Office Action mailed Feb. 7, 2006.
U.S. Appl. No. 10/625,854, Examiner Interview Summary mailed Jun. 26, 2007.
U.S. Appl. No. 10/703,713, Office Action mailed Sep. 27, 2005.
U.S. Appl. No. 10/703,713, Examiner Interview Summary mailed Feb. 21, 2006.
U.S. Appl. No. 10/703,713, Examiner Interview Summary mailed Mar. 2, 2006.
U.S. Appl. No. 10/704,070, Office Action mailed Sep. 26, 2005.
U.S. Appl. No. 10/771,174, Office Action mailed Nov. 27, 2006.
U.S. Appl. No. 10/777,792, Office Action mailed Aug. 7, 2006.
U.S. Appl. No. 10/788,666, Office Action mailed Dec. 15, 2005.
U.S. Appl. No. 10/823,463, Office Action mailed Sep. 30, 2005.
U.S. Appl. No. 10/828,548, Office Action mailed Feb. 13, 2006.
U.S. Appl. No. 10/858,855, Office Action mailed Mar. 7, 2007.
U.S. Appl. No. 10/890,000, Office Action mailed Apr. 13, 2005.
U.S. Appl. No. 10/890,024, Office Action mailed Nov. 2, 2005.
U.S. Appl. No. 10/890,070, Office Action mailed Apr. 8, 2005.
U.S. Appl. No. 10/890,071, Office Action mailed Dec. 18, 2006.
U.S. Appl. No. 10/889,999, Office Action mailed Jan. 5, 2005.
U.S. Appl. No. 10/923,469, Examiner Interview Summary mailed Apr. 9, 2008.
U.S. Appl. No. 10/923,469, Office Action mailed Jul. 3, 2007.
U.S. Appl. No. 10/923,471, Office Action mailed Jan. 5, 2005.
U.S. Appl. No. 10/923,474 Office Action mailed Nov. 17, 2005.
U.S. Appl. No. 10/923,605, Office Action mailed Apr. 12, 2007.
U.S. Appl. No. 10/934,818, Office Action mailed Mar. 26, 2007.
U.S. Appl. No. 10/934,819, Office Action mailed Jan. 24, 2006.
U.S. Appl. No. 11/058,757, Office Action mailed Oct. 20, 2005.
U.S. Appl. No. 11/108,102, Office Action mailed Jan. 11, 2006.
U.S. Appl. No. 11/244,678, Office Action mailed Jul. 13, 2007.
U.S. Appl. No. 11/245,524, Office Action mailed Sep. 27, 2007.
U.S. Appl. No. 11/245,916, Office Action mailed May 19, 2006.
U.S. Appl. No. 11/260,047, Office Action mailed May 15, 2007.
U.S. Appl. No. 11/260,047, Examiner Interview Summary mailed May 15, 2007.
U.S. Appl. No. 11/274,493, Office Action mailed Apr. 23, 2007.
U.S. Appl. No. 11/305,889, Office Action mailed Aug. 14, 2007.
U.S. Appl. No. 11/45,772, Examiner Interview Summary mailed Apr. 13, 2007.
U.S. Appl. No. 11/454,772, Office Action mailed Jun. 27, 2007.
U.S. Appl. No. 09/201,430, Office Action mailed Oct. 1, 2002.
U.S. Appl. No. 09/204,838, Office Action mailed Apr. 18, 2003.
U.S. Appl. No. 09/322,289, Office Action mailed Feb. 24, 2005.
U.S. Appl. No. 09/322,289, Office Action mailed Nov. 17, 2006.
U.S. Appl. No. 09/322,289, Office Action mailed Feb. 7, 2008.
U.S. Appl. No. 09/723,713, Office Action mailed Oct. 24, 2003.
U.S. Appl. No. 09/723,713, Office Action mailed Apr. 19, 2005.
U.S. Appl. No. 09/723,725, Office Action mailed Dec. 9, 2002.
U.S. Appl. No. 09/723,760, Office Action mailed May 4, 2005.
U.S. Appl. No. 09/723,765, Office Action mailed May 22, 2008.
U.S. Appl. No. 09/723,765, Office Action mailed Aug. 10, 2004.
U.S. Appl. No. 09/724,273, Office Action mailed Jun. 22, 2004.
U.S. Appl. No. 09/724,273, Office Action mailed Jun. 8, 2006.
U.S. Appl. No. 09/724,273, Office Action mailed Dec. 22, 2006.
U.S. Appl. No. 09/724,288, Office Action mailed Dec. 14, 2004.
U.S. Appl. No. 09/724,288, Office Action mailed Jun. 21, 2006.
U.S. Appl. No. 09/724,288, Office Action mailed Apr. 23, 2007.
U.S. Appl. No. 09/724,288, Office Action mailed Oct. 3, 2007.
U.S. Appl. No. 09/724,288, Office Action mailed Mar. 18, 2008.
U.S. Appl. No. 09/724,319, Office Action mailed Aug. 15, 2005.
U.S. Appl. No. 09/724,319, Office Action mailed May 16, 2007.
U.S. Appl. No. 09/724,319, Office Action mailed Jan. 11, 2008.
U.S. Appl. No. 09/724,575, Office Action mailed May 6, 2005.
U.S. Appl. No. 09/724,575, Office Action mailed Oct. 17, 2005.
U.S. Appl. No. 09/724,575, Office Action mailed Mar. 31, 2006.
U.S. Appl. No. 09/980,568, Office Action mailed Nov. 2, 2004.
U.S. Appl. No. 10/010,942, Office Action mailed Jan. 19, 2005.
U.S. Appl. No. 10/010,942, Office Action mailed Oct. 3, 2005.
U.S. Appl. No. 10/232,030, Office Action mailed Jun. 15, 2007.
U.S. Appl. No. 10/429,216, Office Action mailed Jan. 28, 2008.
U.S. Appl. No. 10/625,854, Office Action mailed May 15, 2007.
U.S. Appl. No. 10/703,713, Office Action mailed Jun. 2, 2006.
U.S. Appl. No. 10/777,792, Office Action mailed Apr. 3, 2008.
U.S. Appl. No. 10/828,548, Office Action mailed Sep. 11, 2007.
U.S. Appl. No. 10/889,999, Office Action mailed Aug. 15, 2005.
U.S. Appl. No. 10/890,000, Office Action mailed Sep. 19, 2005.
U.S. Appl. No. 10/890,000, Office Action mailed Mar. 10, 2006.
U.S. Appl. No. 10/890,070, Office Action mailed Sep. 29, 2005.
U.S. Appl. No. 10/923,469, Office Action mailed Mar. 24, 2008.
U.S. Appl. No. 10/923,471, Office Action mailed Aug. 24, 2005.
U.S. Appl. No. 10/923,471, Office Action mailed May 15, 2006.
U.S. Appl. No. 10/923,471, Office Action mailed Jul. 31, 2007.
U.S. Appl. No. 10/923,474 Office Action mailed Jun. 26, 2007.

U.S. Appl. No. 11/244,678, Office Action mailed Sep. 23, 2008.
U.S. Appl. No. 11/245,524, Office Action mailed Jun. 4, 2008.
U.S. Appl. No. 11/245,916, Office Action mailed Jan. 28, 2008.
U.S. Appl. No. 11/342,353, Office Action mailed Jul. 22, 2008.
U.S. Appl. No. 11/244,678, Office Action mailed Mar. 24, 2008.
U.S. Appl. No. 10/232,030, Advisory Action mailed Oct. 30, 2006.
U.S. Appl. No. 10/232,030, Office Action mailed Apr. 1, 2008.
U.S. Appl. No. 10/704,070, Office Action mailed Jun. 6, 2006.
U.S. Appl. No. 10/771,174, Office Action mailed Aug. 23, 2007.
U.S. Appl. No. 10/858,855, Office Action mailed Nov. 23, 2007.
U.S. Appl. No. 10/858,855, Advisory Action mailed Apr. 7, 2008.
U.S. Appl. No. 10/388,214, Office Action mailed Jul. 28, 2006.
U.S. Appl. No. 11/305,889, Office Action mailed May 23, 2008.
U.S. Appl. No. 11/454,772, Office Action mailed Dec. 21, 2007.
U.S. Appl. No. 09/201,430, Office Action mailed Nov. 26, 2001.
U.S. Appl. No. 09/201,430, Advisory Action mailed Jun. 18, 2002.
U.S. Appl. No. 09/322,289, Office Action mailed Oct. 16, 2005.
U.S. Appl. No. 09/322,289, Office Action mailed Nov. 29, 2005.
U.S. Appl. No. 09/322,289, Office Action mailed Jul. 17, 2007.
U.S. Appl. No. 09/723,713, Office Action mailed Feb. 12, 2002.
U.S. Appl. No. 09/723,713, Office Action mailed Jun. 3, 2004.
U.S. Appl. No. 09/723,713, Office Action mailed Jan. 11, 2006.
U.S. Appl. No. 09/723,713, Advisory Action mailed Dec. 20, 2004.
U.S. Appl. No. 09/723,760, Office Action mailed Feb. 23, 2004.
U.S. Appl. No. 09/723,760, Office Action mailed Dec. 29, 2005.
U.S. Appl. No. 09/723,760, Advisory Action mailed Dec. 16, 2004.
U.S. Appl. No. 09/724,319 Office Action mailed May 2, 2006.
U.S. Appl. No. 09/724,495, Office Action mailed Sep. 26, 2005.
U.S. Appl. No. 09/724,495, Advisory Action mailed May 16, 2004.
U.S. Appl. No. 10/828,548, Office Action mailed Oct. 24, 2006.
U.S. Appl. No. 10/828,548, Office Action mailed Jun. 4, 2008.
U.S. Appl. No. 10/828,548, Advisory Action mailed Jun. 8, 2007.
U.S. Appl. No. 10/923,471, Office Action mailed Dec. 29, 2006.
U.S. Appl. No. 10/923,471, Office Action mailed Apr. 24, 2008.
U.S. Appl. No. 10/923,474 Office Action mailed Aug. 4, 2006.
U.S. Appl. No. 10/923,474, Advisory Action mailed Feb. 22, 2007.
U.S. Appl. No. 11/058,757, Office Action mailed Aug. 11, 2006.
U.S. Appl. No. 11/058,757, Advisory Action mailed Mar. 5, 2007.
U.S. Appl. No. 09/724,273, Office Action mailed Oct. 16, 2003.
U.S. Appl. No. 09/724,273, Advisory Action mailed Mar. 18, 2004.
U.S. Appl. No. 09/724,273, Office Action mailed Dec. 28, 2004.
U.S. Appl. No. 09/724,273, Advisory Action mailed Jun. 16, 2005.
U.S. Appl. No. 09/724,273, Office Action mailed Aug. 22, 2007.
U.S. Appl. No. 09/724,288, Office Action mailed Sep. 9, 2003.
U.S. Appl. No. 09/724,288, Advisory Action mailed Jan. 6, 2004.
U.S. Appl. No. 09/724,288, Office Action mailed Jul. 12, 2005.
U.S. Appl. No. 09/724,288, Advisory Action mailed Mar. 3, 2006.
U.S. Appl. No. 10/777,792, Office Action mailed May 8, 2007.
U.S. Appl. No. 10/890,024, Office Action mailed Jun. 1, 2006.
U.S. Appl. No. 10/889,999, Office Action mailed Mar. 14, 2006.
U.S. Appl. No. 10/890,000, Office Action mailed Nov. 24, 2006.
U.S. Appl. No. 10/890,000, Advisory Action mailed Jan. 14, 2008.
U.S. Appl. No. 09/723,765, Office Action mailed Oct. 7, 2003.
U.S. Appl. No. 09/723,765, Advisory Action mailed Feb. 9, 2004.
U.S. Appl. No. 09/723,765, Office Action mailed May 4, 2005.
U.S. Appl. No. 09/204,838, Office Action mailed Sep. 27, 2001.
U.S. Appl. No. 09/724,567, Office Action mailed Jul. 23, 2003.
U.S. Appl. No. 09/724,575, Office Action mailed Jul. 25, 2003.
U.S. Appl. No. 09/724,575, Advisory Action mailed Feb. 12, 2004.
U.S. Appl. No. 09/724,575, Office Action mailed Oct. 12, 2006.
U.S. Appl. No. 09/724,953, Office Action mailed Jul. 25, 2003.
U.S. Appl. No. 11/274,493, Office Action mailed Nov. 2, 2007.
U.S. Appl. No. 10/625,854, Office Action mailed Aug. 23, 2006.
U.S. Appl. No. 10/625,854, Office Action mailed Nov. 7, 2007.
U.S. Appl. No. 10/625,854, Advisory Action mailed Jan. 8, 2008.
U.S. Appl. No. 11/108,102, Office Action mailed Sep. 6, 2006.
U.S. Appl. No. 11/245,916, Office Action mailed Jan. 12, 2007.
U.S. Appl. No. 11/245,916, Advisory Action mailed May 15, 2007.
U.S. Appl. No. 11/245,916, Advisory Action mailed Oct. 18, 2007.
U.S. Appl. No. 10/429,216, Office Action mailed Jan. 3, 2007.
U.S. Appl. No. 10/890,070, Office Action mailed Jun. 1, 2006.
U.S. Appl. No. 09/201,430, Notice of Allowance mailed Mar. 26, 2003.
U.S. Appl. No. 09/201,430, Notice of Allowance mailed Sep. 23, 2003.
U.S. Appl. No. 09/724,477, Notice of Allowance mailed Apr. 30, 2003.
U.S. Appl. No. 09/724,477, Notice of Allowance mailed Sep. 23, 2003.
U.S. Appl. No. 09/723,927, Notice of Allowance mailed Sep. 23, 2003.
U.S. Appl. No. 09/723,762, Notice of Allowance mailed May 1, 2003.
U.S. Appl. No. 09/724,102, Notice of Allowance mailed Aug. 22, 2003.
U.S. Appl. No. 09/724,489, Notice of Allowance mailed Mar. 25, 2003.
U.S. Appl. No. 09/724,489, Notice of Allowance mailed Sep. 22, 2003.
U.S. Appl. No. 10/232,030, Notice of Allowance mailed Sep. 4, 2008.
U.S. Appl. No. 10/816,022, Notice of Allowance mailed Jul. 1, 2004.
U.S. Appl. No. 10/816,529, Notice of Allowance mailed Jul. 1, 2004.
U.S. Appl. No. 10/815,391, Notice of Allowance mailed Jul. 1, 2004.
U.S. Appl. No. 10/815,353, Notice of Allowance mailed Jul. 1, 2004.
U.S. Appl. No. 10/816,380, Notice of Allowance mailed Dec. 22, 2004.
U.S. Appl. No. 10/815,404, Notice of Allowance mailed Oct. 15, 2004.
U.S. Appl. No. 10/884,892, Notice of Allowance mailed Mar. 28, 2005.
U.S. Appl. No. 09/723,384, Notice of Allowance mailed Mar. 31, 2003.
U.S. Appl. No. 09/724,940, Notice of Allowance mailed Oct. 4, 2004.
U.S. Appl. No. 09/724,961, Notice of Allowance mailed Dec. 3, 2003.
U.S. Appl. No. 09/580,018, Notice of Allowance mailed Dec. 3, 2003.
U.S. Appl. No. 09/724,552, Notice of Allowance mailed Dec. 3, 2003.
U.S. Appl. No. 09/724,551, Notice of Allowance mailed Dec. 4, 2003.
U.S. Appl. No. 09/724,567, Notice of Allowance mailed Mar. 3, 2004.
U.S. Appl. No. 09/724,953, Notice of Allowance mailed Mar. 11, 2004.
U.S. Appl. No. 09/979,952, Notice of Allowance mailed Nov. 12, 2004.
U.S. Appl. No. 10/934,609, Notice of Allowance mailed Dec. 22, 2004.
U.S. Appl. No. 10/934,609, Notice of Allowance mailed Aug. 17, 2005.
U.S. Appl. No. 10/933,559, Notice of Allowance mailed Sep. 7, 2005.
U.S. Appl. No. 10/933,559, Notice of Allowance mailed Aug. 17, 2005.
U.S. Appl. No. 10/933,559, Notice of Allowance mailed Dec. 22, 2004.
U.S. Appl. No. 10/010,942, Notice of Allowance mailed May 11, 2006.
U.S. Appl. No. 10/388,389, Notice of Allowance mailed May 31, 2006.
U.S. Appl. No. 10/388,214, Notice of Allowance mailed Mar. 1, 2007.
U.S. Appl. No. 09/322,289, Office Action mailed Jun. 4, 2009.
U.S. Appl. No. 09/723,765, Office Action mailed Dec. 5, 2008.
U.S. Appl. No. 09/724,319 Advisory Action mailed Oct. 28, 2009.
U.S. Appl. No. 09/724,319 Office Action mailed Apr. 8, 2009.
U.S. Appl. No. 10/429,216, Office Action mailed Mar. 6, 2009.
U.S. Appl. No. 10/923,469. Advisory Action mailed Apr. 16, 2009.
U.S. Appl. No. 10/923,469. Office Action mailed Dec. 29, 2008.
U.S. Appl. No. 10/923,471, Office Action mailed Dec. 24, 2009.
U.S. Appl. No. 11/245,524, Office Action mailed Nov. 20, 2009.
U.S. Appl. No. 11/245,916, Advisory Action mailed Jun. 10, 2009.
U.S. Appl. No. 11/842,042, Office Action mailed Mar. 30, 2010.
U.S. Appl. No. 09/724,288, Notice of Allowance mailed Mar. 23, 2009.

U.S. Appl. No. 11/304,986, Notice of Allowance mailed Jul. 10, 2009.
U.S. Appl. No. 11/707,639, Notice of Allowance mailed Aug. 20, 2009.
U.S. Appl. No. 12/181,238, Notice of Allowance mailed Mar. 5, 2010.
U.S. Appl. No. 11/516,724, Office Action mailed Jan. 27, 2009.
U.S. Appl. No. 11/520,438, Office Action mailed Apr. 2, 2009.
U.S. Appl. No. 11/707,639 Office Action mailed Apr. 3, 2009.
U.S. Appl. No. 11/842,085, Office Action mailed Apr. 14, 2009.
U.S. Appl. No. 11/842,113, Office Action mailed Dec. 17, 2009.
U.S. Appl. No. 11/842,120, Office Action mailed Apr. 14, 2009.
U.S. Appl. No. 12/106,206, Office Action mailed Feb. 5, 2010.
U.S. Appl. No. 12/328,740, Office Action mailed Oct. 9, 2009.
U.S. Appl. No. 12/253,929, Office Action mailed Jan. 25, 2010.
U.S. Appl. No. 09/322,289, Examiner Interview Summary mailed Jan. 15, 2009.
U.S. Appl. No. 09/723,765, Examiner Interview Summary mailed Jan. 16, 2009.
U.S. Appl. No. 10/429,216, Examiner Interview Summary mailed Mar. 6, 2006.
U.S. Appl. No. 10/544,093, Office Action mailed Feb. 9, 2009.
U.S. Appl. No. 11/303,478, Office Action mailed Mar. 18, 2009.
U.S. Appl. No. 11/304,986, Office Action mailed Dec. 31, 2008.
U.S. Appl. No. 11/305,899 Office Action mailed Dec. 10, 2008.
U.S. Appl. No. 11/520,438, Office Action mailed Aug. 6, 2009.
U.S. Appl. No. 11/842,042, Office Action mailed Jun. 24, 2009.
U.S. Appl. No. 11/842,056, Office Action mailed May 6, 2009.
U.S. Appl. No. 11/842,085, Office Action mailed Sep. 30, 2009.
U.S. Appl. No. 12/037,045, Office Action mailed Apr. 28, 2010.
U.S. Appl. No. 12/181,238, Office Action mailed May 28, 2009.
U.S. Appl. No. 12/181,238, Examiner Interview Summary mailed Mar. 5, 2010.
U.S. Appl. No. 12/253,929, Office Action mailed Apr. 28, 2010.
U.S. Appl. No. 12/336,340, Office Action mailed Mar. 4, 2010.
U.S. Appl. No. 10/429,216, Office Action mailed Mar. 12, 2010.
U.S. Appl. No. 10/544,093, Office Action mailed Jan. 22, 2010.
U.S. Appl. No. 10/858,855 Office Action mailed Dec. 12, 2008.
U.S. Appl. No. 10/858,855 Office Action mailed Dec. 15, 2009.
U.S. Appl. No. 10/923,471, Office Action mailed Mar. 20, 2009.
U.S. Appl. No. 11/245,524, Office Action mailed Apr. 17, 2009.
U.S. Appl. No. 11/842,023, Office Action mailed Aug. 14, 2009.

* cited by examiner

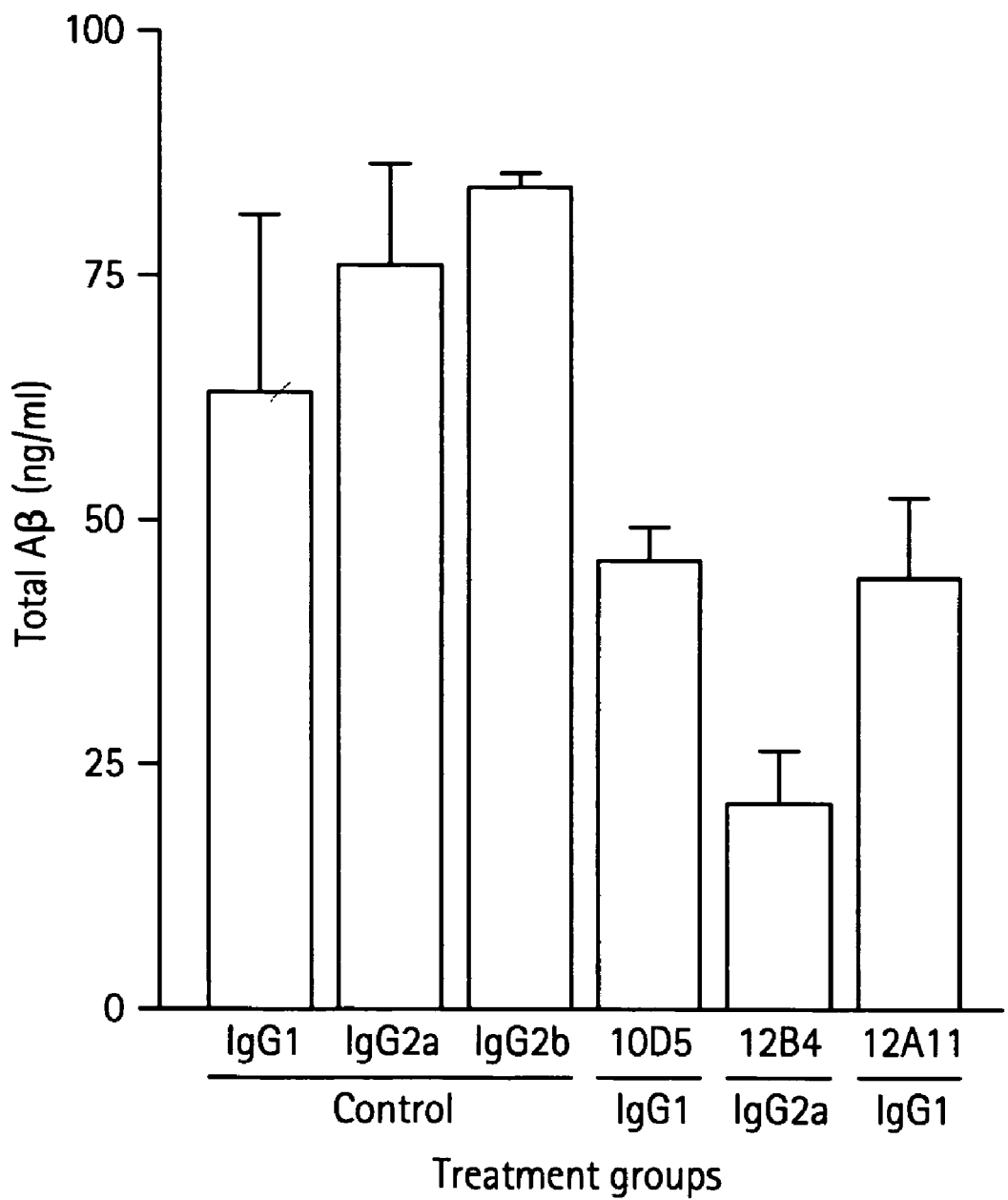

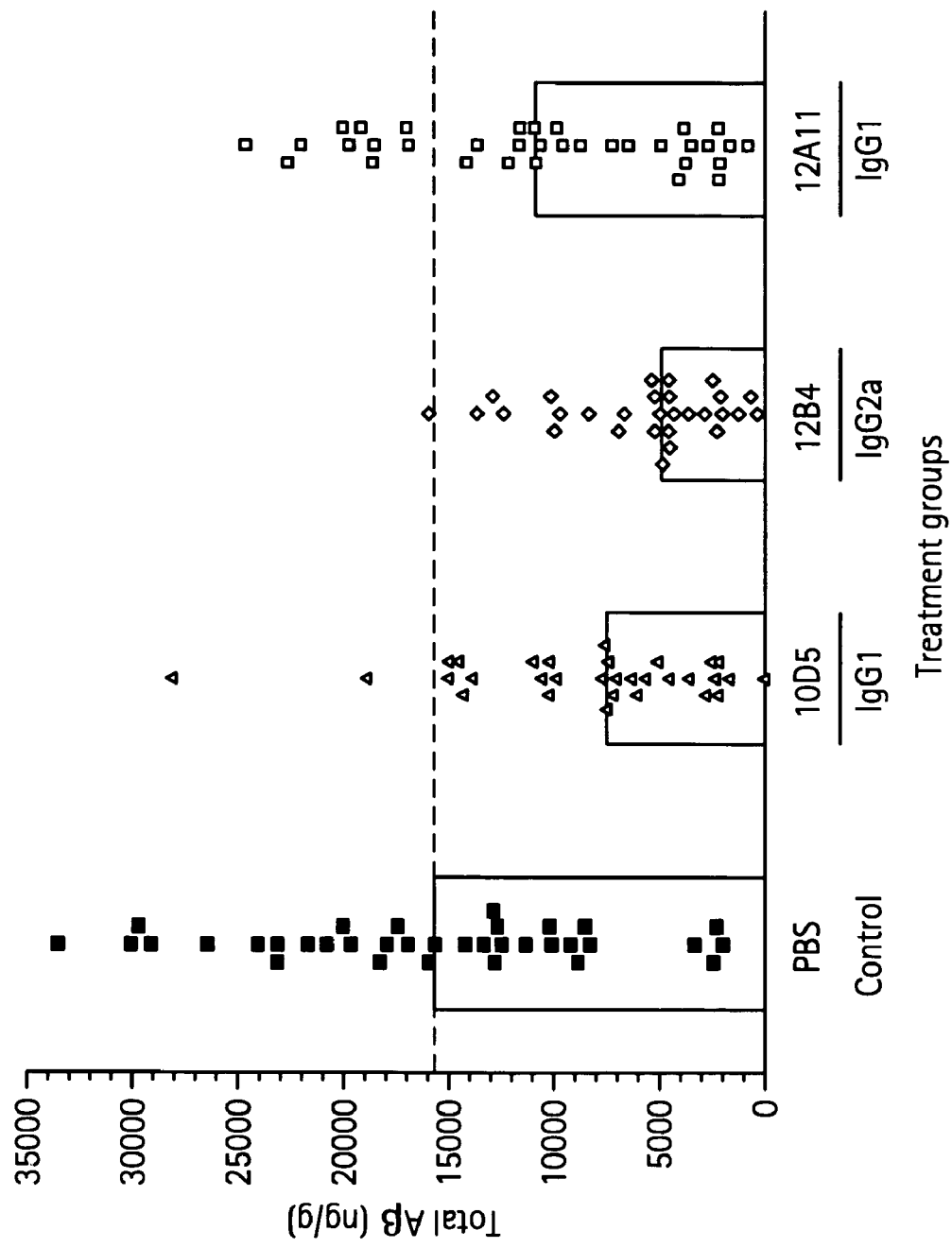

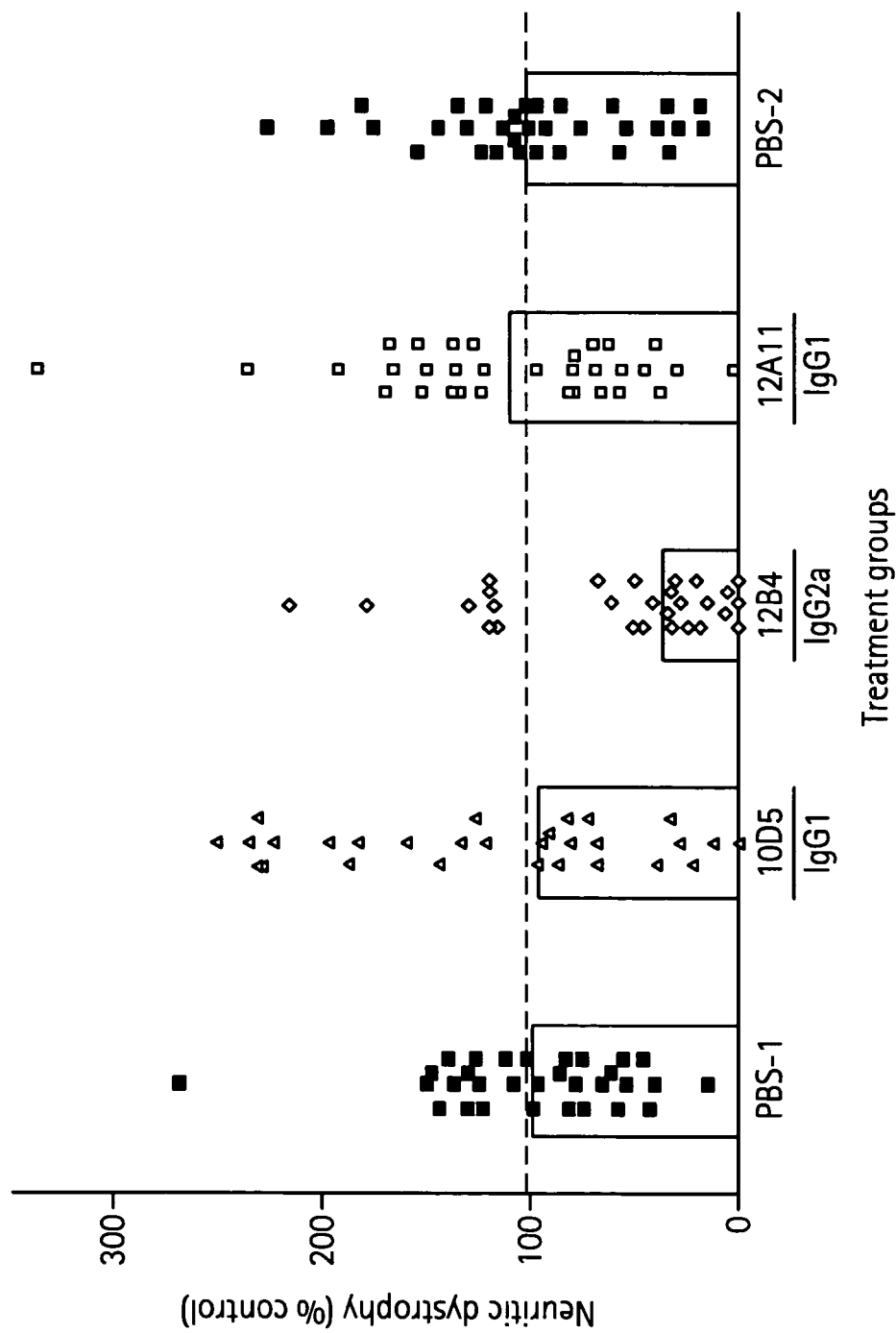

FIG. 3B

```
HindIII
AAGCTTGCCGCCACCATGGACAGGCTTACTACTTCATTCCTGCTGCTCATTGTCCCTGCATATGTCTTGTCCCAAGTTACTCTAAAAGAGTCTGGCCCTG  100
              M  D  R  L  T  T  S  F  L  L  I  V  P  A  Y  V  L  S  Q  V  T  L  K  E  S  G  P
                                                                        ——————VH——————————————————
                                                                                                 KpnI
GGATATATTGAAGCCCTCACAGACCCCTCAGTCTGACTTGTTCTTTTCTCTGGGTTTCACTGAGCACTTCTGGTATGAGTGTAGGCTGGATTCGTCAGCCTTC  200
 G  I  L  K  P  S  Q  T  L  S  L  T  C  S  F  S  G  F  S  L  S  T  S  G  M  S  V  G  W  I  R  Q  P  S
——————————————————————————VH——————————————————————————————————————————————————————————————
                                                                      ┌──────┐
                                                                      │ CDR  │
                                                                      │  H1  │
                                                                      └──────┘
 PstI                                                            EcoO109I
AGGGAAGGGTCTGGAGTGGCTGGCACACATTTGGTGGGATGATGATAAGTACTATAACCCATCCCTGAAGAGCCGGCTCACAATCTCCAAGGATACCTCC  300
 G  K  G  L  E  W  L  A  H  I  W  D  D  D  K  Y  Y  N  P  S  L  K  S  R  L  T  I  S  K  D  T  S
——————————————————————VH————————————————————————————————————————————————————————————————
              ┌───────────────────────────────────┐
              │                CDR                │
              │                H2                 │
              └───────────────────────────────────┘
AGAAACCAGTGTATTCCTCAAGATCACCAGTGTGGACACTGCAGATACTGCCACTTACTGTGCTCGAAGAACTACGGCTGACTACTTTGCCTACT  400
 R  N  Q  V  F  L  K  I  T  S  V  D  T  A  D  T  A  T  Y  Y  C  A  R  R  T  T  A  D  Y  F  A  Y
——————————————————VH————————————————————————————————————————————————————————————
                                                       ┌──────────────────────┐
                                                       │         CDR          │
                                                       │         H3           │
                                                       └──────────────────────┘
         BamHI
GGGGGCCAAGGCACCACTCTCACAGTCTCCTCAGGTGAGTGGATCC  445
 W  G  Q  G  T  T  L  T  V  S  S
——————————VH——————————
```

| | | | | |
|---|---|---|---|---|
| QVQLVESGGGVVQPGRSLRLSCAFSGFTLS | TSGMSVG | WIRQAPGKGLEWLA | HIWWDDDKYYNPSLKS | v1 |
| QVQLVESGGGVVQPGRSLRLSCAFSGFTLS | TSGMSVG | WIRQAPGKGLEWVA | HIWWDDDKYYNPSLKS | v2 |
| QVQLVESGGGVVQPGRSLRLSCAFSGFTLS | TSGMSVG | WIRQAPGKGLEWVA | HIWWDDDKYYNPSLKS | v2.1 |
| QVQLVESGGGVVQPGRSLRLSCAFSGFTLS | TSGMSVG | WIRQAPGKGLEWVA | HIWWDDDKYYNPSLKS | v3 |
| QVQLVESGGGVVQPGRSLRLSCAFSGFTLS | TSGMSVG | WIRQAPGKGLEWLA | HIWWDDDKYYNPSLKS | v4.1 |
| QVQLVESGGGVVQPGRSLRLSCAFSGFTLS | TSGMSVG | WIRQAPGKGLEWVA | HIWWDDDKYYNPSLKS | v4.2 |
| QVQLVESGGGVVQPGRSLRLSCAFSGFTLS | TSGMSVG | WIRQAPGKGLEWLA | HIWWDDDKYYNPSLKS | v4.3 |
| QVQLVESGGGVVQPGRSLRLSCAFSGFTLS | TSGMSVG | WIRQAPGKGLEWVA | HIWWDDDKYYNPSLKS | v4.4 |
| QVQLVESGGGVVQPGRSLRLSCAFSGFTLS | TSGMSVG | WIRQAPGKGLEWLA | HIWWDDDKYYNPSLKS | v5.1 |
| QVQLVESGGGVVQPGRSLRLSCAFSGFTLS | TSGMSVG | WIRQAPGKGLEWVA | HIWWDDDKYYNPSLKS | v5.2 |
| QVQLVESGGGVVQPGRSLRLSCAFSGFTLS | TSGMSVG | WIRQAPGKGLEWLA | HIWWDDDKYYNPSLKS | v5.3 |
| QVQLVESGGGVVQPGRSLRLSCAFSGFTLS | TSGMSVG | WIRQAPGKGLEWVA | HIWWDDDKYYNPSLKS | v5.4 |
| QVQLVESGGGVVQPGRSLRLSCAFSGFTLS | TSGMSVG | WIRQAPGKGLEWVA | HIWWDDDKYYNPSLKS | v5.5 |
| QVQLVESGGGVVQPGRSLRLSCAFSGFTLS | TSGMSVG | WIRQAPGKGLEWVA | HIWWDDDKYYNPSLKS | v5.6 |
| QVQLVESGGGVVQPGRSLRLSCAFSGFTLS | TSGMSVG | WIRQAPGKGLEWVA | HIWWDDDKYYNPSLKS | v6.1 |
| QVQLVESGGGVVQPGRSLRLSCAFSGFTLS | TSGMSVG | WIRQAPGKGLEWVA | HIWWDDDKYYNPSLKS | v6.2 |
| QVQLVESGGGVVQPGRSLRLSCAFSGFTLS | TSGMSVG | WIRQAPGKGLEWVA | HIWWDDDKYYNPSLKS | v6.3 |
| QVQLVESGGGVVQPGRSLRLSCAFSGFTLS | TSGMSVG | WIRQAPGKGLEWVA | HIWWDDDKYYNPSLKS | v6.4 |
| QVQLVESGGGVVQPGRSLRLSCAFSGFTLS | TSGMSVG | WVRQAPGKGLEWVA | HIWWDDDKYYNPSLKS | v7 |
| QVQLVESGGGVVQPGRSLRLSCAFSGFTLS | TSGMSVG | WIRQAPGKGLEWVA | HIWWDDDKYYNPSLKS | v8 |

FIG. 6B

| | | | |
|---|---|---|---|
| R\[I\]TIS\[k\]D\[t\]SKNT\[V\]YLQMNSLRAEDTAVYYCAR | RTTTADYFAY | WGQGTTVTVSS | v1 |
| RFTISKDTSKNTLYLQMNSLRAEDTAVYYCAR | RTTTADYFAY | WGQGTTVTVSS | v2 |
| RFTISKDTSKNTLYLQMNSLRAEDTAVYYCAR | RTTTADYFAY | WGQGTTVTVSS | v2.1 |
| RFTISRDNSKNTLYLQMNSLRAEDTAVYYCAR | RTTTADYFAY | WGQGTTVTVSS | v3 |
| R\[I\]TIS\[k\]D\[t\]SKNT\[V\]YLQMNSLRAEDTAVYYCAR | RTTTADYFAY | WGQGTTVTVSS | v4.1 |
| R\[I\]TIS\[k\]D\[t\]SKNT\[V\]YLQMNSLRAEDTAVYYCAR | RTTTADYFAY | WGQGTTVTVSS | v4.2 |
| RFTIS\[k\]D\[t\]SKNT\[V\]YLQMNSLRAEDTAVYYCAR | RTTTADYFAY | WGQGTTVTVSS | v4.3 |
| RFTISKD\[t\]SKNTLYLQMNSLRAEDTAVYYCAR | RTTTADYFAY | WGQGTTVTVSS | v4.4 |
| RFTIS\[k\]D\[t\]SKNT\[V\]YLQMNSLRAEDTAVYYCAR | RTTTADYFAY | WGQGTTVTVSS | v5.1 |
| RFTISKD\[t\]SKNTLYLQMNSLRAEDTAVYYCAR | RTTTADYFAY | WGQGTTVTVSS | v5.2 |
| RFTISKDTSKNTLYLQMNSLRAEDTAVYYCAR | RTTTADYFAY | WGQGTTVTVSS | v5.3 |
| RFTIS\[k\]D\[t\]SKNTLYLQMNSLRAEDTAVYYCAR | RTTTADYFAY | WGQGTTVTVSS | v5.4 |
| RFTISKDTSKNTLYLQMNSLRAEDTAVYYCAR | RTTTADYFAY | WGQGTTVTVSS | v5.5 |
| RFTISKDTSKNTLYLQMNSLRAEDTAVYYCAR | RTTTADYFAY | WGQGTTVTVSS | v5.6 |
| RFTIS\[k\]D\[t\]SKNT\[V\]YLQMNSLRAEDTAVYYCAR | RTTTADYFAY | WGQGTTVTVSS | v6.1 |
| RFTIS\[k\]D\[t\]SKNTLYLQMNSLRAEDTAVYYCAR | RTTTADYFAY | WGQGTTVTVSS | v6.2 |
| RFTIS\[k\]D\[t\]SKNTLYLQMNSLRAEDTAVYYCAR | RTTTADYFAY | WGQGTTVTVSS | v6.3 |
| RFTISKD\[t\]SKNTLYLQMNSLRAEDTAVYYCAR | RTTTADYFAY | WGQGTTVTVSS | v6.4 |
| R\[I\]TIS\[k\]D\[t\]SKNT\[V\]YLQMNSLRAEDTAVYYCAR | RTTTADYFAY | WGQGTTVTVSS | v7 |
| R\[I\]TISKDNSKNTLYLQMNSLRAEDTAVYYCAR | RTTTADYFAY | WGQGTTVTVSS | v8 |

FIG. 6C

```
>vh design A24F       F29L V37I       version 1
>vh design A24F       F29L V37I       version 2
>vh design A24F       F29L V37I            R71K                 version 2.1
>vh design A24F       F29L V37I                                 version 3
>vh design A24F       F29L V37I V48L F67L R71K N73T L78V        version 4.1
>vh design A24F T28S  F29L V37I      F67L R71K N73T L78V        version 4.2
>vh design A24F T28S  F29L V37I V48L      R71K N73T L78V        version 4.3
>vh design A24F T28S  F29L V37I V48L F67L R71K N73T             version 4.4
>vh design A24F       F29L V37I      F67L R71K N73T L78V        version 5.1
>vh design A24F T28S  F29L V37I      F67L R71K N73T L78V        version 5.2
>vh design A24F T28S  F29L V37I V48L F67L R71K N73T L78V        version 5.3
>vh design A24F T28S  F29L V37I V48L F67L R71K N73T L78V        version 5.4
>vh design A24F T28S  F29L V37I V48L      R71K N73T L78V        version 5.5
>vh design A24F T28S  F29L V37I           R71K N73T L78V        version 5.6
>vh design A24F       F29L V37I           R71K N73T L78V        version 6.1
>vh design A24F T28S  F29L V37I      F67L R71K N73T L78V        version 6.2
>vh design A24F T28S  F29L V37I V48L      R71K N73T             version 6.3
>vh design A24F T28S  F29L V37I V48L      R71K N73T             version 6.4
>vh design A24F       F29L                V48L F67L R71K N73T L78V version 7
>vh design A24F T28S  F29L V37I V48L F67L R71K      L78V        version 8
```

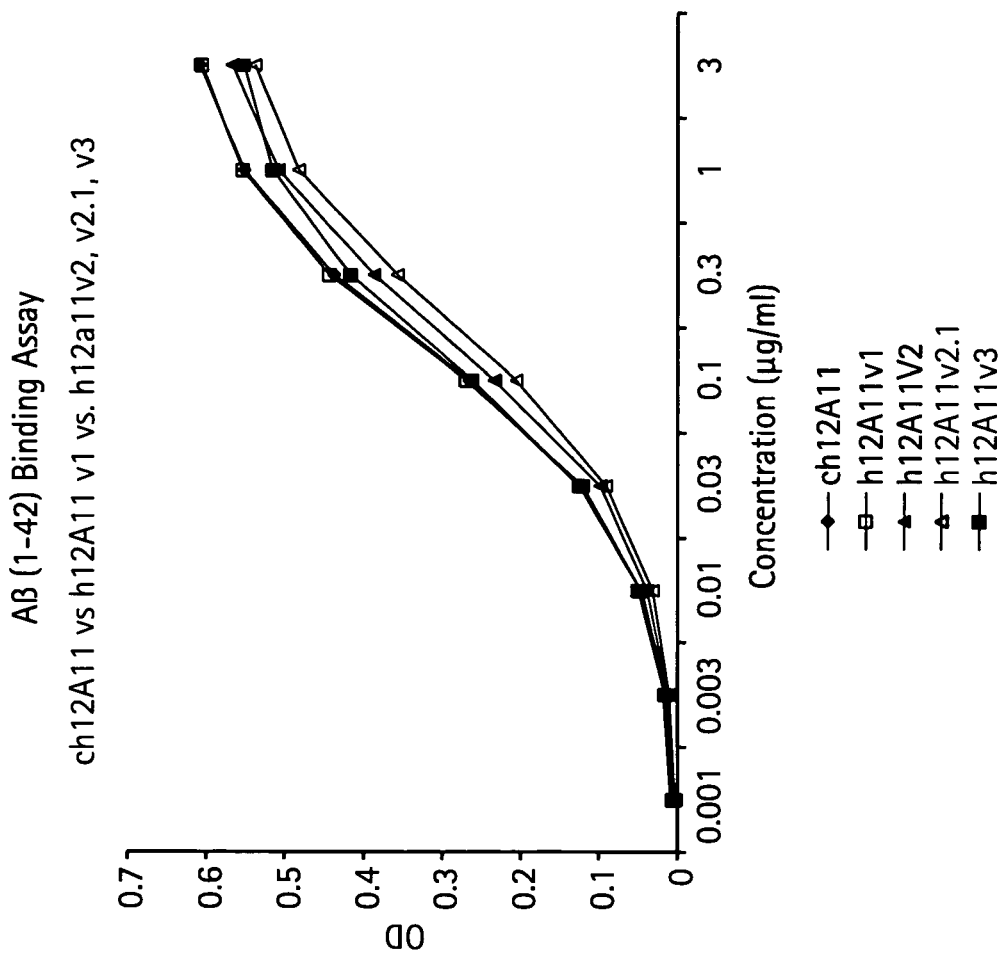

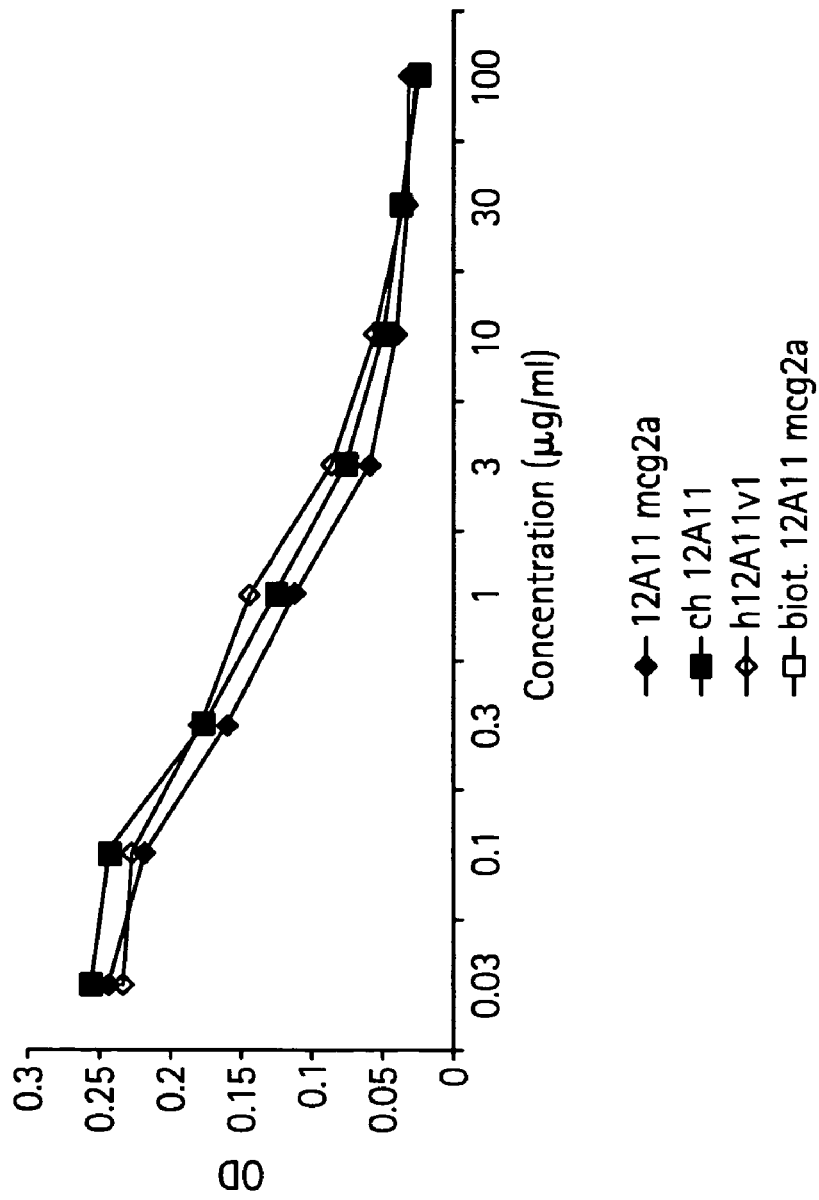

HUMANIZED ANTIBODIES THAT RECOGNIZE BETA AMYLOID PEPTIDE

RELATED APPLICATIONS

This application claims the benefit of prior-filed provisional patent application U.S. Ser. No. 60/474,654 (filed May 30, 2003) entitled "Humanized Antibodies That Recognize Beta Amyloid Peptide". The entire content of the above-referenced application is incorporated herein by reference.

BACKGROUND OF THE INVENTION

Alzheimer's disease (AD) is a progressive disease resulting in senile dementia. See generally Selkoe, *TINS* 16:403 (1993); Hardy et al., WO 92/13069; Selkoe, *J. Neuropathol. Exp. Neurol.* 53:438 (1994); Duff et al., *Nature* 373:476 (1995); Games et al., *Nature* 373:523 (1995). Broadly speaking, the disease falls into two categories: late onset, which occurs in old age (65+ years) and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropil up to 150 μm across with extracellular amyloid deposits at the center which are visible by microscopic analysis of sections of brain tissue. The accumulation of amyloid plaques within the brain is also associated with Down's syndrome and other cognitive disorders.

The principal constituent of the plaques is a peptide termed Aβ or β-amyloid peptide. Aβ peptide is a 4-kDa internal fragment of 39-43 amino acids of a larger transmembrane glycoprotein named protein termed amyloid precursor protein (APP). As a result of proteolytic processing of APP by different secretase enzymes, Aβ is primarily found in both a short form, 40 amino acids in length, and a long form, ranging from 42-43 amino acids in length. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The physical symptoms associated with this type of neural deterioration characterize Alzheimer's disease.

Several mutations within the APP protein have been correlated with the presence of Alzheimer's disease. See, e.g., Goate et al., *Nature* 349:704) (1991) (valine$^{717}$ to isoleucine); Chartier Harlan et al. *Nature* 353:844 (1991)) (valine$^{717}$ to glycine); Murrell et al., *Science* 254:97 (1991) (valine$^{717}$ to phenylalanine); Mullan et al., *Nature Genet.* 1:345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ 1-42 and Aβ1-43). Mutations in other genes, such as the presenilin genes, PS1 and PS2, are thought indirectly to affect processing of APP to generate increased amounts of long form Aβ (see Hardy, *TINS* 20: 154 (1997)).

Mouse models have been used successfully to determine the significance of amyloid plaques in Alzheimer's (Games et al., supra, Johnson-Wood et al., *Proc. Natl. Acad. Sci. USA* 94:1550 (1997)). In particular, when PDAPP transgenic mice, (which express a mutant form of human APP and develop Alzheimer's disease at a young age), are injected with the long form of Aβ, they display both a decrease in the progression of Alzheimer's and an increase in antibody titers to the Aβ peptide (Schenk et al., *Nature* 400, 173 (1999)). The observations discussed above indicate that Aβ, particularly in its long form, is a causative element in Alzheimer's disease.

Accordingly, there exists the need for new therapies and reagents for the treatment of Alzheimer's disease, in particular, therapies and reagents capable of effecting a therapeutic benefit at physiologic (e.g., non-toxic) doses.

SUMMARY OF THE INVENTION

The present invention features new immunological reagents, in particular, therapeutic antibody reagents for the prevention and treatment of amyloidogenic disease (e.g., Alzheimer's disease). The invention is based, at least in part, on the identification and characterization of a monoclonal antibody, 12A11, that specifically binds to Aβ peptide and is effective at reducing plaque burden associated with amyloidogenic disorders. Structural and functional analysis of this antibody leads to the design of various humanized antibodies for prophylactic and/or therapeutic use. In particular, the invention features humanization of the variable regions of this antibody and, accordingly, provides for humanized immunoglobulin or antibody chains, intact humanized immunoglobulins or antibodies, and functional immunoglobulin or antibody fragments, in particular, antigen binding fragments, of the featured antibody.

Polypeptides comprising the complementarity determining regions (CDRs) of the featured monoclonal antibody are also disclosed, as are polynucleotide reagents, vectors and host cells suitable for encoding said polypeptides.

Methods for treating amyloidogenic diseases or disorders (e.g., Alzheimer's disease) are disclosed, as are pharmaceutical compositions and kits for use in such applications.

Also featured are methods of identifying residues within the featured monoclonal antibodies which are important for proper immunologic function and for identifying residues which are amenable to substitution in the design of humanized antibodies having improved binding affinities and/or reduced immunogenicity, when used as therapeutic reagents.

Also featured are antibodies (e.g., humanized antibodies) having altered effector functions, and therapeutic uses thereof.

BRIEF DESCRIPTION OF THE DRAWINGS

FIG. 1 graphically depicts results from an experiment which examines the effectiveness of various antibodies, including 12A11, at clearing Aβ plaques in an ex vivo phagocytosis assay.

FIG. 2A graphically depicts results from an experiment which examines the effectiveness of various antibodies, including 12A11, at reducing total Aβ levels. The bars represent median values, and the dashed horizontal line indicates the control level. FIG. 2B graphically depicts results from an experiment which analyzes the effectiveness of various antibodies, including 12A11, at reducing neuritic dystrophy. The bars represent median values, and the dashed horizontal line indicates the control level. Data are shown for individual animals and expressed as the percentage of neuritic dystrophy relative to the mean of the control (set at 100%).

FIG. 3B depicts a DNA sequence including the murine 12A11 VH chain sequence and the deduced amino acid sequence for the VH chain (SEQ ID NOs: 6 and 3, respectively). Mature VH chain is indicated by a solid black bar. CDRs are indicated by open bars. DNA sequences include cloning sites and Kozak sequences (upstream of coding sequences) and splice and cloning sequences (downstream).

Figure 5A:
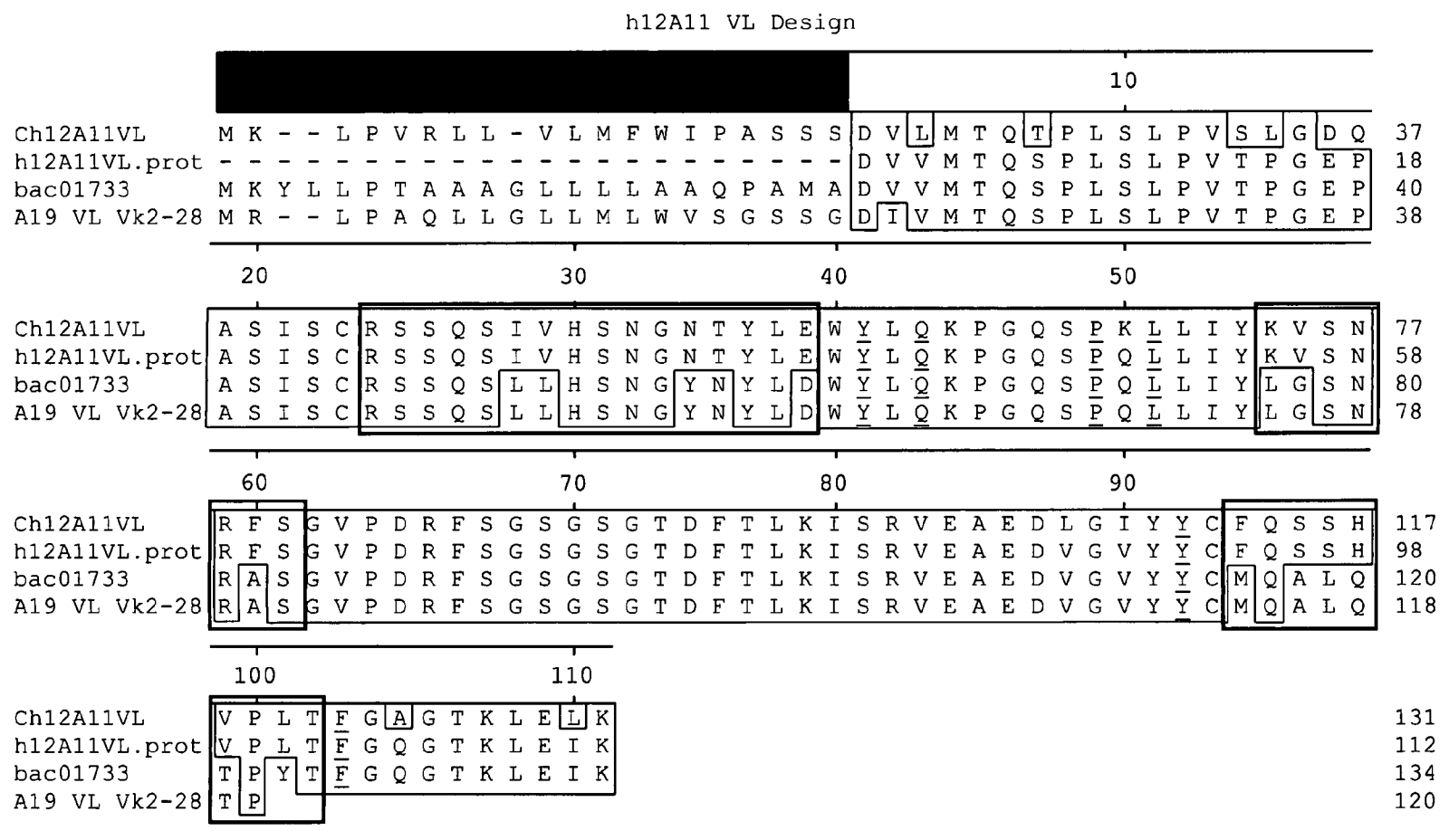
Figure 5B:
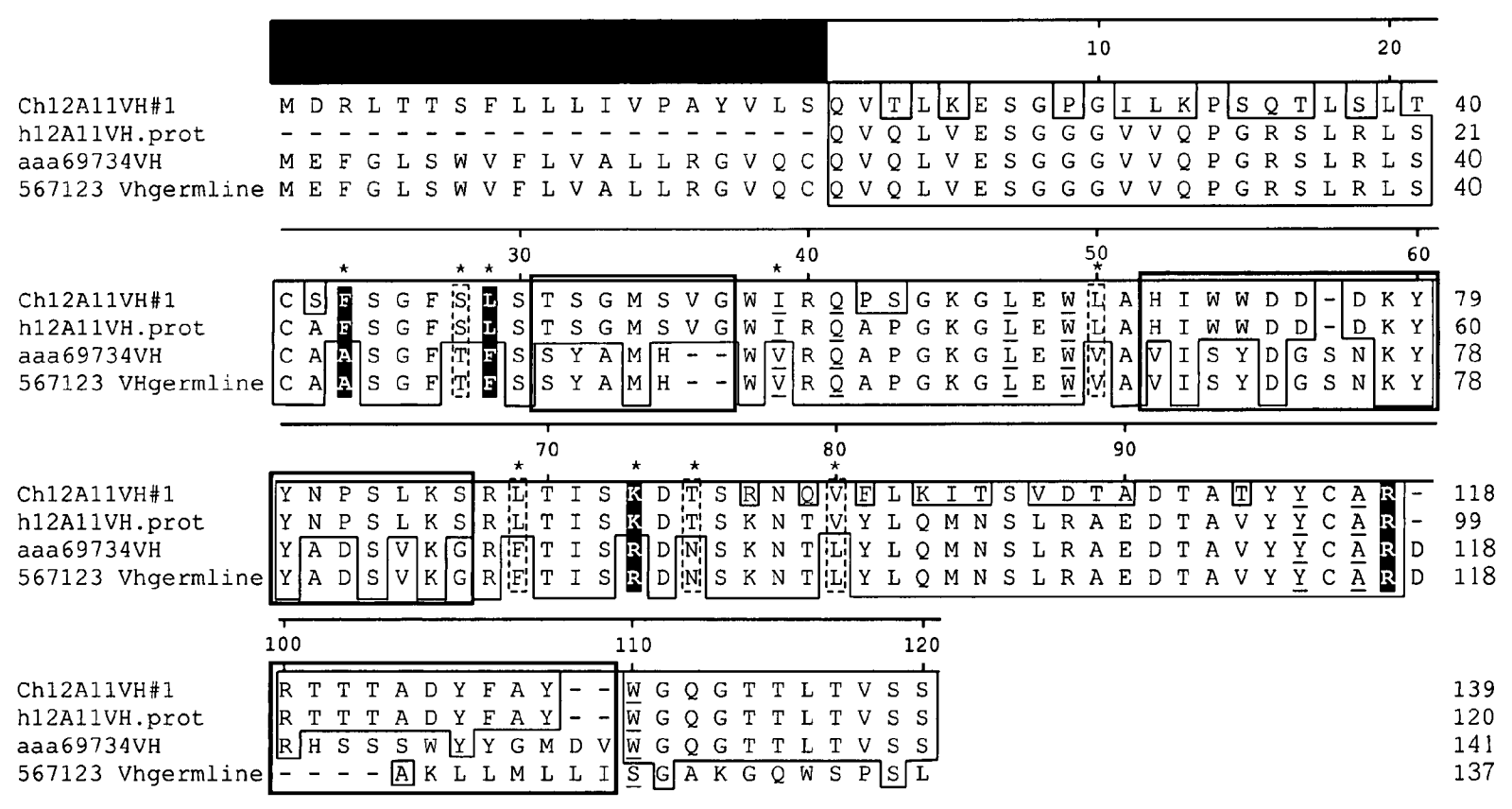

FIG. 5A depicts an alignment of the amino acid sequences of the light chain of murine (or chimeric) 12A11 (SEQ ID NO:2), humanized 12A11 (mature peptide, SEQ ID NO:7), GenBank BAC01733 (SEQ ID NO: 8) and germline A19 (X63397, SEQ ID NO: 9) antibodies. CDR regions are boxed. Packing residues are underlined. Numbered from the first methionine, not Kabat numbering. FIG. 5B depicts an alignment of the amino acid sequences of the heavy chain of murine (or chimeric) 12A11 (SEQ ID NO:4), humanized 12aA11 (version 1) (mature peptide, SEQ ID NO:10), GenBank AAA69734 (SEQ ID NO:11), and germline GenBank 567123 antibodies (SEQ ID NO:12). Packing residues are underlined, canonical residues are in solid fill and vernier residues are in dotted fill. Numbered from the first methionine, not Kabat numbering.

FIG. 6A-B depicts an alignment of the amino acid sequences of the heavy chains of humanized 12A11 v1 (SEQ ID NO:10), v2 (SEQ ID NO:13), v2.1 (SEQ ID NO:14), v3 (SEQ ID NO:15), v4.1 (SEQ ID NO:16), v4.2 (SEQ ID NO:17), v4.3 (SEQ ID NO:18), v4.4 (SEQ ID NO:19), v5.1 (SEQ ID NO:20), v5.2 (SEQ ID NO:21), v5.3 (SEQ ID NO:22), v5.4 (SEQ ID NO:23), v5.5 (SEQ ID NO:24), v5.6 (SEQ ID NO:25), v6.1 (SEQ ID NO:26), v6.2 (SEQ ID NO:27), v6.3 (SEQ ID NO:28), v6.4 (SEQ ID NO:29), v7 (SEQ ID NO:30) and v8 (SEQ ID NO:31). FIG. 6C sets forth the backmutations made in humanized 12A11 v1 to v8.

FIG. 7 depicts the results from an aggregated Aβ (1-42) ELISA comparing chimeric 12A11, humanized 12A11 v1, humanized 12A11 v2, humanized 12A11 v2.1, and humanized 12A11 v3.

FIG. 8 depicts the results of a competitive Aβ 1-42 ELISA binding assay comparing murine 12A11, chimeric 12A11 and 12A11 v1.

DETAILED DESCRIPTION OF THE INVENTION

Figure 3A:
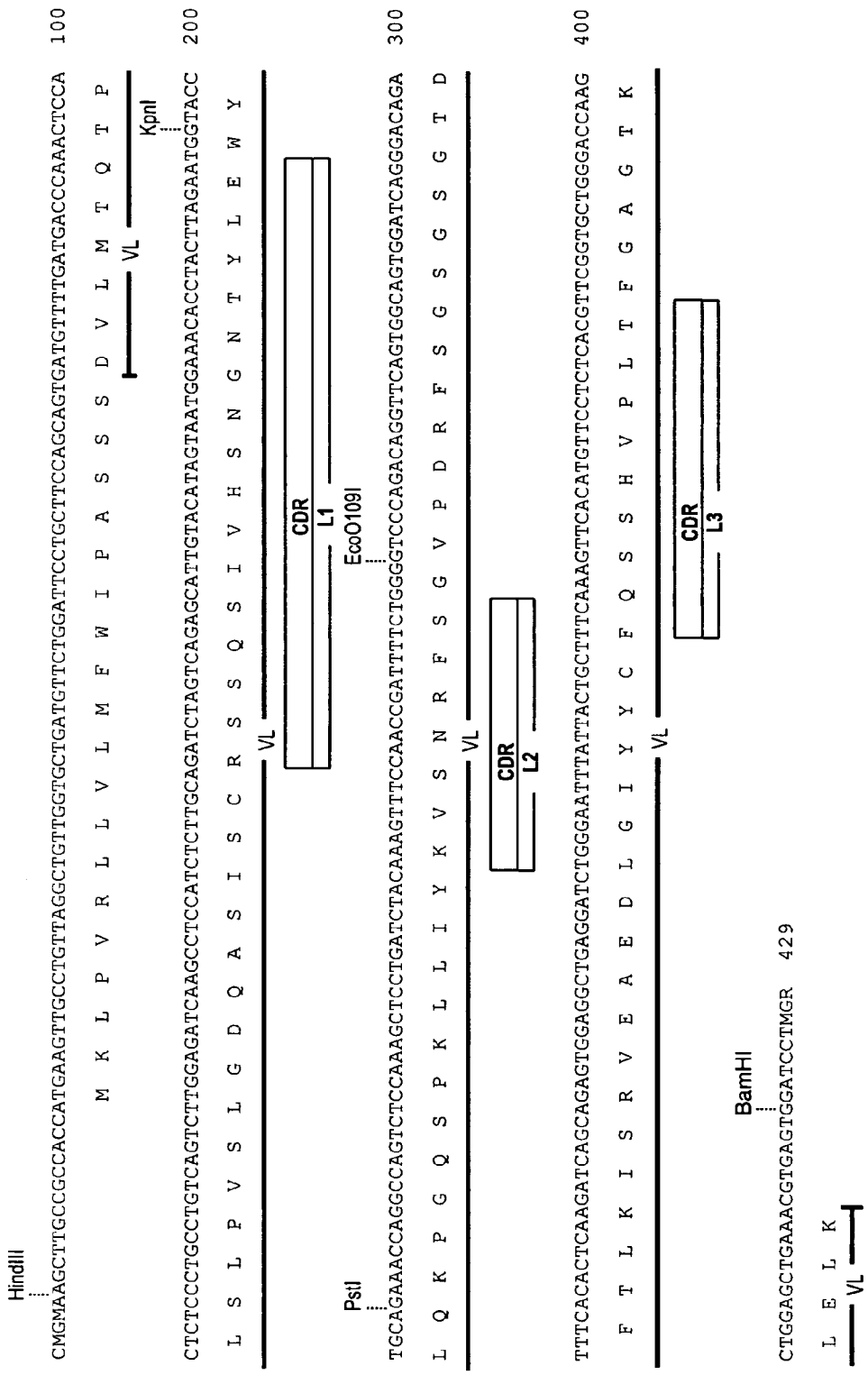
FIG. 3A depicts a DNA sequence including the murine 12A11 VL chain sequence and the deduced amino acid sequence for the VL chain (SEQ ID NOs: 5 and 2, respectively). Mature VL chain is indicated by a solid black bar. CDRs are indicated by open bars.

The present invention features new immunological reagents and methods for preventing or treating Alzheimer's disease or other amyloidogenic diseases. The invention is based, at least in part, on the characterization of a monoclonal immunoglobulin, 12A11, effective at binding beta amyloid protein (Aβ) (e.g., binding soluble and/or aggregated Aβ), mediating phagocytosis (e.g., of aggregated Aβ), reducing plaque burden and/or reducing neuritic dystrophy (e.g., in a patient). The invention is further based on the determination and structural characterization of the primary and secondary structure of the variable light and heavy chains of the 12A11 immunoglobulin and the identification of residues important for activity and immunogenicity.

Immunoglobulins are featured which include a variable light and/or variable heavy chain of the 12A11 monoclonal immunoglobulin described herein. Preferred immunoglobulins, e.g., therapeutic immunoglobulins, are featured which include a humanized variable light and/or humanized variable heavy chain. Preferred variable light and/or variable heavy chains include a complementarity determining region (CDR) from the 12A11 immunoglobulin (e.g., donor immunoglobulin) and variable framework regions from or substantially from a human acceptor immunoglobulin. The phrase "substantially from a human acceptor immunoglobulin" means that the majority or key framework residues are from the human acceptor sequence, allowing however, for substitution of residues at certain positions with residues selected to improve activity of the humanized immunoglobulin (e.g., alter activity such that it more closely mimics the activity of the donor immunoglobulin) or selected to decrease the immunogenicity of the humanized immunoglobulin.

In one embodiment, the invention features a humanized immunoglobulin light or heavy chain that includes 12A11 variable region complementarity determining regions (CDRs) (i.e., includes one, two or three CDRs from the light chain variable region sequence set forth as SEQ ID NO:2 or includes one, two or three CDRs from the heavy chain variable region sequence set forth as SEQ ID NO:4), and includes a variable framework region from a human acceptor immunoglobulin light or heavy chain sequence, optionally having at least one residue of the framework residue backmutated to a corresponding murine residue, wherein said backmutation does not substantially affect the ability of the chain to direct Aβ binding.

In one embodiment, the invention features a humanized immunoglobulin light or heavy chain that includes 12A11 variable region complementarity determining regions (CDRs) (i.e., includes one, two or three CDRs from the light chain variable region sequence set forth as SEQ ID NO:2 or includes one, two or three CDRs from the heavy chain variable region sequence set forth as SEQ ID NO:4), and includes a variable framework region substantially from a human acceptor immunoglobulin light or heavy chain sequence, optionally having at least one residue of the framework residue backmutated to a corresponding murine residue, wherein said backmutation does not substantially affect the ability of the chain to direct Aβ binding.

In another embodiment, the invention features a humanized immunoglobulin light or heavy chain that includes 12A11 variable region complementarity determining regions (CDRs) (e.g., includes one, two or three CDRs from the light chain variable region sequence set forth as SEQ ID NO:2 and/or includes one, two or three CDRs from the heavy chain variable region sequence set forth as SEQ ID NO:4), and includes a variable framework region substantially from a human acceptor immunoglobulin light or heavy chain sequence, optionally having at least one framework residue substituted with the corresponding amino acid residue from the mouse 12A11 light or heavy chain variable region sequence, where the framework residue is selected from the group consisting of (a) a residue that non-covalently binds antigen directly; (b) a residue adjacent to a CDR; (c) a CDR-interacting residue (e.g., identified by modeling the light or heavy chain on the solved structure of a homologous known immunoglobulin chain); and (d) a residue participating in the VL-VH interface.

In another embodiment, the invention features a humanized immunoglobulin light or heavy chain that includes 12A11 variable region CDRs and variable framework regions from a human acceptor immunoglobulin light or heavy chain sequence, optionally having at least one framework residue substituted with the corresponding amino acid residue from the mouse 12A11 light or heavy chain variable region sequence, where the framework residue is a residue capable of affecting light chain variable region conformation or function as identified by analysis of a three-dimensional model of the variable region, for example a residue capable of interacting with antigen, a residue proximal to the antigen binding site, a residue capable of interacting with a CDR, a residue adjacent to a CDR, a residue within 6 Å of a CDR residue, a canonical residue, a vernier zone residue, an interchain packing residue, an unusual residue, or a glycosylation site residue on the surface of the structural model.

In another embodiment, the invention features, in addition to the substitutions described above, a substitution of at least one rare human framework residue. For example, a rare residue can be substituted with an amino acid residue which is common for human variable chain sequences at that position. Alternatively, a rare residue can be substituted with a corresponding amino acid residue from a homologous germline variable chain sequence.

In another embodiment, the invention features a humanized immunoglobulin that includes a light chain and a heavy chain, as described above, or an antigen-binding fragment of said immunoglobulin. In an exemplary embodiment, the humanized immunoglobulin binds (e.g., specifically binds) to beta amyloid peptide (Aβ) with a binding affinity of at least $10^7$ M$^{-1}$, $10^8$ M$^{-1}$, or $10^9$ M$^{-1}$. In another embodiment, the immunoglobulin or antigen binding fragment includes a heavy chain having isotype γ1. In another embodiment, the immunoglobulin or antigen binding fragment binds (e.g., specifically binds) to either or both soluble beta amyloid peptide (Aβ) and aggregated Aβ. In another embodiment, the immunoglobulin or antigen binding fragment captures soluble Aβ (e.g., soluble Aβ1-42). In another embodiment, the immunoglobulin or antigen binding fragment mediates phagocytosis (e.g., induces phagocytosis) of beta amyloid peptide (Aβ). In yet another embodiment, the immunoglobulin or antigen binding fragment-crosses the blood-brain barrier in a subject. In yet another embodiment, the immunoglobulin or antigen binding fragment reduces either or both beta amyloid peptide (Aβ) burden and neuritic dystrophy in a subject.

In another embodiment, the invention features chimeric immunoglobulins that include 12A11 variable regions (e.g., the variable region sequences set forth as SEQ ID NO:2 or SEQ ID NO:4). In yet another embodiment, the immunoglobulin, or antigen-binding fragment thereof, further includes constant regions from IgG1.

The immunoglobulins described herein are particularly suited for use in therapeutic methods aimed at preventing or treating amyloidogenic diseases. In one embodiment, the invention features a method of preventing or treating an amyloidogenic disease (e.g., Alzheimer's disease) that involves administering to the patient an effective dosage of a humanized immunoglobulin as described herein. In another embodiment, the invention features pharmaceutical compositions that include a humanized immunoglobulin as described herein and a pharmaceutical carrier. Also featured are isolated nucleic acid molecules, vectors and host cells for producing the immunoglobulins or immunoglobulin fragments or chains described herein, as well as methods for producing said immunoglobulins, immunoglobulin fragments or immunoglobulin chains.

The present invention further features a method for identifying 12A11 residues amenable to substitution when producing a humanized 12A11 immunoglobulin, respectively. For example, a method for identifying variable framework region residues amenable to substitution involves modeling the three-dimensional structure of a 12A11 variable region on a solved homologous immunoglobulin structure and analyzing said model for residues capable of affecting 12A11 immunoglobulin variable region conformation or function, such that residues amenable to substitution are identified. The invention further features use of the variable region sequence set forth as SEQ ID NO:2 or SEQ ID NO:4, or any portion thereof, in producing a three-dimensional image of a 12A11 immunoglobulin, 12A11 immunoglobulin chain, or domain thereof.

The present invention further features immunoglobulins having altered effector function, such as the ability to bind effector molecules, for example, complement or a receptor on an effector cell. In particular, the immunoglobulin of the invention has an altered constant region, e.g., Fc region, wherein at least one amino acid residue in the Fc region has been replaced with a different residue or side chain. In one embodiment, the modified immunoglobulin is of the IgG class, comprises at least one amino acid residue replacement in the Fc region such that the immunoglobulin has an altered effector function, e.g., as compared with an unmodified immunoglobulin. In particular embodiments, the immunoglobulin of the invention has an altered effector function such that it is less immunogenic (e.g., does not provoke undesired effector cell activity, lysis, or complement binding), has improved amyloid clearance properties, and/or has a desirable half-life.

Prior to describing the invention, it may be helpful to an understanding thereof to set forth definitions of certain terms to be used hereinafter.

The term "immunoglobulin" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains).

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

Immunoglobulins or antibodies can exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i.e., specific binding).

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

"Specific binding" of an antibody means that the antibody exhibits appreciable affinity for a particular antigen or epitope and, generally, does not exhibit significant crossreactivity. In exemplary embodiments, the antibody exhibits no crossreactivity (e.g., does not crossreact with non-Aβ peptides or with remote epitopes on Aβ). "Appreciable" or preferred binding includes binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^{-1}$. An antibody that "does not exhibit significant crossreactivity" is one that will not appreciably bind to an undesirable entity (e.g., an undesirable proteinaceous entity). For example, an antibody that specifically binds to Aβ will appreciably bind Aβ but will not significantly react with non-Aβ proteins or peptides (e.g., non-Aβ proteins or peptides included in plaques). An antibody specific for a particular epitope will, for example, not significantly crossreact with remote epitopes on the same protein or peptide. Specific binding can be determined according to any art-recognized means for determining such binding. Preferably, specific binding is determined according to Scatchard analysis and/or competitive binding assays.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino sequence for comparison purposes, the region shares at least 80-90%, 90-95%, or 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably at least 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The term "significant identity" means that two polypeptide sequences, when optimally aligned, such as by the programs GAP™ or BESTFIT™ using default gap weights, share at least 50-60% sequence identity, preferably at least 60-70% sequence identity, more preferably at least 70-80% sequence identity, more preferably at least 80-90% identity, even more preferably at least 90-95% identity, and even more preferably at least 95% sequence identity or more (e.g., 99% sequence identity or more). The term "substantial identity" means that two polypeptide sequences, when optimally aligned, such as by the programs GAP™ or BESTFIT™ using default gap weights, share at least 80-90% sequence identity, preferably at least 90-95% sequence identity, and more preferably at least 95% sequence identity or more (e.g., 99% sequence identity or more). For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP™, BESTFIT™, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of algorithm that is suitable for determining percent sequence identity and sequence similarity is the BLAST™ algorithm, which is described in Altschul et al., *J. Mol. Biol.* 215:403 (1990). Software for performing BLAST™ analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

Preferably, residue positions which are not identical differ by conservative amino acid substitutions. For purposes of classifying amino acids substitutions as conservative or non-conservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Preferably, humanized immunoglobulins or antibodies bind antigen with an affinity that is within a factor of three, four, or five of that of the corresponding nonhumanized antibody. For example, if the nonhumanized antibody has a binding affinity of $10^9$ $M^{-1}$, humanized antibodies will have a binding affinity of at least $3 \times 10^9$ $M^{-1}$, $4 \times 10^9$ $M^{-1}$ or $5 \times 10^9$ $M^{-1}$. When describing the binding properties of an immunoglobulin or antibody chain, the chain can be described based on its ability to "direct antigen (e.g., Aβ) binding". A chain is said to "direct antigen binding" when it confers upon an intact immunoglobulin or antibody (or antigen binding fragment thereof) a specific binding property or binding affinity. A mutation (e.g., a backmutation) is said to substantially affect the ability of a heavy or light chain to direct antigen binding if it affects (e.g., decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (e.g., decrease) the ability of a chain to direct antigen binding" if it affects (e.g., decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species. The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

An "antigen" is an entity (e.g., a proteinaceous entity or peptide) to which an antibody specifically binds.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, G. E. Morris, Ed. (1996).

Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

Exemplary epitopes or antigenic determinants can be found within the human amyloid precursor protein (APP), but are preferably found within the Aβ peptide of APP. Multiple isoforms of APP exist, for example APP$^{695}$ APP$^{751}$ and APP$^{770}$. Amino acids within APP are assigned numbers according to the sequence of the APP$^{770}$ isoform (see e.g., GenBank Accession No. P05067). Aβ (also referred to herein as beta amyloid peptide and A-beta) peptide is an approximately 4-kDa internal fragment of 39-43 amino acids of APP (Aβ39, Aβ40, Aβ41, Aβ42 and Aβ43). Aβ40, for example, consists of residues 672-711 of APP and Aβ42 consists of residues 673-713 of APP. As a result of proteolytic processing of APP by different secretase enzymes iv vivo or in situ, Aβ is found in both a "short form", 40 amino acids in length, and a "long form", ranging from 42-43 amino acids in length. Preferred epitopes or antigenic determinants, as described herein, are located within the N-terminus of the Aβ peptide and include residues within amino acids 1-10 of Aβ, preferably from residues 1-3, 1-4, 1-5, 1-6, 1-7 or 3-7 of Aβ42. Additional referred epitopes or antigenic determinants include residues 2-4, 5, 6, 7 or 8 of Aβ, residues 3-5, 6, 7, 8 or 9 of Aβ, or residues 4-7, 8, 9 or 10 of Aβ42. When an antibody is said to bind to an epitope within specified residues, such as Aβ 3-7, what is meant is that the antibody specifically binds to a polypeptide containing the specified residues (i.e., Aβ 3-7 in this an example). Such an antibody does not necessarily contact every residue within Aβ3-7. Nor does every single amino acid substitution or deletion with in Aβ 3-7 necessarily significantly affect binding affinity.

The term "amyloidogenic disease" includes any disease associated with (or caused by) the formation or deposition of insoluble amyloid fibrils. Exemplary amyloidogenic diseases include, but are not limited to systemic amyloidosis, Alzheimer's disease, mature onset diabetes, Parkinson's disease, Huntington's disease, fronto-temporal dementia, and the prion-related transmissible spongiform encephalopathies (kuru and Creutzfeldt-Jacob disease in humans and scrapie and BSE in sheep and cattle, respectively). Different amyloidogenic diseases are defined or characterized by the nature of the polypeptide component of the fibrils deposited. For example, in subjects or patients having Alzheimer's disease, β-amyloid protein (e.g., wild-type, variant, or truncated β-amyloid protein) is the characterizing polypeptide component of the amyloid deposit. Accordingly, Alzheimer's disease is an example of a "disease characterized by deposits of Aβ" or a "disease associated with deposits of Aβ", e.g., in the brain of a subject or patient. The terms "β-amyloid protein", "β-amyloid peptide", "β-amyloid", "Aβ" and "Aβ peptide" are used interchangeably herein.

An "immunogenic agent" or "immunogen" is capable of inducing an immunological response against itself on administration to a mammal, optionally in conjunction with an adjuvant.

The term "treatment" as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the patient's own immune system.

The term "patient" includes human and other mammalian subjects that receive either prophylactic or therapeutic treatment.

"Soluble" or "dissociated" Aβ refers to non-aggregating or disaggregated Aβ polypeptide, including monomeric soluble as well as oligomeric soluble Aβ polypeptide (e.g., soluble Aβ dimers, trimers, and the like). "Insoluble" Aβ refers to aggregating Aβ polypeptide, for example, Aβ held together by noncovalent bonds. Aβ (e.g., Aβ42) is believed to aggregate, at least in part, due to the presence of hydrophobic residues at the C-terminus of the peptide (part of the transmembrane domain of APP). Soluble Aβ can be found in vivo in biological fluids such as cerebrospinal fluid and/or serum. Alternatively, soluble Aβ can be prepared by dissolving lyophilized peptide in neat DMSO with sonication. The resulting solution is centrifuged (e.g., at 14,000×g, 4° C., 10 minutes) to remove any insoluble particulates.

The term "effector function" refers to an activity that resides in the Fc region of an antibody (e.g., an IgG antibody) and includes, for example, the ability of the antibody to bind effector molecules such as complement and/or Fc receptors, which can control several immune functions of the antibody such as effector cell activity, lysis, complement-mediated activity, antibody clearance, and antibody half-life.

The term "effector molecule" refers to a molecule that is capable of binding to the Fc region of an antibody (e.g., an IgG antibody) including, but not limited to, a complement protein or a Fc receptor.

The term "effector cell" refers to a cell capable of binding to the Fc portion of an antibody (e.g., an IgG antibody) typically via an Fc receptor expressed on the surface of the effector cell including, but not limited to, lymphocytes, e.g., antigen presenting cells and T cells.

The term "Fc region" refers to a C-terminal region of an IgG antibody, in particular, the C-terminal region of the heavy chain(s) of said IgG antibody. Although the boundaries of the Fc region of an IgG heavy chain can vary slightly, a Fc region is typically defined as spanning from about amino acid residue Cys226 to the carboxyl-terminus of an IgG heavy chain(s).

The term "Kabat numbering" unless otherwise stated, is defined as the numbering of the residues in, e.g., an IgG heavy chain antibody using the EU index as in Kabat et al. (Sequences of Proteins of Immunological Interest, 5th Ed. Public Health Service, National Institutes of Health, Bethesda, Md. (1991)), expressly incorporated herein by reference.

The term "Fc receptor" or "FcR" refers to a receptor that binds to the Fc region of an antibody. Typical Fc receptors which bind to an Fc region of an antibody (e.g., an IgG antibody) include, but are not limited to, receptors of the FcγRI, FcγRII, and FcγRIII subclasses, including allelic variants and alternatively spliced forms of these receptors. Fc receptors are reviewed in Ravetch and Kinet, Annu. Rev.

Immunol 9:457-92 (1991); Capel et al., Immunomethods 4:25-34 (1994); and de Haas et al., J. Lab. Clin. Med. 126: 330-41 (1995).

I. Immunological and Therapeutic Reagents

Immunological and therapeutic reagents of the invention comprise or consist of immunogens or antibodies, or functional or antigen binding fragments thereof, as defined herein. The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda and are about 230 residues in length. Heavy chains are classified as gamma ($\gamma$), mu ($\mu$), alpha ($\alpha$), delta ($\delta$), or epsilon ($\epsilon$), are about 450-600 residues in length, and define the antibody's isotype as IgG, IgM, IgA, IgD and IgE, respectively. Both heavy and light chains are folded into domains. The term "domain" refers to a globular region of a protein, for example, an immunoglobulin or antibody. Immunoglobulin or antibody domains include, for example, three or four peptide loops stabilized by $\beta$-pleated sheet and an interchain disulfide bond. Intact light chains have, for example, two domains ($V_L$ and $C_L$) and intact heavy chains have, for example, four or five domains ($V_H$, $C_H1$, $C_H2$, and $C_H3$).

Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y. (1989), Ch. 7, incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. Naturally-occurring chains or recombinantly produced chains can be expressed with a leader sequence which is removed during cellular processing to produce a mature chain. Mature chains can also be recombinantly produced having a non-naturally occurring leader sequence, for example, to enhance secretion or alter the processing of a particular chain of interest.

The CDRs of the two mature chains of each pair are aligned by the framework regions, enabling binding to a specific epitope. From N-terminal to C-terminal, both light and heavy chains comprise the domains FR1, CDR1, FR2, CDR2, FR3, CDR3 and FR4. "FR4" also is referred to in the art as the D/J region of the variable heavy chain and the J region of the variable light chain. The assignment of amino acids to each domain is in accordance with the definitions of Kabat, *Sequences of Proteins of Immunological Interest* (National Institutes of Health, Bethesda, Md., 1987 and 1991). An alternative structural definition has been proposed by Chothia et al., *J. Mol. Biol.* 196:901 (1987); *Nature* 342:878 (1989); and *J. Mol. Biol.* 186:651 (1989) (hereinafter collectively referred to as "Chothia et al." and incorporated by reference in their entirety for all purposes).

A. A$\beta$ Antibodies

Therapeutic agents of the invention include antibodies that specifically bind to A$\beta$ or to other components of the amyloid plaque. Preferred antibodies are monoclonal antibodies. Some such antibodies bind specifically to the aggregated form of A$\beta$ without binding to the soluble form. Some bind specifically to the soluble form without binding to the aggregated form. Some bind to both aggregated and soluble forms. Antibodies used in therapeutic methods preferably have an intact constant region or at least sufficient of the constant region to interact with an Fc receptor. Preferred antibodies are those efficacious at stimulating Fc-mediated phagocytosis of A$\beta$ in plaques. Human isotype IgG1 is preferred because of it having highest affinity of human isotypes for the FcRI receptor on phagocytic cells (e.g., on brain resident macrophages or microglial cells). Human IgG1 is the equivalent of murine IgG2a, the latter thus suitable for testing in vivo efficacy in animal (e.g., mouse) models of Alzheimer's. Bispecific Fab fragments can also be used, in which one arm of the antibody has specificity for A$\beta$, and the other for an Fc receptor. Preferred antibodies bind to A$\beta$ with a binding affinity greater than (or equal to) about $10^6$, $10^7$, $10^8$, $10^9$, or $10^{10}$ $M^{-1}$ (including affinities intermediate of these values).

Monoclonal antibodies bind to a specific epitope within A$\beta$ that can be a conformational or nonconformational epitope. Prophylactic and therapeutic efficacy of antibodies can be tested using the transgenic animal model procedures described in the Examples. Preferred monoclonal antibodies bind to an epitope within residues 1-10 of A$\beta$ (with the first N terminal residue of natural A$\beta$ designated 1), more preferably to an epitope within residues 3-7 of A$\beta$. In some methods, multiple monoclonal antibodies having binding specificities to different epitopes are used, for example, an antibody specific for an epitope within residues 3-7 of A$\beta$ can be co-administered with an antibody specific for an epitope outside of residues 3-7 of A$\beta$. Such antibodies can be administered sequentially or simultaneously. Antibodies to amyloid components other than A$\beta$ can also be used (e.g., administered or co-administered).

Epitope specificity of an antibody can be determined, for example, by forming a phage display library in which different members display different subsequences of A$\beta$. The phage display library is then selected for members specifically binding to an antibody under test. A family of sequences is isolated. Typically, such a family contains a common core sequence, and varying lengths of flanking sequences in different members. The shortest core sequence showing specific binding to the antibody defines the epitope bound by the antibody. Antibodies can also be tested for epitope specificity in a competition assay with an antibody whose epitope specificity has already been determined. For example, antibodies that compete with the 12A11 antibody for binding to A$\beta$ bind to the same or similar epitope as 12A11, i.e., within residues A$\beta$ 3-7. Screening antibodies for epitope specificity is a useful predictor of therapeutic efficacy. For example, an antibody determined to bind to an epitope within residues 1-7 of A$\beta$ is likely to be effective in preventing and treating Alzheimer's disease according to the methodologies of the present invention.

Antibodies that specifically bind to a preferred segment of A$\beta$ without binding to other regions of A$\beta$ have a number of advantages relative to monoclonal antibodies binding to other regions or polyclonal sera to intact A$\beta$. First, for equal mass dosages, dosages of antibodies that specifically bind to preferred segments contain a higher molar dosage of antibodies effective in clearing amyloid plaques. Second, antibodies specifically binding to preferred segments can induce a clearing response against amyloid deposits without inducing a clearing response against intact APP polypeptide, thereby reducing the potential side effects.

1. Production of Nonhuman Antibodies

The present invention features non-human antibodies, for example, antibodies having specificity for the preferred Aβ epitopes of the invention. Such antibodies can be used in formulating various therapeutic compositions of the invention or, preferably, provide complementarity determining regions for the production of humanized or chimeric antibodies (described in detail below). The production of non-human monoclonal antibodies, e.g., murine, guinea pig, primate, rabbit or rat, can be accomplished by, for example, immunizing the animal with Aβ. A longer polypeptide comprising Aβ or an immunogenic fragment of Aβ or anti-idiotypic antibodies to an antibody to Aβ can also be used. See Harlow & Lane, supra, incorporated by reference for all purposes). Such an immunogen can be obtained from a natural source, by peptide synthesis or by recombinant expression. Optionally, the immunogen can be administered fused or otherwise complexed with a carrier protein, as described below. Optionally, the immunogen can be administered with an adjuvant. The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages. Several types of adjuvant can be used as described below. Complete Freund's adjuvant followed by incomplete adjuvant is preferred for immunization of laboratory animals.

Rabbits or guinea pigs are typically used for making polyclonal antibodies. Exemplary preparation of polyclonal antibodies, e.g., for passive protection, can be performed as follows. 125 non-transgenic mice are immunized with 100 µg Aβ 1-42, plus CFA/IFA adjuvant, and euthanized at 4-5 months. Blood is collected from immunized mice. IgG is separated from other blood components. Antibody specific for the immunogen may be partially purified by affinity chromatography. An average of about 0.5-1 mg of immunogen-specific antibody is obtained per mouse, giving a total of 60-120 mg.

Mice are typically used for making monoclonal antibodies. Monoclonals can be prepared against a fragment by injecting the fragment or longer form of Aβ into a mouse, preparing hybridomas and screening the hybridomas for an antibody that specifically binds to Aβ. Optionally, antibodies are screened for binding to a specific region or desired fragment of Aβ without binding to other nonoverlapping fragments of Aβ. The latter screening can be accomplished by determining binding of an antibody to a collection of deletion mutants of an Aβ peptide and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to Aβ. If the test and reference antibodies compete, then they bind to the same epitope or epitopes sufficiently proximal such that binding of one antibody interferes with binding of the other. The preferred isotype for such antibodies is mouse isotype IgG2a or equivalent isotype in other species. Mouse isotype IgG2a is the equivalent of human isotype IgG1 (e.g., human IgG1).

2. Chimeric and Humanized Antibodies

The present invention also features chimeric and/or humanized antibodies (i.e., chimeric and/or humanized immunoglobulins) specific for beta amyloid peptide. Chimeric and/or humanized antibodies have the same or similar binding specificity and affinity as a mouse or other nonhuman antibody that provides the starting material for construction of a chimeric or humanized antibody.

a. Production of Chimeric Antibodies

The term "chimeric antibody" refers to an antibody whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. A typical chimeric antibody is thus a hybrid protein consisting of the V or antigen-binding domain from a mouse antibody and the C or effector domain from a human antibody.

b. Production of Humanized Antibodies

The term "humanized antibody" refers to an antibody comprising at least one chain comprising variable region framework residues substantially from a human antibody chain (referred to as the acceptor immunoglobulin or antibody) and at least one complementarity determining region substantially from a mouse antibody, (referred to as the donor immunoglobulin or antibody). See, Queen et al., *Proc. Natl. Acad. Sci. USA* 86:10029-10033 (1989), U.S. Pat. No. 5,530,101, U.S. Pat. No. 5,585,089, U.S. Pat. No. 5,693,761, U.S. Pat. No. 5,693,762, Selick et al., WO 90/07861, and Winter, U.S. Pat. No. 5,225,539 (incorporated by reference in their entirety for all purposes). The constant region(s), if present, are also substantially or entirely from a human immunoglobulin.

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., *Protein Engineering* 4:773 (1991); Kolbinger et al., *Protein Engineering* 6:971 (1993) and Carter et al., WO 92/22653.

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE™) and/or solid-phase ELISA analysis.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution is determined, in part, by computer modeling. Computer hardware and software are described herein for producing three-dimensional images of immunoglobulin molecules. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g., is within about 3-6 Å of a CDR region as determined by computer modeling), or
(4) participates in the VL-VH interface.

Residues which "noncovalently bind antigen directly" include amino acids in positions in framework regions which have a good probability of directly interacting with amino acids on the antigen according to established chemical forces, for example, by hydrogen bonding, Van der Waals forces, hydrophobic interactions, and the like.

CDR and framework regions are as defined by Kabat et al. or Chothia et al., supra. When framework residues, as defined by Kabat et al., supra, constitute structural loop residues as defined by Chothia et al., supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk JMB 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233: 747 (1986), which is incorporated herein by reference) and selecting these amino acids from the donor may be desirable to keep all the antigen contacts that provide affinity in the original antibody.

Residues that "otherwise interact with a CDR region" include those that are determined by secondary structural analysis to be in a spatial orientation sufficient to affect a CDR region. In one embodiment, residues that "otherwise interact with a CDR region" are identified by analyzing a three-dimensional model of the donor immunoglobulin (e.g., a computer-generated model). A three-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units (Å) of some atom in the CDRs and must contain an atom that could interact with the CDR atoms according to established chemical forces, such as those listed above.

In the case of atoms that may form a hydrogen bond, the 3 Å is measured between their nuclei, but for atoms that do not form a bond, the 3 Å is measured between their Van der Waals surfaces. Hence, in the latter case, the nuclei must be within about 6 Å (3 Å plus the sum of the Van der Waals radii) for the atoms to be considered capable of interacting. In many cases the nuclei will be from 4 or 5 to 6 Å apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids that are capable of interacting with amino acids in the CDRs, may be identified in yet another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an antibody, using algorithms known in the art (e.g., Connolly, J. Appl. Cryst. 16:548 (1983) and Lee and Richards, J. Mol. Biol. 55:379 (1971), both of which are incorporated herein by reference). Framework amino acids may also occasionally interact with the CDRs indirectly, by affecting the conformation of another framework amino acid that in turn contacts the CDRs.

The amino acids at several positions in the framework are known to be important for determining CDR confirmation (e.g., capable of interacting with the CDRs) in many antibodies (Chothia and Lesk, supra, Chothia et al., supra and Tramontano et al., J. Mol. Biol. 215:175 (1990), all of which are incorporated herein by reference). These authors identified conserved framework residues important for CDR conformation by analysis of the structures of several known antibodies. The antibodies analyzed fell into a limited number of structural or "canonical" classes based on the conformation of the CDRs. Conserved framework residues within members of a canonical class are referred to as "canonical" residues. Canonical residues include residues 2, 25, 29, 30, 33, 48, 64, 71, 90, 94 and 95 of the light chain and residues 24, 26, 29, 34, 54, 55, 71 and 94 of the heavy chain. Additional residues (e.g., CDR structure determining residues) can be identified according to the methodology of Martin and Thorton (1996) *J. Mol. Biol.* 263:800. Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. Additional residues which may effect conformation of the CDRs can be identified according to the methodology of Foote and Winter (1992) *J. Mol. Biol.* 224:487. Such residues are termed "vernier" residues and are those residues in the framework region closely underlying (i.e., forming a "platform" tinder) the CDRs. At all these numbered positions, choice of the donor amino acid rather than the acceptor amino acid (when they differ) to be in the humanized immunoglobulin is preferred. On the other hand, certain residues capable of interacting with the CDR region, such as the first 5 amino acids of the light chain, may sometimes be chosen from the acceptor immunoglobulin without loss of affinity in the humanized immunoglobulin.

Residues which "participate in the VL-VH interface" or "packing residues" include those residues at the interface between VL and VH as defined, for example, by Novotny and Haber, Proc. Natl. Acad. Sci. USA, 82:4592-66 (1985) or Chothia et al, supra. Generally, unusual packing residues should be retained in the humanized antibody if they differ from those in the human frameworks.

In general, one or more of the amino acids fulfilling the above criteria can be substituted. In some embodiments, all or most of the amino acids fulfilling the above criteria are substituted. Occasionally, there is some ambiguity about whether a particular amino acid meets the above criteria, and alternative variant immunoglobulins are produced, one of which has that particular substitution, the other of which does not. Alternative variant immunoglobulins so produced can be tested in any of the assays described herein for the desired activity, and the preferred immunoglobulin selected.

Usually the CDR regions in humanized antibodies are substantially identical, and more usually, identical to the corresponding CDR regions of the donor antibody. However, in certain embodiments, it may be desirable to modify one or more CDR regions to modify the antigen binding specificity of the antibody and/or reduce the immunogenicity of the antibody. Typically, one or more residues of a CDR are altered to modify binding to achieve a more favored on-rate of binding, a more favored off-rate of binding, or both, such that an idealized binding constant is achieved. Using this strategy, an antibody having ultra high binding affinity of, for example, $10^{10}$ $M^{-1}$ or more, can be achieved. Briefly, the donor CDR sequence is referred to as a base sequence from which one or more residues are then altered. Affinity maturation techniques, as described herein, can be used to alter the CDR region(s) followed by screening of the resultant binding molecules for the desired change in binding. The method may also be used to alter the donor CDR, typically a mouse CDR, to be less immunogenic such that a potential human antimouse antibody (HAMA) response is minimized or avoided. Accordingly, as CDR(s) are altered, changes in binding affinity as well as immunogenicity can be monitored and scored such that an antibody optimized for the best combined binding and low immunogenicity are achieved (see, e.g., U.S. Pat. No. 6,656,467 and U.S. Pat. Pub. US20020164326A1).

In another approach, the CDR regions of the antibody are analyzed to determine the contributions of each individual CDR to antibody binding and/or immunogenicity by systemically replacing each of the donor CDRs with a human counterpart. The resultant panel of humanized antibodies is then scored for antigen affinity and potential immunogenicity of each CDR. In this way, the two clinically important properties of a candidate binding molecule, i.e., antigen binding and low immunogenicity, are determined. If patient sera against a corresponding murine or CDR-grafted (humanized) form of the antibody is available, then the entire panel of antibodies representing the systematic human CDR exchanges can be screened to determine the patients anti-idiotypic response against each donor CDR (for technical details, see, e.g., Iwashi et al., *Mol. Immunol.* 36:1079-91 (1999). Such an approach allows for identifying essential donor CDR regions from non-essential donor CDRs. Nonessential donor CDR regions may then be exchanged with a human counterpart CDR. Where an essential CDR region cannot be exchanged without unacceptable loss of function, identification of the specificity-determining residues (SDRs) of the CDR is performed by, for example, site-directed mutagenesis. In this way, the CDR can then be reengineered to retain only the SDRs and be human and/or minimally immunogenic at the remaining amino acid positions throughout the CDR. Such an approach, where only a portion of the donor CDR is grafted, is also referred to as abbreviated CDR-grafting (for technical details on the foregoing techniques, see, e.g., Tamura et al., *J. of Immunology* 164(3): 1432-41. (2000); Gonzales et al., *Mol. Immunol* 40:337-349 (2003); Kashmiri et al., *Crit. Rev. Oncol. Hematol.* 38:3-16 (2001); and De Pascalis et al., *J. of Immunology* 169(6):3076-84. (2002).

Moreover, it is sometimes possible to make one or more conservative amino acid substitutions of CDR residues without appreciably affecting the binding affinity of the resulting humanized immunoglobulin. By conservative substitutions are intended combinations such as gly, ala; val, ile, leu; asp, glu; asn, gln; ser, thr; lys, arg; and phe, tyr.

Additional candidates for substitution are acceptor human framework amino acids that are unusual or "rare" for a human immunoglobulin at that position. These amino acids can be substituted with amino acids from the equivalent position of the mouse donor antibody or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. Whether a residue is rare for acceptor human framework sequences should also be considered when selecting residues for backmutation based on contribution to CDR conformation. For example, if backmutation results in substitution of a residue that is rare for acceptor human framework sequences, a humanized antibody may be tested with and without for activity. If the backmutation is not necessary for activity, it may be eliminated to reduce immunogenicity concerns. For example, backmutation at the following residues may introduce a residue that is rare in acceptor human framework sequences; uk=v2 (2.0%), L3 (0.4%), T7 (1.8%), Q18 (0.2%), L83 (1.2%), I85 (2.9%), A100 (0.3%) and L106 (1.1%); and vh=T3 (2.0%), KS (1.8%), I11 (0.2%), S23 (1.5%), F24 (1.5%), S41 (2.3%), K71 (2.4%), R75 (1.4%), I82 (1.4%), D83 (2.2%) and L109 (0.8%). These criteria help ensure that an atypical amino acid in the human framework does not disrupt the antibody structure. Moreover, by replacing an unusual human acceptor amino acid with an amino acid from the donor antibody that happens to be typical for human antibodies, the humanized antibody may be made less immunogenic.

The term "rare", as used herein, indicates an amino acid occurring at that position in less than about 20%, preferably less than about 10%, more preferably less than about 5%, even more preferably less than about 3%, even more preferably less than about 2% and even more preferably less than about 1% of sequences in a representative sample of sequences, and the term "common", as used herein, indicates an amino acid occurring in more than about 25% but usually more than about 50% of sequences in a representative sample. For example, when deciding whether an amino acid in a human acceptor sequence is "rare" or "common", it will often be preferable to consider only human variable region sequences and when deciding whether a mouse amino acid is "rare" or "common", only mouse variable region sequences. Moreover, all human light and heavy chain variable region sequences are respectively grouped into "subgroups" of sequences that are especially homologous to each other and have the same amino acids at certain critical positions (Kabat et al., supra). When deciding whether an amino acid in a human acceptor sequence is "rare" or "common" among human sequences, it will often be preferable to consider only those human sequences in the same subgroup as the acceptor sequence.

Additional candidates for substitution are acceptor human framework amino acids that would be identified as part of a CDR region under the alternative definition proposed by Chothia et al., supra. Additional candidates for substitution are acceptor human framework amino acids that would be identified as part of a CDR region under the AbM and/or contact definitions.

Additional candidates for substitution are acceptor framework residues that correspond to a rare or unusual donor framework residue. Rare or unusual donor framework residues are those that are rare or unusual (as defined herein) for murine antibodies at that position. For murine antibodies, the subgroup can be determined according to Kabat and residue positions identified which differ from the consensus. These donor specific differences may point to somatic mutations in the murine sequence which enhance activity. Unusual residues that are predicted to affect binding (e.g., packing canonical and/or vernier residues) are retained, whereas residues predicted to be unimportant for binding can be substituted. Rare residues within the 12A11 UK sequence include I85 (3.6%). Rare residues within the 12A11 vh sequence include T3 (1.0%), I11 (1.7%), L12 (1.7%), S41 (2.8%), D83 (1.8%) and A85 (1.8%).

Additional candidates for substitution are non-germline residues occurring in an acceptor framework region. For example, when an acceptor antibody chain (i.e., a human antibody chain sharing significant sequence identity with the donor antibody chain) is aligned to a germline antibody chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. Thus, in one embodiment the variable framework region of the humanized immunoglobulin shares at least 85% sequence identity to a human variable framework region sequence or consensus of such sequences. In another embodiment, the variable framework region of the humanized immunoglobulin shares at least 90%, preferably 95%, more preferably 96%, 97%, 98% or 99% sequence identity to a human variable framework region sequence or consensus of such sequences. In general, however, such substitutions are undesirable.

In exemplary embodiments, the humanized antibodies of the invention exhibit a specific binding affinity for antigen of at least $10^7$, $10^8$, $10^9$ or $10^{10}$ M$^{-1}$. In other embodiments, the antibodies of the invention can have binding affinities of at least $10^{10}$, $10^{11}$ or $10^{12}$ M$^{-1}$. Usually the upper limit of binding affinity of the humanized antibodies for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized antibody having no substitutions (e.g., an antibody having donor CDRs and acceptor FRs, but no FR substitutions). In such instances, the binding of the optimized antibody (with substitutions) is preferably at least two- to three-fold greater, or three- to four-fold greater, than that of the unsubstituted antibody. For making comparisons, activity of the various antibodies can be determined, for example, by BIACORE™ (i.e., surface plasmon resonance using unlabelled reagents) or competitive binding assays.

c. Production of Humanized 12A11 Antibodies

A preferred embodiment of the present invention features a humanized antibody to the N-terminus of Aβ, in particular, for use in the therapeutic and/or diagnostic methodologies described herein. A particularly preferred starting material for production of humanized antibodies is the monoclonal antibody 12A11. 12A11 is specific for the N-terminus of Aβ and has been shown to (1) have a high avidity for aggregated Aβ1-42, (2) have the ability to capture soluble Aβ, and (3) mediate phagocytosis (e.g., induce phagocytosis) of amyloid plaque (see Example I). The in vivo efficacy of the 12A11 antibody is described in Example II. The cloning and sequencing of cDNA encoding the 12A11 antibody heavy and light chain variable regions is described in Example III.

Suitable human acceptor antibody sequences can be identified by computer comparisons of the amino acid sequences of the mouse variable regions with the sequences of known human antibodies. The comparison is performed separately for heavy and light chains but the principles are similar for each. In particular, variable domains from human antibodies whose framework sequences exhibit a high degree of sequence identity with the murine VL and VH framework regions are identified by query of, for example, the Kabat Database or the IgG Protein Sequence Database using NCBI IgG BLAST™ (publicly accessible through the National Institutes of Health NCBI internet server) with the respective murine framework sequences. In one embodiment, acceptor sequences sharing greater that 50% sequence identity with murine donor sequences, e.g., donor framework (FR) sequences, are selected. Preferably, acceptor antibody sequences sharing 60%, 65%, 70%, 75%, 80%, 85%, 90%, 95% sequence identity or more are selected.

A computer comparison of 12A11 revealed that the 12A11 light chain (mouse subgroup II) shows the greatest sequence identity to human light chains of subtype kappa II, and that the 12A11 heavy chain (mouse subgroup Ib) shows greatest sequence identity to human heavy chains of subtype II, as defined by Kabat et al., supra. Light and heavy human framework regions can be derived from human antibodies of these subtypes, or from consensus sequences of such subtypes. In a first humanization effort, light chain variable framework regions were derived from human subgroup II antibodies. Based on previous experiments designed to achieve high levels of expression of humanized antibodies having heavy chain variable framework regions derived from human subgroup II antibodies, it had been discovered that expression levels of such antibodies were sometimes low. Accordingly, based on the reasoning described in Saldanha et al. (1999) *Mol Immunol.* 36:709-19, framework regions from human subgroup III antibodies were chosen rather than human subgroup II.

A human subgroup II antibody K64(AIMS4) (accession no. BAC01733) was identified from the NCBI non-redundant database having significant sequence identity within the light chain variable regions of 12A11. A human subgroup III antibody M72 (accession no. AAA69734) was identified from the NCBI non-redundant database having significant sequence identity within the heavy chain variable regions of 12A11 (see also Schroeder and Wang (1990) *Proc. Natl. Acad. Sci. U.S.A.* 872: 6146-6150.

Alternative light chain acceptor sequences include, for example, PDB Accession No. IKFA (gi24158782), PDB Accession No. IKFA (gi24158784), EMBL Accession No. CAE75574.1 (gi38522587), EMBL Accession No. CAE75575.1 (gi38522590), EMBL Accession No. CAE84952.1 (gi39838891), DJB Accession No. BAC01734.1 (gi21669419), DJB Accession No. BAC01730.1 (gi21669411), PIR Accession No. 540312 (gi481978), EMBL Accession No. CAA51090.1 (gi3980118), Accession No. AAH63599.1 (gi39794308), PIR Accession No. S22902 (gi106540), PIR Accession No. 542611 (gi631215), EMBL Accession No. CAA38072.1 (gi433890), EMBL Accession No. CAA39072.1 (gi34000), PIR Accession No. S23230 (gi284256), DBJ Accession No. BAC01599.1 (gi21669149), DBJ Accession No. BAC01729.1 (gi21669409), DBJ Accession No. BAC01562.1 (gi21669075), EMBL Accession No. CAA85590.1 (gi587338), Accession No. AAQ99243.1 (gi37694665), GENBANK® Accession No. AAK94811.1 (gi18025604), EMBL Accession No. CAB51297.1 (gi5578794), DBJ Accession No. BAC01740.1 (gi21669431), GENBANK® Accession No. AAB35009.1 (gi1041885) and DBJ Accession No. BAC01733.1 (gi21669417). Alternative heavy chain acceptor sequences include, for example, DBJ Accession No. BAC01904.1 (gi21669789), GENBANK® Accession No. AAD53816.1 (gi5834100), GENBANK® Accession No. AAS86081.1 (gi46254223), DBJ Accession No. BAC01462.1 (gi21668870), GENBANK® Accession No. AAC18191.1 (gi3170773), DBJ Accession No. BAC02266.1 (gi21670513), GENBANK® Accession No. AAD56254.1 (gi5921589), GENBANK Accession No. AAD53807.1 (gi5834082), DBJ Accession No. BAC02260.1 (gi21670501), GENBANK Accession No. AAC18166.1 (gi3170723), EMBL Accession No. CAA49495.1 (gi33085), PIR Accession No. 531513 (gi345903), GENBANK® Accession No. AAS86079.1 (gi46254219), DBJ Accession No. BAC01917.1 (gi21669815), DBJ Accession No. BAC01912.1 (gi21669805), GENBANK Accession No. AAC18283.1 (gi3170961), DBJ Accession No. BAC01903 (gi21669787), DBJ Accession NO. BAC01887.1 (gi21669755), DBJ Accession No. BAC02259.1 (gi21670499), DBJ Accession No. BACOI913.1 (gi21669807), DBJ Accession No. BACOI910.1 (gi21669801), DJB Accession No. BAC02267.1 (gi21670515), GENBANK Accession No. AAC18306.1 (gi3171011), GENBANK Accession No. AAD53817.1 (gi5834102), PIR Accession No. E36005 (gi106423), EMBL CAB37129.1 (gi4456494), GENBANK® Accession No. AAD00856.1 (gi4100384), and GENBANK® AAA68892.1 (gi186190).

In exemplary embodiments, humanized antibodies of the invention include 12A11 CDRs and FRs from an acceptor sequence listed supra. Residues within the framework regions important for CDR conformation and/or activity as described herein are selected for backmutation (if differing between donor and acceptor sequences).

Residues are next selected for substitution, as follows. When an amino acid differs between a 12A11 variable framework region and an equivalent human variable framework region, the human framework amino acid should usually be substituted by the equivalent mouse amino acid if it is reasonably expected that the amino acid:

(1) noncovalently binds antigen directly, (2) is adjacent to a CDR region, is part of a CDR region under the alternative definition proposed by Chothia et al., supra, or otherwise interacts with a CDR region (e.g., is within about 3A of a CDR region), or (3) participates in the VL-VH interface.

Structural analysis of the 12A11 antibody heavy and light chain variable regions, and humanization of the 12A11 antibody is described in Example V. Briefly, three-dimensional models for the solved murine antibody structures 1 KTR for the light chain and 1JRH and 1ETZ for the heavy chain were studied. Alternative three-dimensional models which can be studied for identification of residues, important for CDR confirmation (e.g., vernier residues), include PDB Accession No. 2JEL (gi3212688), PDB Accession No. 1TET (gi494639), PDB Accession No. IJP5 (gi16975307), PDB Accession No. 1CBV (gi493917), PDB Accession No. 2PCP (gi4388943), PDB Accession No. 1191 (gi2050118), PDB Accession No. 1CLZ (gi1827926), PDB Accession No. 1FL6 (gi17942615) and PDB Accession No. 1KEL (gi 1942968) for the light chain and PDB 1GGI (gi442938), PDB Accession No. 1GGB (gi442934), PDB Accession No. 1N5Y (gi28373913), PDB Accession No. 2HMI (gi3891821), PDB Accession No. 1FDL (gi229915), PDB Accession No. 1KIP (gi1942788), PDB Accession No. 1KIQ (gi1942791) and PDB Accession No. 1VFA (gi576325) for the heavy chain.

Three-dimensional structural information for the antibodies described herein is publicly available, for example, from the Research Collaboratory for Structural Bioinformatics' Protein Data Bank (PDB). The PDB is freely accessible via the World Wide Web internet and is described by Berman et al. (2000) *Nucleic Acids Research,* 28:235. Study of solved three-dimensional structures allows for the identification of CDR-interacting residues within 12A11. Alternatively, three-dimensional models for the 12A11 VH and VL chains can be generated using computer modeling software. Briefly, a three-dimensional model is generated based on the closest solved murine antibody structures for the heavy and light chains. For this purpose, 1KTR can be used as a template for modeling the 12A11 light chain, and 1ETZ and 1JRH used as templates for modeling the heavy chain. The model can be further refined by a series of energy minimization steps to relieve unfavorable atomic contacts and optimize electrostatic and van der Waals interactions. Additional three-dimensional analysis and/or modeling can be performed using 2JEL (2.5 Å) and/or 1TET (2.3 Å) for the light chain and 1GGI (2.8 Å) for the heavy chain (or other antibodies set forth supra) based on the similarity between these solved murine structures and the respective 12A11 chains.

The computer model of the structure of 12A11 can further serve as a starting point for predicting the three-dimensional structure of an antibody containing the 12A11 complementarity determining regions substituted in human framework structures. Additional models can be constructed representing the structure as further amino acid substitutions are introduced.

In general, substitution of one, most or all of the amino acids fulfilling the above criteria is desirable. Accordingly, the humanized antibodies of the present invention will usually contain a substitution of a human light chain framework residue with a corresponding 12A11 residue in at least 1, 2, 3 or more of the chosen positions. The humanized antibodies also usually contain a substitution of a human heavy chain framework residue with a corresponding 12A11 residue in at least 1, 2, 3 or more of the chosen positions.

Occasionally, however, there is some ambiguity about whether a particular amino acid meets the above criteria, and alternative variant immunoglobulins are produced, one of which has that particular substitution, the other of which does not. In instances where substitution with a murine residue would introduce a residue that is rare in human immunoglobulins at a particular position, it may be desirable to test the antibody for activity with or without the particular substitution. If activity (e.g., binding affinity and/or binding specificity) is about the same with or without the substitution, the antibody without substitution may be preferred, as it would be expected to elicit less of a HAMA response, as described herein.

Other candidates for substitution are acceptor human framework amino acids that are unusual for a human immunoglobulin at that position. These amino acids can be substituted with amino acids from the equivalent position of more typical human immunoglobulins. Alternatively, amino acids from equivalent positions in the mouse 12A11 can be introduced into the human framework regions when such amino acids are typical of human immunoglobulin at the equivalent positions.

Other candidates for substitution are non-germline residues occurring in a framework region. By performing a computer comparison of 12A11 with known germline sequences, germline sequences with the greatest degree of sequence identity to the heavy or light chain can be identified. Alignment of the framework region and the germline sequence will reveal which residues may be selected for substitution with corresponding germline residues. Residues not matching between a selected light chain acceptor framework and one of these germline sequences could be selected for substitution with the corresponding germline residue.

Rare mouse residues are identified by comparing the donor VL and/or VH sequences with the sequences of other members of the subgroup to which the donor VL and/or VH sequences belong (according to Kabat) and identifying the residue positions which differ from the consensus. These donor specific differences may point to somatic mutations which enhance activity. Unusual or rare residues close to the binding site may possibly contact the antigen, making it desirable to retain the mouse residue. However, if the unusual mouse residue is not important for binding, use of the corresponding acceptor residue is preferred as the mouse residue may create immunogenic neoepitopes in the humanized antibody. In the situation where an unusual residue in the donor sequence is actually a common residue in the corresponding acceptor sequence, the preferred residue is clearly the acceptor residue.

Table 1A summarizes the sequence analysis of the 12A11 VH and VL regions.

TABLE 1

Summary of 12A11 V region sequence

| Chain | VL | VH |
|---|---|---|
| Mouse Subgroup | II | Ib |
| Human Subgroup | II | II |
| Rare amino acids in mouse vk (% frequency) | I85 (3.6%) | I11 (1.7%) |
| Chothia canonical class | L1: class 4[16f] | H1: class 3 [7] |
|  | L2: class 1[7] | H2: class 1[16] |
|  | L3: class 1[9] | H3[1] |
| Closest mouse MAb solved structure | 1KTR[2] | 1ETZ[3] (2.6 Å) and 1JRH[4] |
| Homology with Modeling template | 94% | 83% and 86% |
| Human Framework seq | K64 (BAC01733) (87% FR, 67% overall) | M72 (AAA69734) (61% FR, 45% overall) |
| Donornotes | Hu k LC subgroup II CDRs from same canonical Structural group as 12A11 | HU HC subgroup III CDRs from same canonical structural group as 12A11 |
| Backmutation Notes | none | A24F, F29L: H1 R71K: Canonical, H2 V37I: Packing T28S, V48L, F67L, N73T, L78V: Vernier |
| Germline ref for Hu Fr | A19 VL Vk2-28 mRNA: X63397.1 (GI: 33774) | AAA69731.1 (GI: 567123) |

[1]No canonical class but might form a kinked base according to the rules of Shirai et al. (1999) *FEBS Lett.* 4 55: 188-197.
[2]Kaufmann et al. (2002) *J Mol Biol.* 318: 135-147.
[3]Guddat et al. (2000) *J Mol Biol.* 302: 853-872.
[4]Sogabe et al. (1997) *J Mol Biol.* 273: 882-897.

Germline sequences are set forth that can be used in selecting amino acid substitutions.

Three-dimensional structural information for antibodies described herein is publicly available, for example, from the Research Collaboratory for Structural Bioinformatics' Protein Data Bank (PDB). The PDB is freely accessible via the World Wide Web internet and is described by Berman et al. (2000) *Nucleic Acids Research*, p 235-242. Germline gene sequences referenced herein are publicly available, for example, from the National Center for Biotechnology Information (NCBI) database of sequences in collections of Igh, Ig kappa and Ig lambda germline V genes (as a division of the National Library of Medicine (NLM) at the National Institutes of Health (NIH)). Homology searching of the NCBI "Ig Germline Genes" database is provided by IgG BLAST™.

In an exemplary embodiment, a humanized antibody of the present invention contains (i) a light chain comprising a variable domain comprising murine 12A11 VL CDRs and a human acceptor framework, the framework having zero, one, two, three, four, five, six, seven, eight, nine or more residues substituted with the corresponding 12A11 residue and (ii) a heavy chain comprising 12A11 VH CDRs and a human acceptor framework, the framework having at least one, two, three, four, five, six, seven, eight, nine or more residues substituted with the corresponding 12A11 residue, and, optionally, at least one, preferably two or three residues substituted with a corresponding human germline residue.

In another exemplary embodiment, a humanized antibody of the present invention contains (i) a light chain comprising a variable domain comprising murine 12A11 VL CDRs and a human acceptor framework, the framework having at least one, two, three, four, five, six, seven, eight, nine or more residues backmutated (i.e., substituted with the corresponding 12A11 residue), wherein the backmutation(s) are at a canonical, packing and/or vernier residues and (ii) a heavy chain comprising 12A11 VH CDRs and a human acceptor framework, the framework having at least one, two, three, four, five, six, seven, eight, nine or more residues backmutated, wherein the backmutation(s) are at a canonical, packing and/or vernier residues. In certain embodiments, backmutations are only at packing and/or canonical residues or are primarily at canonical and/or packing residues (e.g., only 1 or 2 vernier residues of the vernier residues differing between the donor and acceptor sequence are backmutated).

In other embodiments, humanized antibodies include the fewest number of backmutations possible while retaining a binding affinity comparable to that of the donor antibody (or a chimeric version thereof). To arrive at such versions, various combinations of backmutations can be eliminated and the resulting antibodies tested for efficacy (e.g., binding affinity). For example, backmutations (e.g., 1, 2, 3, or 4 backmutations) at vernier residues can be eliminated or backmutations at combinations of vernier and packing, vernier and canonical or packing and canonical residues can be eliminated.

In another embodiment, a humanized antibody of the present invention has structural features, as described herein, and further has at least one (preferably two, three, four or all) of the following activities: (1) binds soluble Aβ; (2) binds aggregated Aβ1-42 (e.g., as determined by ELISA); (3) captures soluble Aβ; (4) binds Aβ in plaques (e.g., staining of AD and/or PDAPP plaques); (5) binds Aβ with an affinity no less than two to three fold lower than chimeric 12A11 (e.g., 12A11 having murine variable region sequences and human constant region sequences); (6) mediates phagocytosis of Aβ (e.g., in an ex vivo phagocytosis assay, as described herein); and (7) crosses the blood-brain barrier (e.g., demonstrates short-term brain localization, for example, in a PDAPP animal model, as described herein).

In another embodiment, a humanized antibody of the present invention has structural features, as described herein, such that it binds Aβ in a manner or with an affinity sufficient to elicit at least one of the following in vivo effects: (1) reduce Aβ plaque burden; (2) prevent plaque formation; (3) reduce levels of soluble Aβ; (4) reduce the neuritic pathology associated with an amyloidogenic disorder; (5) lessen or ameliorate at least one physiological symptom associated with an amyloidogenic disorder; and/or (6) improve cognitive function.

In another embodiment, a humanized antibody of the present invention has structural features, as described herein, and specifically binds to an epitope comprising residues 3-7 of Aβ.

In yet another embodiment, a humanized antibody of the present invention has structural features, as described herein, such that it binds to an N-terminal epitope within Aβ (e.g., binds to an epitope within amino acids 3-7 of Aβ), and is capable of reducing (1) Aβ peptide levels; (2) Aβ plaque burden; and (3) the neuritic burden or neuritic dystrophy associated with an amyloidogenic disorder.

The activities described above can be determined utilizing any one of a variety of assays described herein or in the art (e.g., binding assays, phagocytosis assays, etc.). Activities can be assayed either in vivo (e.g., using labeled assay components and/or imaging techniques) or in vitro (e.g., using samples or specimens derived from a subject). Activities can be assayed either directly or indirectly. In certain preferred embodiments, neurological endpoints (e.g., amyloid burden, neuritic burden, etc) are assayed. Such endpoints can be assayed in living subjects (e.g., in animal models of Alzheimer's disease or in human subjects, for example, undergoing immunotherapy) using non-invasive detection methodologies. Alternatively, such endpoints can be assayed in subjects post mortem. Assaying such endpoints in animal models and/or in human subjects post mortem is useful in assessing the effectiveness of various agents (e.g., humanized antibodies) to be utilized in similar immunotherapeutic applications. In other preferred embodiments, behavioral or neurological parameters can be assessed as indicators of the above neuropathological activities or endpoints.

3. Production of Variable Regions

Having conceptually selected the CDR and framework components of humanized immunoglobulins, a variety of methods are available for producing such immunoglobulins. In general, one or more of the murine complementarity determining regions (CDR) of the heavy and/or light chain of the antibody can be humanized, for example, placed in the context of one or more human framework regions, using primer-based polymerase chain reaction (PCR). Briefly, primers are designed which are capable of annealing to target murine CDR region(s) which also contain sequence which overlaps and can anneal with a human framework region. Accordingly, under appropriate conditions, the primers can amplify a murine CDR from a murine antibody template nucleic acid and add to the amplified template a portion of a human framework sequence. Similarly, primers can be designed which are capable of annealing to a target human framework region(s) where a PCR reaction using these primers results in an amplified human framework region(s). When each amplification product is then denatured, combined, and annealed to the other product, the murine CDR region, having overlapping human framework sequence with the amplified human framework sequence, can be genetically linked. Accordingly, in one or more such reactions, one or more murine CDR regions can be genetically linked to intervening human framework regions.

In some embodiments, the primers may also comprise desirable restriction enzyme recognition sequences to facilitate the genetic engineering of the resultant PCR amplified sequences into a larger genetic segment, for example, a variable light or heavy chain segment, heavy chain, or vector. In addition, the primers used to amplify either the murine CDR regions or human framework regions may have desirable mismatches such that a different codon is introduced into the murine CDR or human framework region. Typical mismatches introduce alterations in the human framework regions that preserve or improve the structural orientation of the murine CDR and thus its binding affinity, as described herein.

It should be understood that the foregoing approach can be used to introduce one, two, or all three murine CDR regions into the context of intervening human framework regions. Methods for amplifying and linking different sequences using primer-based PCR are described in, for example, Sambrook, Fritsch and Maniatis, *Molecular Cloning: Cold Spring Harbor Laboratory Press* (1989); *DNA Cloning*, Vols. 1 and 2, (D. N. Glover, Ed. 1985); *PCR Handbook Current Protocols in Nucleic Acid Chemistry*, Beaucage, Ed. John Wiley & Sons (1999) (Editor); *Current Protocols in Molecular Biology*, eds. Ausubel et al., John Wiley & Sons (1992).

Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. Oligonucleotide-mediated mutagenesis is a preferred method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

4. Selection of Constant Regions

The variable segments of antibodies produced as described supra (e.g., the heavy and light chain variable regions of chimeric or humanized antibodies) are typically linked to at least a portion of an immunoglobulin constant region (Fc region), typically that of a human immunoglobulin. Human constant region DNA sequences can be isolated in accordance with well known procedures from a variety of human cells, but preferably immortalized B cells (see Kabat et al., supra, and Liu et al., WO87/02671) (each of which is incorporated by reference in its entirety for all purposes). Ordinarily, the antibody will contain both light chain and heavy chain constant regions. The heavy chain constant region usually includes CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. When it is desired that the antibody (e.g., humanized antibody) exhibit cytotoxic activity, the constant domain is usually a complement fixing constant domain and the class is typically IgG1. Human isotype IgG1 is preferred. Light chain constant regions can be lambda or kappa. The humanized antibody may comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

5. Expression of Recombinant Antibodies

Chimeric and humanized antibodies are typically produced by recombinant expression. Nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells (e.g., COS cells). Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., Itakura et al., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, preferably, myeloma cell lines, or transformed B-cells or hybridomas. Preferably, the cells are nonhuman. Expression vectors for these cells can include expression control sequences, such as an origin of replication, a promoter, and an enhancer (Queen et al., *Immunol. Rev.* 89:49

(1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149 (1992).

Alternatively, antibody-coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

Alternatively, antibodies (e.g., humanized antibodies) of the invention can be produced in transgenic plants (e.g., tobacco, maize, soybean and alfalfa). Improved 'plantibody' vectors (Hendy et al. (1999) *J. Immunol. Methods* 231:137-146) and purification strategies coupled with an increase in transformable crop species render such methods a practical and efficient means of producing recombinant immunoglobulins not only for human and animal therapy, but for industrial applications as well (e.g., catalytic antibodies). Moreover, plant produced antibodies have been shown to be safe and effective and avoid the use of animal-derived materials and therefore the risk of contamination with a transmissible spongiform encephalopathy (TSE) agent. Further, the differences in glycosylation patterns of plant and mammalian cell-produced antibodies have little or no effect on antigen binding or specificity. In addition, no evidence of toxicity or HAMA has been observed in patients receiving topical oral application of a plant-derived secretory dimeric IgA antibody (see Larrick et al. (1998) *Res. Immunol.* 149:603-608).

Various methods may be used to express recombinant antibodies in transgenic plants. For example, antibody heavy and light chains can be independently cloned into expression vectors (e.g., *Agrobacterium tumefaciens* vectors), followed by the transformation of plant tissue in vitro with the recombinant bacterium or direct transformation using, e.g., particles coated with the vector which are then physically introduced into the plant tissue using, e.g., ballistics. Subsequently, whole plants expressing individual chains are reconstituted followed by their sexual cross, ultimately resulting in the production of a fully assembled and functional antibody. Similar protocols have been used to express functional antibodies in tobacco plants (see Hiatt et al. (1989) *Nature* 342:76-87). In various embodiments, signal sequences may be utilized to promote the expression, binding and folding of unassembled antibody chains by directing the chains to the appropriate plant environment (e.g., the aqueous environment of the apoplasm or other specific plant tissues including tubers, fruit or seed) (see Fiedler et al. (1995) *Bio/Technology* 13:1090-1093). Plant bioreactors can also be used to increase antibody yield and to significantly reduce costs.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989) (incorporated by reference in its entirety for all purposes). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

6. Antibody Fragments

Also contemplated within the scope of the instant invention are antibody fragments. In one embodiment, fragments of non-human, and/or chimeric antibodies are provided. In another embodiment, fragments of humanized antibodies are provided. Typically, these fragments exhibit specific binding to antigen with an affinity of at least $10^7$, and more typically $10^8$ or $10^9$ $M^{-1}$. Humanized antibody fragments include separate heavy chains, light chains, Fab, Fab', F(ab')2, Fabc, and Fv. Fragments are produced by recombinant DNA techniques, or by enzymatic or chemical separation of intact immunoglobulins.

7. Epitope Mapping

Epitope mapping can be performed to determine which antigenic determinant or epitope of Aβ is recognized by the antibody. In one embodiment, epitope mapping is performed according to Replacement NET (rNET) analysis. The rNET epitope map assay provides information about the contribution of individual residues within the epitope to the overall binding activity of the antibody. rNET analysis uses synthesized systematic single substituted peptide analogs. Binding of an antibody being tested is determined against native peptide (native antigen) and against 19 alternative "single substituted" peptides, each peptide being substituted at a first position with one of 19 non-native amino acids for that position. A profile is generated reflecting the effect of substitution at that position with the various non-native residues. Profiles are likewise generated at successive positions along the antigenic peptide. The combined profile, or epitope map, (reflecting substitution at each position with all 19 non-native residues) can then be compared to a map similarly generated for a second antibody. Substantially similar or identical maps indicate that antibodies being compared have the same or similar epitope specificity.

8. Testing Antibodies for Therapeutic Efficacy in Animal Models

Groups of 7-9 month old PDAPP mice each are injected with 0.5 mg in PBS of polyclonal anti-Aβ or specific anti-Aβ monoclonal antibodies. All antibody preparations are purified to have low endotoxin levels. Monoclonals can be prepared against a fragment by injecting the fragment or longer form of Aβ into a mouse, preparing hybridomas and screening the hybridomas for an antibody that specifically binds to a desired fragment of Aβ without binding to other nonoverlapping fragments of Aβ.

Mice are injected intraperitoneally as needed over a 4 month period to maintain a circulating antibody concentration measured by ELISA titer of greater than 1/1000 defined by ELISA to Aβ42 or other immunogen. Titers are monitored and mice are euthanized at the end of 6 months of injections. Histochemistry, Aβ levels and toxicology are performed post mortem. Ten mice are used per group.

9. Screening Antibodies for Clearing Activity

The invention also provides methods of screening an antibody for activity in clearing an amyloid deposit or any other antigen, or associated biological entity, for which clearing activity is desired. To screen for activity against an amyloid deposit, a tissue sample from a brain of a patient with Alzheimer's disease or an animal model having characteristic Alzheimer's pathology is contacted with phagocytic cells bearing an Fc receptor, such as microglial cells, and the antibody under test in a medium in vitro. The phagocytic cells can be a primary culture or a cell line, and can be of murine (e.g., BV-2 or C8-B4 cells) or human origin (e.g., THP-1 cells). In some methods, the components are combined on a microscope slide to facilitate microscopic monitoring. In some methods, multiple reactions are performed in parallel in the wells of a microtiter dish. In such a format, a separate miniature microscope slide can be mounted in the separate wells, or a nonmicroscopic detection format, such as ELISA detection of Aβ can be used. Preferably, a series of measurements is made of the amount of amyloid deposit in the in vitro reaction mixture, starting from a baseline value before the reaction has proceeded, and one or more test values during the reaction. The antigen can be detected by staining, for example, with a fluorescently labeled antibody to Aβ or other component of amyloid plaques. The antibody used for staining may or may not be the same as the antibody being tested for clearing activity. A reduction relative to baseline during the reaction of the amyloid deposits indicates that the antibody under test has clearing activity. Such antibodies are likely to be useful in preventing or treating Alzheimer's and other amyloidogenic diseases. Particularly useful antibodies for preventing or treating Alzheimer's and other amyloidogenic diseases include those capable of clearing both compact and diffuse amyloid plaques, for example, the 12A11 antibody of the instant invention, or chimeric or humanized versions thereof.

Analogous methods can be used to screen antibodies for activity in clearing other types of biological entities. The assay can be used to detect clearing activity against virtually any kind of biological entity. Typically, the biological entity has some role in human or animal disease. The biological entity can be provided as a tissue sample or in isolated form. If provided as a tissue sample, the tissue sample is preferably unfixed to allow ready access to components of the tissue sample and to avoid perturbing the conformation of the components incidental to fixing. Examples of tissue samples that can be tested in this assay include cancerous tissue, precancerous tissue, tissue containing benign growths such as warts or moles, tissue infected with pathogenic microorganisms, tissue infiltrated with inflammatory cells, tissue bearing pathological matrices between cells (e.g., fibrinous pericarditis), tissue bearing aberrant antigens, and scar tissue. Examples of isolated biological entities that can be used include Aβ, viral antigens or viruses, proteoglycans, antigens of other pathogenic microorganisms, tumor antigens, and adhesion molecules. Such antigens can be obtained from natural sources, recombinant expression or chemical synthesis, among other means. The tissue sample or isolated biological entity is contacted with phagocytic cells bearing Fc receptors, such as monocytes or microglial cells, and an antibody to be tested in a medium. The antibody can be directed to the biological entity under test or to an antigen associated with the entity. In the latter situation, the object is to test whether the biological entity is phagocytosed with the antigen. Usually, although not necessarily, the antibody and biological entity (sometimes with an associated antigen), are contacted with each other before adding the phagocytic cells. The concentration of the biological entity and/or the associated antigen remaining in the medium, if present, is then monitored. A reduction in the amount or concentration of antigen or the associated biological entity in the medium indicates the antibody has a clearing response against the antigen and/or associated biological entity in conjunction with the phagocytic cells.

10. Chimeric/Humanized Antibodies Having Altered Effector Function

For the above-described antibodies of the invention comprising a constant region (Fc region), it may also be desirable to alter the effector function of the molecule. Generally, the effector function of an antibody resides in the constant or Fc region of the molecule which can mediate binding to various effector molecules, e.g., complement proteins or Fc receptors. The binding of complement to the Fc region is important, for example, in the opsonization and lysis of cell pathogens and the activation of inflammatory responses. The binding of antibody to Fc receptors, for example, on the surface of effector cells can trigger a number of important and diverse biological responses including, for example, engulfment and destruction of antibody-coated pathogens or particles, clearance of immune complexes, lysis of antibody-coated target cells by killer cells (i.e., antibody-dependent cell-mediated cytotoxicity, or ADCC), release of inflammatory mediators, placental transfer of antibodies, and control of immunoglobulin production.

Accordingly, depending on a particular therapeutic or diagnostic application, the above-mentioned immune functions, or only selected immune functions, may be desirable. By altering the Fc region of the antibody, various aspects of the effector function of the molecule, including enhancing or suppressing various reactions of the immune system, with beneficial effects in diagnosis and therapy, are achieved.

The antibodies of the invention can be produced which react only with certain types of Fc receptors, for example, the antibodies of the invention can be modified to bind to only certain Fc receptors, or if desired, lack Fc receptor binding entirely, by deletion or alteration of the Fc receptor binding site located in the Fc region of the antibody. Other desirable alterations of the Fc region of an antibody of the invention are cataloged below. Typically the Kabat numbering system is used to indicate which amino acid residue(s) of the Fc region (e.g., of an IgG antibody) are altered (e.g., by amino acid substitution) in order to achieve a desired change in effector function. The numbering system is also employed to compare antibodies across species such that a desired effector function observed in, for example, a mouse antibody, can then be systematically engineered into a human, humanized, or chimeric antibody of the invention.

For example, it has been observed that antibodies (e.g., IgG antibodies) can be grouped into those found to exhibit tight, intermediate, or weak binding to an Fc receptor (e.g., an Fc receptor on human monocytes (FcγRI)). By comparison of the amino-acid sequences in these different affinity groups, a monocyte-binding site in the hinge-link region (Leu234-Ser239) has been identified. Moreover, the human FcγRI receptor binds human IgG1 and mouse IgG2a as a monomer, but the binding of mouse IgG2b is 100-fold weaker. A comparison of the sequence of these proteins in the hinge-link region shows that the sequence 234 to 238, i.e., Leu-Leu-Gly- Gly-Pro (SEQ ID NO:32) in the strong binders becomes Leu-Glu-Gly-Gly-Pro (SEQ ID NO:33) in mouse gamma 2b, i.e., weak binders. Accordingly, a corresponding change in a human antibody hinge sequence can be made if reduced FcγI receptor binding is desired. It is understood that other alterations can be made to achieve the same or similar results. For example, the affinity of FcγRI binding can be altered by replacing the specified residue with a residue having an inappropriate functional group on its sidechain, or by introducing a charged functional group (e.g., Glu or Asp) or for example an aromatic non-polar residue (e.g., Phe, Tyr, or Trp).

These changes can be equally applied to the murine, human, and rat systems given the sequence homology between the different immunoglobulins. It has been shown that for human IgG3, which binds to the human FcγRI receptor, changing Leu 235 to Glu destroys the interaction of the mutant for the receptor. The binding site for this receptor can thus be switched on or switched off by making the appropriate mutation.

Mutations on adjacent or close sites in the hinge link region (e.g., replacing residues 234, 236 or 237 by Ala) indicate that alterations in residues 234, 235, 236, and 237 at least affect affinity for the FcγRI receptor. Accordingly, the antibodies of the invention can also have an altered Fc region with altered binding affinity for FcγRI as compared with the unmodified antibody. Such an antibody conveniently has a modification at amino acid residue 234, 235, 236, or 237.

Affinity for other Fc receptors can be altered by a similar approach, for controlling the immune response in different ways.

As a further example, the lytic properties of IgG antibodies following binding of the C1 component of complement can be altered.

The first component of the complement system, C1, comprises three proteins known as C1q, C1r and C1s which bind tightly together. It has been shown that C1q is responsible for binding of the three protein complex to an antibody.

Accordingly, the C1q binding activity of an antibody can be altered by providing an antibody with an altered CH 2 domain in which at least one of the amino acid residues 318, 320, and 322 of the heavy chain has been changed to a residue having a different side chain. The numbering of the residues in the heavy chain is that of the EU index (see Kabat et al., supra). Other suitable alterations for altering, e.g., reducing or abolishing specific C1q-binding to an antibody include changing any one of residues 318 (Glu), 320 (Lys) and 322 (Lys), to Ala.

Moreover, by making mutations at these residues, it has been shown that C1q binding is retained as long as residue 318 has a hydrogen-bonding side chain and residues 320 and 322 both have a positively charged side chain.

C1q binding activity can be abolished by replacing any one of the three specified residues with a residue having an inappropriate functionality on its side chain. It is not necessary to replace the ionic residues only with Ala to abolish C1q binding. It is also possible to use other alkyl-substituted non-ionic residues, such as Gly, Ile, Leu, or Val, or such aromatic non-polar residues as Phe, Tyr, Trp and Pro in place of any one of the three residues in order to abolish C1q binding. In addition, it is also be possible to use such polar non-ionic residues as Ser, Thr, Cys, and Met in place of residues 320 and 322, but not 318, in order to abolish C1q binding activity.

It is also noted that the side chains on ionic or non-ionic polar residues will be able to form hydrogen bonds in a similar manner to the bonds formed by the Glu residue. Therefore, replacement of the 318 (Glu) residue by a polar residue may modify but not abolish C1q binding activity.

It is also known that replacing residue 297 (Asn) with Ala results in removal of lytic activity while only slightly reducing (about three fold weaker) affinity for C1q. This alteration destroys the glycosylation site and the presence of carbohydrate that is required for complement activation. Any other substitution at this site will also destroy the glycosylation site.

The invention also provides an antibody having an altered effector function wherein the antibody has a modified hinge region. The modified hinge region may comprise a complete hinge region derived from an antibody of different antibody class or subclass from that of the CH1 domain. For example, the constant domain (CH1) of a class IgG antibody can be attached to a hinge region of a class IgG4 antibody. Alternatively, the new hinge region may comprise part of a natural hinge or a repeating unit in which each unit in the repeat is derived from a natural hinge region. In one example, the natural hinge region is altered by converting one or more cysteine residues into a neutral residue, such as alanine, or by converting suitably placed residues into cysteine residues. Such alterations are carried out using art recognized protein chemistry and, preferably, genetic engineering techniques, as described herein.

In one embodiment of the invention, the number of cysteine residues in the hinge region of the antibody is reduced, for example, to one cysteine residue. This modification has the advantage of facilitating the assembly of the antibody, for example, bispecific antibody molecules and antibody molecules wherein the Fc portion has been replaced by an effector or reporter molecule, since it is only necessary to form a single disulfide bond. This modification also provides a specific target for attaching the hinge region either to another hinge region or to an effector or reporter molecule, either directly or indirectly, for example, by chemical means.

Conversely, the number of cysteine residues in the hinge region of the antibody is increased, for example, at least one more than the number of normally occurring cysteine residues. Increasing the number of cysteine residues can be used to stabilize the interactions between adjacent hinges. Another advantage of this modification is that it facilitates the use of cysteine thiol groups for attaching effector or reporter molecules to the altered antibody, for example, a radiolabel.

Accordingly, the invention provides for an exchange of hinge regions between antibody classes, in particular, IgG classes, and/or an increase or decrease in the number of cysteine residues in the hinge region in order to achieve an altered effector function (see for example U.S. Pat. No. 5,677, 425 which is expressly incorporated herein). A determination of altered antibody effector function is made using the assays described herein or other art recognized techniques.

Importantly, the resultant antibody can be subjected to one or more assays to evaluate any change in biological activity compared to the starting antibody. For example, the ability of the antibody with an altered Fc region to bind complement or Fc receptors can be assessed using the assays disclosed herein as well as any art recognized assay.

Production of the antibodies of the invention is carried out by any suitable technique including techniques described herein as well as techniques known to those skilled in the art. For example an appropriate protein sequence, e.g. forming part of or all of a relevant constant domain, e.g., Fc region, i.e., CH2, and/or CH3 domain(s), of an antibody, and include appropriately altered residue(s) can be synthesized and then chemically joined into the appropriate place in an antibody molecule.

Preferably, genetic engineering techniques are used for producing an altered antibody. Preferred techniques include, for example, preparing suitable primers for use in polymerase chain reaction (PCR) such that a DNA sequence which encodes at least part of an IgG heavy chain, e.g., an Fc or constant region (e.g., CH2, and/or CH3) is altered, at one or more residues. The segment can then be operably linked to the remaining portion of the antibody, e.g., the variable region of the antibody and required regulatory elements for expression in a cell.

The present invention also includes vectors used to transform the cell line, vectors used in producing the transforming vectors, cell lines transformed with the transforming vectors, cell lines transformed with preparative vectors, and methods for their production.

Preferably, the cell line which is transformed to produce the antibody with an altered Fc region (i.e., of altered effector function) is an immortalized mammalian cell line (e.g., CHO cell).

Although the cell line used to produce the antibody with an altered Fc region is preferably a mammalian cell line, any other suitable cell line, such as a bacterial cell line or a yeast cell line, may alternatively be used.

11. Affinity Maturation

Antibodies (e.g., humanized antibodies) of the invention can be modified for improved function using any of a number of affinity maturation techniques. Typically, a candidate molecule with a binding affinity to a given target molecule is identified and then further improved or "matured" using mutagenesis techniques resulting in one or more related candidates having a more desired binding interaction with the target molecule. Typically, it is the affinity of the antibody (or avidity, i.e., the combined affinities of the antibody for a target antigen) that is modified, however, other properties of the molecule, such as stability, effector function, clearance, secretion, or transport function, may also be modified, either separately or in parallel with affinity, using affinity maturation techniques.

In exemplary embodiments, the affinity of an antibody (e.g., a humanized antibody of the instant invention) is increased. For example, antibodies having binding affinities of at least $10^7 M^{-1}$, $10^8 M^{-1}$ or $10^9 M^{-1}$ can be matured such that their affinities are at least $10^9 M^{-1}$, $10^{10} M^{-1}$ or $10^{12} M^{-1}$.

One approach for affinity maturing a binding molecule is to synthesize a nucleic acid encoding the binding molecule, or portion thereof, that encodes the desired change or changes. Oligonucleotide synthesis is well known in the art and readily automated to produce one or more nucleic acids having any desired codon change(s). Restriction sites, silent mutations, and favorable codon usage may also be introduced in this way. Alternatively, one or more codons can be altered to represent a subset of particular amino acids, e.g., a subset that excludes cysteines which can form disulfide linkages, and is limited to a defined region, for example, a CDR region or portion thereof. Alternatively, the region may be represented by a partially or entirely random set of amino acids (for additional details, see, e.g., U.S. Pat. Nos. 5,830,650; 5,798, 208; 5,824,514; 5,817,483; 5,814,476; 5,723,323; 4,528,266; 4,359,53; 5,840,479; and 5,869,644).

It is understood that the above approaches can be carried out in part or in full using polymerase chain reaction (PCR) which is well known in the art and has the advantage of incorporating oligonucleotides, e.g., primers or single stranded nucleic acids having, e.g., a desired alteration(s), into a double stranded nucleic acid and in amplified amounts suitable for other manipulations, such as genetic engineering into an appropriate expression or cloning vector. Such PCR can also be carried out under conditions that allow for misincorporation of nucleotides to thereby introduce additional variability into the nucleic acids being amplified. Experimental details for carrying out PCR and related kits, reagents, and primer design can be found, e.g., in U.S. Pat. Nos. 4,683,202; 4,683,195; 6,040,166; and 6,096,551. Methods for introducing CDR regions into antibody framework regions using primer-based PCR is described in, e.g., U.S. Pat. No. 5,858, 725. Methods for primer-based PCR amplification of antibody libraries (and libraries made according to method) employing a minimal set of primers capable of finding sequence homology with a larger set of antibody molecules, such that a larger and diverse set of antibody molecules can be efficiently amplified, is described, e.g., in U.S. Pat. Nos. 5,780,225; 6,303,313; and 6,479,243. Non PCR-based methods for performing site directed mutagenesis can also be used and include "Kunkel" mutagenesis that employs single-stranded uracil containing templates and primers that hybridize and introduce a mutation when passed through a particular strain of E. coli (see, e.g., U.S. Pat. No. 4,873,192).

Additional methods for varying an antibody sequence, or portion thereof, include nucleic acid synthesis or PCR of nucleic acids under nonoptimal (i.e., error-prone) conditions, denaturation and renaturation (annealing) of such nucleic acids, exonuclease and/or endonuclease digestion followed by reassembly by ligation or PCR (nucleic acid shuffling), or a combination of one or more of the foregoing techniques as described, for example, in U.S. Pat. Nos. 6,440,668; 6,238, 884; 6,171,820; 5,965,408; 6,361,974; 6,358,709; 6,352,842; 4,888,286; 6,337,186; 6,165,793; 6,132,970; 6,117,679; 5,830,721; and 5,605,793.

In certain embodiment, antibody libraries (or affinity maturation libraries) comprising a family of candidate antibody molecules having diversity in certain portions of the candidate antibody molecule, e.g., in one or more CDR regions (or a portion thereof), one or more framework regions, and/or one or more constant regions (e.g., a constant region having effector function) can be expressed and screened for desired properties using art recognized techniques (see, e.g., U.S. Pat. Nos. 6,291,161; 6,291,160; 6,291,159; and 6,291,158). For example, expression libraries of antibody variable domains having a diversity of CDR3 sequences and methods for producing human antibody libraries having a diversity of CDR3 sequences by introducing, by mutagenesis, a diversity of CDR3 sequences and recovering the library can be constructed (see, e.g., U.S. Pat. No. 6,248,516).

Finally, for expressing the affinity matured antibodies, nucleic acids encoding the candidate antibody molecules can be introduced into cells in an appropriate expression format, e.g., as full length antibody heavy and light chains (e.g., IgG), antibody Fab fragments (e.g., Fab, F(ab')$_2$), or as single chain antibodies (scFv) using standard vector and cell transfection/transformation technologies (see, e.g., U.S. Pat. Nos. 6,331, 415; 6,103,889; 5,260,203; 5,258,498; and 4,946,778).

B. Nucleic Acid Encoding Immunologic and Therapeutic Agents

Immune responses against amyloid deposits can also be induced by administration of nucleic acids encoding antibodies and their component chains used for passive immunization. Such nucleic acids can be DNA or RNA. A nucleic acid segment encoding an immunogen is typically linked to regulatory elements, such as a promoter and enhancer, that allow expression of the DNA segment in the intended target cells of a patient. For expression in blood cells, as is desirable for induction of an immune response, exemplary promoter and enhancer elements include those from light or heavy chain immunoglobulin genes and/or the CMV major intermediate early promoter and enhancer (Stinski, U.S. Pat. Nos. 5,168, 062 and 5,385,839). The linked regulatory elements and coding sequences are often cloned into a vector. For administration of double-chain antibodies, the two chains can be cloned in the same or separate vectors.

A number of viral vector systems are available including retroviral systems (see, e.g., Lawrie and Tumin, *Cur. Opin. Genet. Develop.* 3:102-109 (1993)); adenoviral vectors (see, e.g., Bett et al., *J. Virol.* 67:5911 (1993)); adeno-associated virus vectors (see, e.g., Zhou et al., *J. Exp. Med.* 179:1867 (1994)), viral vectors from the pox family including vaccinia virus and the avian pox viruses, viral vectors from the alpha virus genus such as those derived from Sindbis and Semliki Forest Viruses (see, e.g., Dubensky et al., *J. Virol.* 70:508 (1996)), Venezuelan equine encephalitis virus (see Johnston et al., U.S. Pat. No. 5,643,576) and rhabdoviruses, such as vesicular stomatitis virus (see Rose, U.S. Pat. No. 6,168,943) and papillomaviruses (Ohe et al., *Human Gene Therapy* 6:325 (1995); Woo et al., WO 94/12629 and Xiao & Brandsma, *Nucleic Acids. Res.* 24, 2630-2622 (1996)).

DNA encoding an immunogen, or a vector containing the same, can be packaged into liposomes. Suitable lipids and related analogs are described by Eppstein et al., U.S. Pat. No. 5,208,036, Felgner et al., U.S. Pat. No. 5,264,618, Rose, U.S. Pat. No. 5,279,833, and Epand et al., U.S. Pat. No. 5,283,185. Vectors and DNA encoding an immunogen can also be adsorbed to or associated with particulate carriers, examples of which include polymethyl methacrylate polymers and polylactides and poly (lactide-co-glycolides), see, e.g., McGee et al., *J. Micro Encap.* (1996).

Gene therapy vectors or naked polypeptides (e.g., DNA) can be delivered in vivo by administration to an individual patient, typically by systemic administration (e.g., intravenous, intraperitoneal, nasal, gastric, intradermal, intramuscular, subdermal, or intracranial infusion) or topical application (see e.g., Anderson et al., U.S. Pat. No. 5,399,346). The term "naked polynucleotide" refers to a polynucleotide not delivered in association with a transfection facilitating agent. Naked polynucleotides are sometimes cloned in a plasmid vector. Such vectors can further include facilitating agents such as bupivacaine (Weiner et al., U.S. Pat. No. 5,593,972). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The ACCEL™ Gene Delivery Device manufactured by Agricetus, Inc. Middleton Wis. is suitable. Alternatively, naked DNA can pass through skin into the blood stream simply by spotting the DNA onto skin with chemical or mechanical irritation (see Howell et al., WO 95/05853).

In a further variation, vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

II. Prophylactic and Therapeutic Methods

The present invention is directed inter alia to treatment of Alzheimer's and other amyloidogenic diseases by administration of therapeutic immunological reagents (e.g., humanized immunoglobulins) to specific epitopes within Aβ to a patient under conditions that generate a beneficial therapeutic response in a patient (e.g., induction of phagocytosis of Aβ, reduction of plaque burden, inhibition of plaque formation, reduction of neuritic dystrophy, improving cognitive function, and/or reversing, treating or preventing cognitive decline) in the patient, for example, for the prevention or treatment of an amyloidogenic disease. The invention is also directed to use of the disclosed immunological reagents (e.g., humanized immunoglobulins) in the manufacture of a medicament for the treatment or prevention of an amyloidogenic disease.

In one aspect, the invention provides methods of preventing or treating a disease associated with amyloid deposits of Aβ in the brain of a patient. Such diseases include Alzheimer's disease, Down's syndrome and cognitive impairment. The latter can occur with or without other characteristics of an amyloidogenic disease. Some methods of the invention comprise administering an effective dosage of an antibody that specifically binds to a component of an amyloid deposit to the patient. Such methods are particularly useful for preventing or treating Alzheimer's disease in human patients. Exemplary methods comprise administering an effective dosage of an antibody that binds to Aβ. Preferred methods comprise administering an effective dosage of an antibody that specifically binds to an epitope within residues 1-10 of Aβ, for example, antibodies that specifically bind to an epitope within residues 1-3 of Aβ, antibodies that specifically bind to an epitope within residues 1-4 of Aβ, antibodies that specifically bind to an epitope within residues 1-5 of Aβ, antibodies that specifically bind to an epitope within residues 1-6 of Aβ, antibodies that specifically bind to an epitope within residues 1-7 of Aβ, or antibodies that specifically bind to an epitope within residues 3-7 of Aβ. In yet another aspect, the invention features administering antibodies that bind to an epitope comprising a free N-terminal residue of Aβ. In yet another aspect, the invention features administering antibodies that bind to an epitope within residues of 1-10 of Aβ wherein residue 1 and/or residue 7 of Aβ is aspartic acid. In yet another aspect, the invention features administering antibodies that specifically bind to Aβ peptide without binding to full-length amyloid precursor protein (APP). In yet another aspect, the isotype of the antibody is human IgG1.

In yet another aspect, the invention features administering antibodies that bind to an amyloid deposit in the patient and induce a clearing response against the amyloid deposit. For example, such a clearing response can be effected by Fc receptor mediated phagocytosis.

Therapeutic agents of the invention are typically substantially pure from undesired contaminant. This means that an agent is typically at least about 50% w/w (weight/weight) pure, as well as being substantially free from interfering proteins and contaminants. Sometimes the agents are at least about 80% w/w and, more preferably at least 90 or about 95% w/w pure. However, using conventional protein purification techniques, homogeneous peptides of at least 99% w/w pure can be obtained.

The methods can be used on both asymptomatic patients and those currently showing symptoms of disease. The antibodies used in such methods can be human, humanized, chimeric or nonhuman antibodies, or fragments thereof (e.g., antigen binding fragments) and can be monoclonal or polyclonal, as described herein. In yet another aspect, the invention features administering antibodies prepared from a human immunized with Aβ peptide, which human can be the patient to be treated with antibody.

In another aspect, the invention features administering an antibody with a pharmaceutical carrier as a pharmaceutical composition. Alternatively, the antibody can be administered to a patient by administering a polynucleotide encoding at least one antibody chain. The polynucleotide is expressed to produce the antibody chain in the patient. Optionally, the polynucleotide encodes heavy and light chains of the antibody. The polynucleotide is expressed to produce the heavy and light chains in the patient. In exemplary embodiments, the patient is monitored for level of administered antibody in the blood of the patient.

The invention thus fulfills a longstanding need for therapeutic regimes for preventing or ameliorating the neuropathology and, in some patients, the cognitive impairment associated with Alzheimer's disease.

A. Patients Amenable to Treatment

Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods are especially useful for individuals who have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70. Treatment typically involves multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

B. Treatment Regimes and Dosages

In prophylactic applications, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicaments are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease.

In some methods, administration of agent reduces or eliminates myocognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. The term "immune response" or "immunological response" includes the development of a humoral (antibody mediated) and/or a cellular (mediated by antigen-specific T cells or their secretion products) response directed against an antigen in a recipient subject. Such a response can be an active response, i.e., induced by administration of immunogen, or a passive response, i.e., induced by administration of immunoglobulin or antibody or primed T-cells. Typically, the immune response is monitored and repeated, dosages are given if the immune response starts to wane.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages need to be titrated to optimize safety and efficacy.

For passive immunization with an antibody, the dosage ranges from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. In another example, dosages can be 0.5 mg/kg body weight or 15 mg/kg body weight or within the range of 0.5-15 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment involves administration in multiple dosages over a prolonged period, for example, of at least six months. Additional exemplary treatment regimes involve administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Antibody is usually administered on multiple occasions. Intervals between single dosages can be weekly, monthly or yearly. Intervals can also be irregular as indicated by measuring blood levels of antibody to Aβ in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, humanized antibodies show the longest half-life, followed by chimeric antibodies and nonhuman antibodies.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 200 mg of antibody per dose, with dosages of from 5 to 25 mg being more commonly used) at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding antibodies range from about 10 ng to 1 g, 100 ng to 100 mg, 1 µg to 10 mg, or 30-300 µg DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treatment of amyloidogenic disease. In certain embodiments, a humanized antibody of the invention (e.g., humanized 12A11) is administered in combination with a second immunogenic or immunologic agent. For example, a humanized 12A11 antibody of the invention can be administered in combination with another humanized antibody to Aβ. In other embodiments, a humanized 12A11 antibody is administered to a patient who has received or is receiving an Aβ vaccine. In the case of Alzheimer's and Down's syndrome, in which amyloid deposits occur in the brain, agents of the invention can also be administered in conjunction with other agents that increase passage of the agents of the invention across the blood-brain barrier. Agents of the invention can also be administered in combination with other agents that enhance access of the therapeutic agent to a target cell or tissue, for example, liposomes and the like. Coadministering such agents can decrease the dosage of a therapeutic agent (e.g., therapeutic antibody or antibody chain) needed to achieve a desired effect.

C. Pharmaceutical Compositions

Agents of the invention are often administered as pharmaceutical compositions comprising an active therapeutic agent, i.e., and a variety of other pharmaceutically acceptable components. See Remington's Pharmaceutical Science (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation, which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249: 1527 (1990) and Hanes, Advanced Drug Delivery Reviews 28:97 (1997)). The agents of this invention can be administered in the form of a depot injection or implant preparation, which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein.

Alternatively, transdermal delivery can be achieved using a skin patch or using transferosomes (Paul et al., *Eur. J. Immunol.* 25:3521 (1995); Cevc et al., *Biochem. Biophys. Acta* 1368:201-15 (1998)).

D. Monitoring the Course of Treatment

The invention provides methods of monitoring treatment in a patient suffering from or susceptible to Alzheimer's, i.e., for monitoring a course of treatment being administered to a patient. The methods can be used to monitor both therapeutic treatment on symptomatic patients and prophylactic treatment on asymptomatic patients. In particular, the methods are useful for monitoring passive immunization (e.g., measuring level of administered antibody).

Some methods involve determining a baseline value, for example, of an antibody level or profile in a patient, before administering a dosage of agent, and comparing this with a value for the profile or level after treatment. A significant increase (i.e., greater than the typical margin of experimental error in repeat measurements of the same sample, expressed as one standard deviation from the mean of such measurements) in value of the level or profile signals a positive treatment outcome (i.e., that administration of the agent has achieved a desired response). If the value for immune response does not change significantly, or decreases, a negative treatment outcome is indicated.

In other methods, a control value (i.e., a mean and standard deviation) of level or profile is determined for a control population. Typically the individuals in the control population have not received prior treatment. Measured values of the level or profile in a patient after administering a therapeutic agent are then compared with the control value. A significant increase relative to the control value (e.g., greater than one standard deviation from the mean) signals a positive or sufficient treatment outcome. A lack of significant increase or a decrease signals a negative or insufficient treatment outcome. Administration of agent is generally continued while the level is increasing relative to the control value. As before, attainment of a plateau relative to control values is an indicator that the administration of treatment can be discontinued or reduced in dosage and/or frequency.

In other methods, a control value of the level or profile (e.g., a mean and standard deviation) is determined from a control population of individuals who have undergone treatment with a therapeutic agent and whose levels or profiles have plateaued in response to treatment. Measured values of levels or profiles in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment may be indicated.

In other methods, a patient who is not presently receiving treatment but has undergone a previous course of treatment is monitored for antibody levels or profiles to determine whether a resumption of treatment is required. The measured level or profile in the patient can be compared with a value previously achieved in the patient after a previous course of treatment. A significant decrease relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucous fluid or cerebrospinal fluid from the patient. The sample is analyzed, for example, for levels or profiles of antibodies to Aβ peptide, e.g., levels or profiles of humanized antibodies. ELISA methods of detecting antibodies specific to Aβ are described in the Examples section. In some methods, the level or profile of an administered antibody is determined using a clearing assay, for example, in an in vitro phagocytosis assay, as described herein. In such methods, a tissue sample from a patient being tested is contacted with amyloid deposits (e.g., from a PDAPP mouse) and phagocytic cells bearing Fc receptors. Subsequent clearing of the amyloid deposit is then monitored. The existence and extent of clearing response provides an indication of the existence and level of antibodies effective to clear Aβ in the tissue sample of the patient under test.

The antibody profile following passive immunization typically shows an immediate peak in antibody concentration followed by an exponential decay. Without a further dosage, the decay approaches pretreatment levels within a period of days to months depending on the half-life of the antibody administered.

In some methods, a baseline measurement of antibody to Aβ in the patient is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment) administration of an additional dosage of antibody is indicated.

Additional methods include monitoring, over the course of treatment, any art-recognized physiologic symptom (e.g., physical or mental symptom) routinely relied on by researchers or physicians to diagnose or monitor amyloidogenic diseases (e.g., Alzheimer's disease). For example, one can monitor cognitive impairment. The latter is a symptom of Alzheimer's disease and Down's syndrome but can also occur without other characteristics of either of these diseases. For example, cognitive impairment can be monitored by determining a patient's score on the Mini-Mental State Exam in accordance with convention throughout the course of treatment.

E. Kits

The invention further provides kits for performing the monitoring methods described above. Typically, such kits contain an agent that specifically binds to antibodies to Aβ. The kit can also include a label. For detection of antibodies to Aβ, the label is typically in the form of labeled anti-idiotypic antibodies. For detection of antibodies, the agent can be supplied prebound to a solid phase, such as to the wells of a microtiter dish. Kits also typically contain labeling providing directions for use of the kit. The labeling may also include a chart or other correspondence regime correlating levels of measured label with levels of antibodies to Aβ. The term labeling refers to any written or recorded material that is attached to, or otherwise accompanies a kit at any time during its manufacture, transport, sale or use. For example, the term labeling encompasses advertising leaflets and brochures, packaging materials, instructions, audio or videocassettes, computer discs, as well as writing imprinted directly on kits.

The invention also provides diagnostic kits, for example, research, detection and/or diagnostic kits (e.g., for performing in vivo imaging). Such kits typically contain an antibody for binding to an epitope of Aβ, preferably within residues 1-10. Preferably, the antibody is labeled or a secondary labeling reagent is included in the kit. Preferably, the kit is labeled with instructions for performing the intended application, for example, for performing an in vivo imaging assay. Exemplary antibodies are those described herein.

F. In Vivo Imaging

The invention provides methods of in vivo imaging amyloid deposits in a patient. Such methods are useful to diagnose or confirm diagnosis of Alzheimer's disease, or susceptibility thereto. For example, the methods can be used on a patient presenting with symptoms of dementia. If the patient has abnormal amyloid deposits, then the patient is likely suffering from Alzheimer's disease. The methods can also be used on asymptomatic patients. Presence of abnormal deposits of amyloid indicates susceptibility to future symptomatic disease. The methods are also useful for monitoring disease progression and/or response to treatment in patients who have been previously diagnosed with Alzheimer's disease.

The methods work by administering a reagent, such as antibody that binds to Aβ, to the patient and then detecting the agent after it has bound. Preferred antibodies bind to Aβ deposits in a patient without binding to full length APP polypeptide. Antibodies binding to an epitope of Aβ within amino acids 1-10 are particularly preferred. In some methods, the antibody binds to an epitope within amino acids 7-10 of Aβ. Such antibodies typically bind without inducing a substantial clearing response. In other methods, the antibody binds to an epitope within amino acids 1-7 of Aβ. Such antibodies typically bind and induce a clearing response to Aβ. However, the clearing response can be avoided by using antibody fragments lacking a full-length constant region, such as Fabs. In some methods, the same antibody can serve as both a treatment and diagnostic reagent. In general, antibodies binding to epitopes C-terminal to residue 10 of Aβ do not show as strong a signal as antibodies binding to epitopes within residues 1-10, presumably because the C-terminal epitopes are inaccessible in amyloid deposits. Accordingly, such antibodies are less preferred.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity for Aβ is unlabelled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled loci, to corresponding baseline values. The base line values can represent the mean levels in a population of undiseased individuals. Baseline values can also represent previous levels determined in the same patient. For example, baseline values can be determined in a patient before beginning treatment, and measured values thereafter compared with the baseline values. A decrease in values relative to baseline signals a positive response to treatment.

The present invention will be more fully described by the following non-limiting examples.

EXAMPLES

The following Sequence identifiers are used throughout the Examples section to refer to immunoglobulin chain variable region nucleotide and amino acid sequences.

| Antibody | VL nucleotide sequence | VL amino acid sequence | VH nucleotide sequence | VH amino acid sequence |
|---|---|---|---|---|
| 12A11 | SEQ ID NO: 1 (coding) | SEQ ID NO: 2 | SEQ ID NO: 3 (coding) | SEQ ID NO: 4 |
| 12A11v1 | SEQ ID NO: 34 | SEQ ID NO: 7 | SEQ ID NO: 35 | SEQ ID NO: 10 |
| 12A11v2 | | SEQ ID NO: 7 | | SEQ ID NO: 13 |
| 12A11v2.1 | | SEQ ID NO: 7 | | SEQ ID NO: 14 |
| 12A11v3 | | SEQ ID NO: 7 | | SEQ ID NO: 15 |
| 12A11 | SEQ ID NO: 5 | | SEQ ID NO: 6 | |

As used herein, an antibody or immunoglobulin sequence comprising a VL and/or VH sequence as set forth in any one of SEQ ID NOs: 1-4 can comprise either the full sequence or can comprise the mature sequence (i.e., mature peptide without the signal or leader peptide).

Previous studies have shown that it is possible to predict in vivo efficacy of various Aβ antibodies in reducing AD-associated neuropathology (e.g., plaque burden) by the ability of antibodies to bind plaques ex vivo (e.g., in PDAPP or AD brain sections) and/or trigger plaque clearance in an ex vivo phagocytosis assay (Bard et al. (2000) *Nat. Med.* 6:916-919). The correlation supports the notion that Fc-dependent phagocytosis by microglial cells and/or macrophages is important to the process of plaque clearance in vivo. However, it has also been reported that antibody efficacy can also be obtained in vivo by mechanisms that are independent of Fc interactions (Bacskai et al. (2002) *J. Neurosci.* 22:7873-7878). Studies have indicated that an antibody directed against the midportion of Aβ, which cannot recognize amyloid plaques, appears to bind to soluble Aβ and reduce plaque deposition (DeMattos et al. (2001) *Proc. Natl. Acad. Sci. USA* 98:8850-8855).

In order to characterize potential in vivo efficacy of the murine monoclonal antibody 12A11 (isotype IgG1), various ex vivo assays were first performed.

Avidity of mAb 12A11 for Aβ-42. Binding of monoclonal antibody 12A11 to aggregated synthetic Aβ1-42 was performed by ELISA, as described in Schenk, et al. (*Nature* 400:173 (1999)). For comparison purposes, mAbs 12B4, and 10D5 were also assayed. Soluble Aβ1-42 refers to the synthetic Aβ1-42 peptide sonicated in dimethyl sulfoxide (DMSO). Serial dilutions of the antibodies at 20 µg/ml were incubated with 50,000 cpm [$^{125}$I]Aβ1-42 (190 µCi/µmol; labeling with Iodogen reagent, Pierce) overnight at room temperature. Fifty microliters of a slurry containing 75 mg/ml protein A Sepharose (Amersham Pharmacia) and 200 µg of rabbit anti-mouse IgG (H+L) (Jackson ImmunoResearch) were incubated with the diluted antibodies for 1 h at room temperature, washed twice, and counted on a Wallac gamma counter (Perkin-Elmer). All steps were performed in RIA buffer consisting of 10 mM Tris, 0.5 M NaCl, 1 mg/ml gelatin, and 0.5% Nonidet P-40, pH 8.0.

Results from the avidity study are shown below in Table 2.

TABLE 2

| Antibody | Epitope | Isotype | ED$_{50}$ on aggregated Aβ1-42, pM | % Capture of soluble Aβ1-42 |
|---|---|---|---|---|
| 10D5[†] | Aβ3-7 | IgG1 | 53 | 1 |
| 12B4[†] | Aβ3-7 | IgG2a | 667 | 8 |
| 12A11 | Aβ3-7 | IgG1 | 233 | 30 |

[†]Antibodies 10D5 and 12B4 are described in WO 02/46237 and International Patent Application Serial No. PCT/US03/07715, respectively.
*As a comparison, the antibody 266 at 10 µg/ml would capture 70% of Aβ1-42.

All of the antibodies tested exhibited a high avidity for aggregated Aβ1-42. Moreover, antibodies 12B4 and 12A11 appreciably captured soluble Aβ1-42 at antibody concentrations of 20 µg/ml. As shown in Table 2, the IgG1 antibody 12A11 captured Aβ1-42 more efficiently than the IgG2a antibody 12B4 or the IgG1 antibody 10D5.

The ability of various antibodies (including 12A11) to capture soluble Aβ was further assayed as follows. Various concentrations of antibody (up to 10 µg/ml) were incubated with 50,000 CPM of $^{125}$I-Aβ1-42 (or $^{125}$I-Aβ 1-40). The concentration of antibody sufficient to bind 25% of the radioactive counts was determined in a capture radioimmunoassay. For antibodies not capable of binding 25% of the counts at 10 µg/ml, the percentage of counts bound at 10 µg/ml was determined. The 12A11 bound 20% of the radioactive counts (i.e., $^{125}$I-Aβ at 10 µg/ml. This was greater than the amount bound by two other Aβ3-7 antibodies tested, namely 12B4 and 10D5 (binding 7% and 2% at 10 µg/ml, respectively). Thus, of the N-terminal (epitope Aβ3-7) antibodies tested, 12A11 exhibited the most appreciable ability to capture Aβ.

As a measure of their ability to trigger Fc-mediated plaque clearance, the antibodies were also compared in an ex vivo phagocytosis assay with primary mouse microglial cells and sections of brain tissue from PDAPP mice. Irrelevant IgG1 and IgG2a antibodies, having no reactivity toward Aβ or other components of the assay, were used as isotype-matched negative controls. Briefly, murine primary microglial cells were cultured with unfixed cryostat sections of PDAPP mouse brain in the presence of antibodies. After 24 h of incubation, the total level of Aβ remaining in the cultures was measured by ELISA. To quantify the degree of plaque clearance/Aβ degradation, Aβ was extracted from the cultures of microglia and brain sections (n=3) with 8 M urea for ELISA analysis. Data were analyzed with ANOVA followed by a post hoc Dunnett's test.

As shown in FIG. 1, the 12B4 antibody reduced Aβ levels efficiently (73% for 12B4; P<0.001) with 12A11 showing somewhat less, albeit statistically significant, efficiency (48% for 12A11, P<0.05). The 10D5 antibody did not significantly reduce Aβ levels. The performance of 12A11 in the ex vivo phagocytosis assay may be improved upon conversion to the IgG2a isotype which is a preferred isotype for microglial phagocytosis.

Example II

In Vivo Efficacy of Mouse 12A11 Antibody

Mouse Antibody 12A11 Reduces Alzheimer's-Like Neuropathology In Vivo To determine the in vivo efficacy of 12A11, antibodies (including 12A11, 12B4, or 10D5) were administered to mice at 10 mg/kg by weekly intraperitoneal injection for 6 months as described in Bard et al. (2000) *Nat. Med.* 6:916. At the end of the study, total levels of cortical Aβ were determined by ELISA. As shown in FIG. 2A, each of the antibodies significantly reduced total Aβ levels compared with the PBS control (P<0.001), i.e. 12B4 showed a 69% reduction, 10D5 showed a 52% reduction, and 12A11 showed a 31% reduction.

The level of neuritic dystrophy was then examined in sections of brain tissue from the above-mentioned mice to determine the association between plaque clearance and neuronal protection. Data from brain image analyses examining the percentage of frontal cortex occupied by neurotic dystrophy is shown in FIG. 2B. These data show that antibodies 10D5 and 12A11 were not effective at reducing neuritic dystrophy whereas 12B4 significantly reduced neuritic dystrophy (12B4, P<0.05; ANOVA followed by post hoc Dunnett's test), as determined by the assay described herein. Again, this activity of 12A11 may be improved by converting 12A11 to the IgG2a isotype (murine efficacy). Regarding humanized versions of 12A11, IgG1 isotypes are preferred for reducing neuritic dystrophy.

Experiments demonstrating the binding properties and in vivo efficacy of antibody 12A11 are also described in Bard, et al. *PNAS* 100:2023 (2003), incorporated by reference herein.

In summary, all antibodies had significant avidity for aggregated Aβ and triggered plaque clearance in an ex vivo assay. The IgG2a isotype (affinity for Fc receptors, in particular, FcγRI) appears to be an important attribute for both clearance of Aβ and protection against neuritic dystrophy. The antibody 12A11 (IgG1) captured soluble monomeric Aβ1-42 more efficiently than 12B4 (IgG2a) or 10D5 (IgG1) but was not as effective at reducing neuritic dystrophy. Enhanced efficacy in reducing plaque burden and reducing neuritic dystrophy may be achieved by engineering antibodies to have an isotype which maximally supports phagocytosis. Particularly efficacious antibodies bind to epitopes within the N terminus of Aβ.

Example III

Cloning and Sequencing of the Mouse 12A11 Variable Regions

Cloning and Sequence Analysis of 12A11 VH. The VH and VL regions of 12A11 from hybridoma cells were cloned by RT-PCR and 5' RACE using mRNA from hybridoma cells and standard cloning methodology. The nucleotide sequence (coding, SEQ ID NO:3) and deduced amino acid sequence (SEQ ID NO:4) derived from independent cDNA clones encoding the presumed 12A11 VH domain, are set forth in Table 3 and Table 4, respectively.

TABLE 3

Mouse 12A11 VH DNA sequence.

ATGGACAGGCTTACTACTTCATTCCTGCTGCTGATTGTCCCTGCATATGTCTT  (SEQ ID NO:3)

GTCCCAAGTTACTCTAAAAGAGTCTGGCCCTGGGATATTGAAGCCCTCACAG

ACCCTCAGTCTGACTTGTTCTTTCTCTGGGTTTTCACTGAGCACTTCTGGTAT

GAGTGTAGGCTGGATTCGTCAGCCTTCAGGGAAGGGTCTGGAGTGGCTGGC

ACACATTTGGTGGGATGATGATAAGTACTATAACCCATCCCTGAAGAGCCGG

CTCACAATCTCCAAGGATACCTCCAGAAACCAGGTATTCCTCAAGATCACCA

GTGTGGACACTGCAGATACTGCCACTTACTACTGTGCTGAAGAACTACTAC

GGCTGACTACTTTGCCTACTGGGGCCAAGGCACCACTCTCACAGTCTCCTCA

TABLE 4

Mouse 12A11 VH amino acid sequence mdrlttsflllivpayvlsQVTLKESGPGILKPSQTLSLTCSFSGFSLStsgmsvgWIRQPSGKG  (SEQ ID NO: 4)

LEWLAhiwwdddkyynpslksRLTISKDTSRNQVFLKITSVDTADTATYYCARrttttadyfa yWGQGTTLTVSS

\* Leader peptide and CDRs in lower case.

Cloning and Sequence Analysis of 12 μl VL. The light chain variable VL region of 12A11 was cloned in an analogous manner as the VH region. The nucleotide sequence (coding, SEQ ID NO:1) and deduced amino acid sequence (SEQ ID NO:2) derived from two independent cDNA clones encoding the presumed 12A11 VL domain, are set forth in Table 5 and Table 6, respectively.

The 12A11 VL and VH sequences meet the criteria for functional V regions in so far as they contain a contiguous ORF from the initiator methionine to the C-region, and share conserved residues characteristic of immunoglobulin V region genes. From N-terminal to C-terminal, both light and heavy chains comprise the domains FR1, CDR1, FR2, CDR2, FR3, CDR3 and FR4.

TABLE 5

Mouse 12A11 VL DNA sequence

ATGAAGTTGCCTGTTAGGCTGTTGGTGCTGATGTTCTGGATTCCTGCTTCCAG  (SEQ ID NO:1)

CAGTGATGTTTTGATGACCCAAACTCCACTCTCCCTGCCTGTCAGTCTTGGAG

ATCAAGCCTCCATCTCTTGCAGATCTAGTCAGAGCATTGTACATAGTAATGG

AAACACCTACTTAGAATGGTACCTGCAGAAACCAGGCCAGTCTCCAAAGCT

CCTGATCTACAAAGTTTCCAACCGATTTTCTGGGGTCCCAGACAGGTTCAGT

GGCAGTGGATCAGGGACAGATTTCACACTCAAGATCAGCAGAGTGGAGGCT

GAGGATCTGGGAATTTATTACTGCTTTCAAAGTTCACATGTTCCTCTCACGTT

CGGTGCTGGGACCAAGCTGGAGCTGAAA

TABLE 6

Mouse 12A11 VL amino acid sequence mklpvrllvlmfwipasssDVLMTQTPLSLPVSLGDQASISCrssqsivhsngntyleWYLQKPGQ  (SEQ ID NO: 2)

SPKLLIYkvsnrfsGVPDRFSGSGSGTDFTLKISRVEAEDLGIYYCfqsshvpltFGAGTK

LELK

\* Leader peptide and CDRs in lower case.

Example IV

Expression of Chimeric 12A11 Antibody

Expression of Chimeric 12 μl Antibody: The variable heavy and light chain regions were re-engineered to encode splice donor sequences downstream of the respective VDJ or VJ junctions, and cloned into the mammalian expression vector pCMV-hγ1 for the heavy chain, and pCMV-hκ1 for the light chain. These vectors encode human γ1 and Ck constant regions as exonic fragments downstream of the inserted variable region cassette. Following sequence verification, the heavy chain and light chain expression vectors were co-transfected into COS cells. Various heavy chain clones were independently co-transfected with different chimeric light chain clones to confirm reproducibility of the result. Antibodies were immunoprecipitated from COS cell conditioned media using protein A Sepharose. Antibody chains were detected on immunoblots of SDS-PAGE gels. Detection was accomplished using goat-anti-human-IgG (H+L) antibody at a 1:5000 dilution at room temperature for 1 hour. Significant quantities of 12A11H+L chain were detected in conditioned media.

Figure 4:
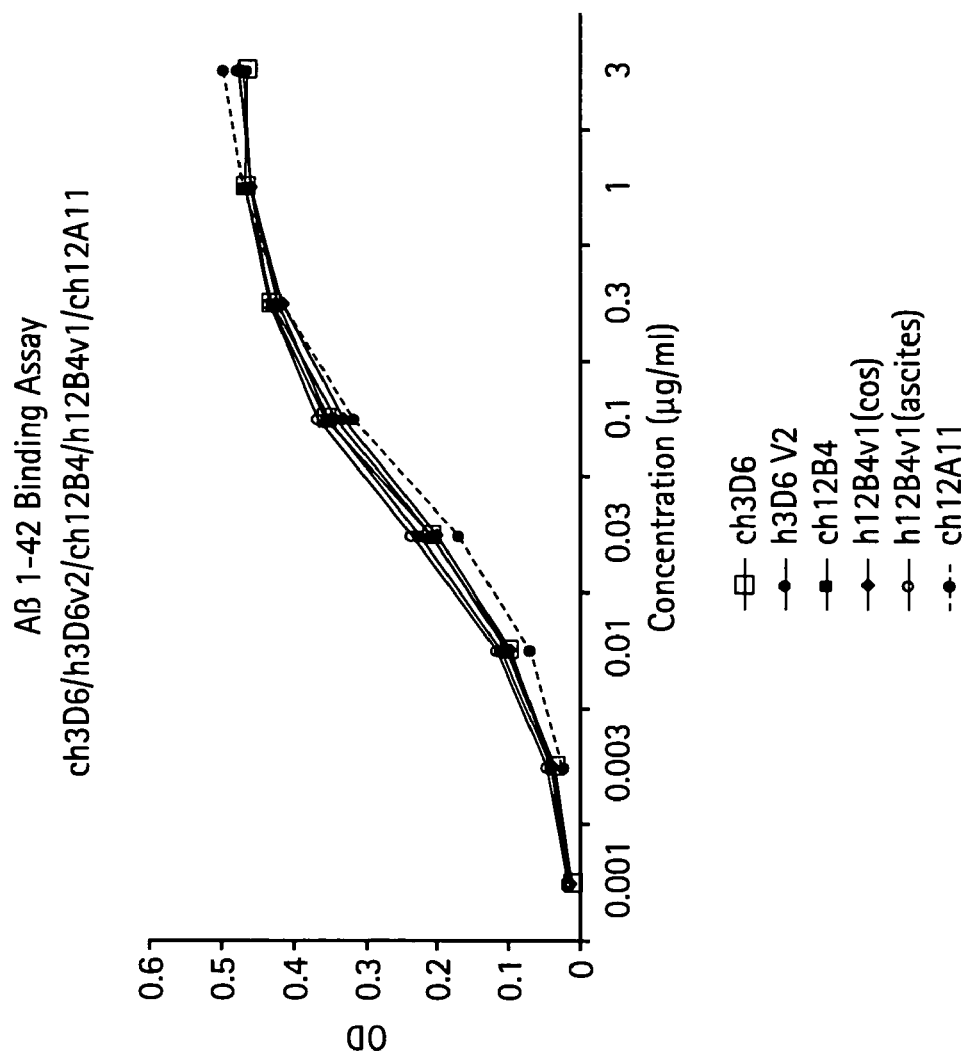
FIG. 4 graphically depicts the ELISA results from an experiment measuring the binding of chimeric 12A11, chimeric and humanized 3D6, and chimeric and humanized 12B4 to Aβ 1-42.

Direct binding of chimeric 12A11 antibody to Aβ was tested by ELISA assay. FIG. 4 demonstrates that chimeric 12A11 was found to bind to Aβ with high avidity, similar to that demonstrated by chimeric and humanized 3D6. (The cloning, characterization and humanization of 3D6 is described in U.S. patent application Ser. No. 10/010,942, the entire content of which is incorporated herein by this reference.) Binding avidity was also similar to that demonstrated by chimeric and humanized 12B4. (The cloning, characterization and humanization of 12B4 is described in U.S. patent application Ser. No. 10/388,214, the entire content of which is incorporated herein by this reference.)

Example V

12A11 Humanization

A. 12A11 Humanized Antibody, Version 1

Homology/Molecular Model Analysis. In order to identify key structural framework residues in the murine 12A11 antibody, three-dimensional models were studied for solved murine antibodies having homology to the 12A11 heavy and light chains. An antibody designated 1KTR was chosen having close homology to the 12A11 light chain and two antibodies designated 1ETZ and 1JRH were chosen having close homology to the 12A11 heavy chain. These mouse antibodies show strong sequence conservation with 12A11 (94% identity in 112 amino acids for Vk and 83% identity in 126 amino acids and 86% identity in 121 amino acids respectively for Vh). The heavy chain structure of 1ETZ was superimposed onto that of 1KTR. In addition, for Vk the CDR loops of the selected antibody fall into the same canonical Chothia structural classes as do the CDR loops of 12A11 VL. The crystal structures of these antibodies were examined for residues (e.g., FR residues important for CDR conformation, etc.) predicted be important for function of the antibody, and by comparison, function of the similar 12A11 antibody.

Selection of Human Acceptor Antibody Sequences. Suitable human acceptor antibody sequences were identified by computer comparisons of the amino acid sequences of the mouse variable regions with the sequences of known human antibodies. The comparison was performed separately for the 12A11 heavy and light chains. In particular, variable domains from human antibodies whose framework sequences exhibited a high degree of sequence identity with the murine VL and VH framework regions were identified by query of the NCBI Ig Database using NCBI BLAST™ (publicly accessible through the National Institutes of Health NCBI internet server) with the respective murine framework sequences.

Two candidate sequences were chosen as acceptor sequences based on the following criteria: (1) homology with the subject sequence; (2) sharing canonical CDR structures with the donor sequence; and/or (3) not containing any rare amino acid residues in the framework regions. The selected acceptor sequence for VL is BAC01733 in the NCBI Ig nonredundant database. The selected acceptor sequence for VH is AAA69734 in the NCBI Ig non-redundant database. AAA69734 is a human subgroup III antibody (rather than subgroup II) but was selected as an initial acceptor antibody based at least in part on the reasoning in Saldanha et al. (1999) *Mol. Immunol.* 36:709. First versions of humanized 12A11 antibody utilize these selected acceptor antibody sequences. The antibody is described in Schroeder and Wang (1990) *Proc. Natl. Acad. Sci. USA* 872:6146.

Substitution of Amino Acid Residues. As noted supra, the humanized antibodies of the invention comprise variable framework regions substantially from a human immunoglobulin (acceptor immunoglobulin) and complementarity determining regions substantially from a mouse immunoglobulin (donor immunoglobulin) termed 12A11. Having identified the complementarity determining regions of 12A11 and appropriate human acceptor immunoglobulins, the next step was to determine which, if any, residues from these components to substitute to optimize the properties of the resulting humanized antibody.

Reshaped Light Chain V Region:

The amino acid alignment of the reshaped light chain V region is shown in FIG. 5A. The choice of the acceptor framework (BAC01733) is from the same human subgroup as that which corresponds to the murine V region, has no unusual framework residues, and the CDRs belong to the same Chothia canonical structure groups. No backmutations were made in Version 1 of humanized 12A11.

Reshaped Heavy Chain V Region:

The amino acid alignment of the reshaped heavy chain V region is shown in FIG. 5B. The choice for the acceptor framework (AAA69734) is from human subgroup III (as described previously) and has no unusual framework residues. Structural analysis of the murine VH chain (1ETZ and 1JRH), in conjunction with the amino acid alignment of AAA69734 to the murine sequence dictates 9 backmutations in version 1 (v1) of the reshaped heavy chain: A24F T28S F29L V37I V48L F67L R71K N73T L78V (Kabat numbering). The back mutations are highlighted by asterisks in the amino-acid alignment shown in FIG. 5B.

Of the 9 back mutations, 3 are dictated by the model because the residues are canonical residues (A24F, F29L, & R71K, solid fill), i.e. framework residues which may contribute to antigen binding by virtue of proximity to CDR residues. There is one back mutation in the next most important class of residues, the interface residues involved in VH-VL packing interactions (underlined), i.e., V37I. The N73T mutation is at a vernier residue (dotted fill) on the edge of the binding site, possibly interacting with S30 adjacent to CDR1. The remaining 4 residues targeted for back mutation (T28S, V48L, F67L, L78V, Kabat numbering) also fall into the vernier class (indirect contribution to CDR conformation, dotted fill in FIG. 5B).

A summary of the changes incorporated into version 1 of humanized 12A11 is presented in Table 7.

TABLE 7

Summary of changes in humanized 12A11.v1

| Changes Hu->Mu: | VL (112 residues) 0/112 | VH (120 residues) 9/120 |
|---|---|---|
| Framework CDR1 | 5/16 | 6/7 |
| CDR2 | 3/7 | 10/16 |
| CDR3 | 6/8 | 8/11 |
| Total Hu->Mu | 14/112 (12.5%) | 33/120 (27.5%) |
| Mu->Hu: Framework Backmutation notes | 11/112 none | 26/120 1. Canonical: A24F, F29L, R71K 2. Packing: V37I 3. Vernier: T28S, V48L, F67L, N73T, L78V |
| Acceptor notes | 4. Genbank Acc. no. BAC01733 5. CDRs from same canonical structural group as donor mouse; 6. Immunoglobulin kappa light chain K64(AIMS4) | 7. Genbank Acc. no. AAA69734 (H1 - class 1, H2 = class 3) 8. CDRs from same canonical structural group as donor mouse 9. fetal Ig |

Tables 8 and 9 set forth Kabat numbering keys for the various light and heavy chains, respectively.

TABLE 8

Key to Kabat Numbering for 12A11 Light Chain

| KAB # | # | TYPE | mouse 12A11 VL | HUM 12A11 VL | BAC 01733 | A19-Germ-line | Comment |
|---|---|---|---|---|---|---|---|
| 1 | 1 | FR1 | D | D | D | D | |
| 2 | 2 | | V | V | V | I | canonical |
| 3 | 3 | | L | V | V | V | |
| 4 | 4 | | M | M | M | M | vernier |
| 5 | 5 | | T | T | T | T | |
| 6 | 6 | | Q | Q | Q | Q | |
| 7 | 7 | | T | S | S | S | |
| 8 | 8 | | P | P | P | P | |
| 9 | 9 | | L | L | L | L | |
| 10 | 10 | | S | S | S | S | |
| 11 | 11 | | L | L | L | L | |
| 12 | 12 | | P | P | P | P | |
| 13 | 13 | | V | V | V | V | |
| 14 | 14 | | S | T | T | T | |
| 15 | 15 | | L | P | P | P | |
| 16 | 16 | | G | G | G | G | |
| 17 | 17 | | D | E | E | E | |
| 18 | 18 | | Q | P | P | P | |
| 19 | 19 | | A | A | A | A | |
| 20 | 20 | | S | S | S | S | |
| 21 | 21 | | I | I | I | I | |
| 22 | 22 | | S | S | S | S | |
| 23 | 23 | | C | C | C | C | |
| 24 | 24 | CDR1 | R | R | R | R | |
| 25 | 25 | | S | S | S | S | |
| 26 | 26 | | S | S | S | S | |
| 27 | 27 | | Q | Q | Q | Q | |
| 27A | 28 | | S | S | S | S | |
| 27B | 29 | | I | I | L | L | |
| 27C | 30 | | V | V | L | L | |
| 27D | 31 | | H | H | H | H | |
| 27E | 32 | | S | S | S | S | |
| 28 | 33 | | N | N | N | N | |
| 29 | 34 | | G | G | G | G | |
| 30 | 35 | | N | N | Y | Y | |
| 31 | 36 | | T | T | N | N | |
| 32 | 37 | | Y | Y | Y | Y | |
| 33 | 38 | | L | L | L | L | |
| 34 | 39 | | E | E | D | D | |
| 35 | 40 | FR2 | W | W | W | W | |

TABLE 8-continued

Key to Kabat Numbering for 12A11 Light Chain

| KAB # | # | TYPE | mouse 12A11 VL | HUM 12A11 VL | BAC 01733 | A19-Germ-line | Comment |
|---|---|---|---|---|---|---|---|
| 36 | 41 | | Y | Y | Y | Y | packing |
| 37 | 42 | | L | L | L | L | |
| 38 | 43 | | Q | Q | Q | Q | packing |
| 39 | 44 | | K | K | K | K | |
| 40 | 45 | | P | P | P | P | vernier |
| 41 | 46 | | G | G | G | G | |
| 42 | 47 | | Q | Q | Q | Q | |
| 43 | 48 | | S | S | S | S | |
| 44 | 49 | | P | P | P | P | packing |
| 45 | 50 | | K | Q | Q | Q | |
| 46 | 51 | | L | L | L | L | packing |
| 47 | 52 | | L | L | L | L | vernier |
| 48 | 53 | | I | I | I | I | canonical |
| 49 | 54 | | Y | Y | Y | Y | vernier |
| 50 | 55 | CDR2 | K | K | L | L | |
| 51 | 56 | | V | V | G | G | |
| 52 | 57 | | S | S | S | S | |
| 53 | 58 | | N | N | N | N | |
| 54 | 59 | | R | R | R | R | |
| 55 | 60 | | F | F | A | A | |
| 56 | 61 | | S | S | S | S | |
| 57 | 62 | FR3 | G | G | G | G | |
| 58 | 63 | | V | V | V | V | |
| 59 | 64 | | P | P | P | P | |
| 60 | 65 | | D | D | D | D | |
| 61 | 66 | | R | R | R | R | |
| 62 | 67 | | F | F | F | F | |
| 63 | 68 | | S | S | S | S | |
| 64 | 69 | | G | G | G | G | canonical |
| 65 | 70 | | S | S | S | S | |
| 66 | 71 | | G | G | G | G | vernier |
| 67 | 72 | | S | S | S | S | |
| 68 | 73 | | G | G | G | G | vernier |
| 69 | 74 | | T | T | T | T | vernier |
| 70 | 75 | | D | D | D | D | |
| 71 | 76 | | F | F | F | F | canonical |
| 72 | 77 | | T | T | T | T | |
| 73 | 78 | | L | L | L | L | |
| 74 | 79 | | K | K | K | K | |
| 75 | 80 | | I | I | I | I | |
| 76 | 81 | | S | S | S | S | |
| 77 | 82 | | R | R | R | R | |
| 78 | 83 | | V | V | V | V | |
| 79 | 84 | | E | E | E | E | |
| 80 | 85 | | A | A | A | A | |
| 81 | 86 | | E | E | E | E | |
| 82 | 87 | | D | D | D | D | |
| 83 | 88 | | L | V | V | V | |
| 84 | 89 | | G | G | G | G | |
| 85 | 90 | | I | V | V | V | |
| 86 | 91 | | Y | Y | Y | Y | |
| 87 | 92 | | Y | Y | Y | Y | packing |
| 88 | 93 | | C | C | C | C | |
| 89 | 94 | CDR3 | F | F | M | M | |
| 90 | 95 | | Q | Q | Q | Q | |
| 91 | 96 | | S | S | A | A | |
| 92 | 97 | | S | S | L | L | |
| 93 | 98 | | H | H | Q | Q | |
| 94 | 99 | | V | V | T | T | |
| 95 | 100 | | P | P | P | P | |
| 96 | 101 | | L | L | Y | | |
| 97 | 102 | | T | T | T | | |
| 98 | 103 | FR4 | F | F | F | | packing |
| 99 | 104 | | G | G | G | | |
| 100 | 105 | | A | Q | Q | | |
| 101 | 106 | | G | G | G | | |
| 102 | 107 | | T | T | T | | |
| 103 | 108 | | K | K | K | | |
| 104 | 109 | | L | L | L | | |
| 105 | 110 | | E | E | E | | |
| 106 | 111 | | L | I | I | | |
| 106A | 112 | | K | K | K | | |

TABLE 9

Key to Kabat Numbering for 12A11 Heavy Chain

| KAB # | # | TYPE | Mouse 12A11 VH | HUM 12A11 VHv1 | AAA 69734 | 567123 Germline | Comment |
|---|---|---|---|---|---|---|---|
| 1 | 1 | FR1 | Q | Q | Q | Q | |
| 2 | 2 | | V | V | V | V | vernier |
| 3 | 3 | | T | Q | Q | Q | |
| 4 | 4 | | L | L | L | L | |
| 5 | 5 | | K | V | V | V | |
| 6 | 6 | | E | E | E | E | |
| 7 | 7 | | S | S | S | S | |
| 8 | 8 | | G | G | G | G | |
| 9 | 9 | | P | G | G | G | |
| 10 | 10 | | G | G | G | G | |
| 11 | 11 | | I | V | V | V | |
| 12 | 12 | | L | V | V | V | |
| 13 | 13 | | K | Q | Q | Q | |
| 14 | 14 | | P | P | P | P | |
| 15 | 15 | | S | G | G | G | |
| 16 | 16 | | Q | R | R | R | |
| 17 | 17 | | T | S | S | S | |
| 18 | 18 | | L | L | L | L | |
| 19 | 19 | | S | R | R | R | |
| 20 | 20 | | L | L | L | L | |
| 21 | 21 | | T | S | S | S | |
| 22 | 22 | | C | C | C | C | |
| 23 | 23 | | S | A | A | A | |
| 24 | 24 | | F | F | A | A | canonical for H1 - backmutate in v1 |
| 25 | 25 | | S | S | S | S | |
| 26 | 26 | | G | G | G | G | canonical |
| 27 | 27 | | F | F | F | F | canonical |
| 28 | 28 | | S | S | T | T | vernier, close to H1 - backmutate in v1 |
| 29 | 29 | | L | L | F | F | canonical for H1 - backmutate in v1 |
| 30 | 30 | | S | S | S | S | |
| 31 | 31 | CDR1 | T | T | S | S | |
| 32 | 32 | | S | S | Y | Y | |
| 33 | 33 | | G | G | A | A | |
| 34 | 34 | | M | M | M | M | |
| 35 | 35 | | S | S | H | H | |
| 35A | 36 | | V | V | — | — | |
| 35B | 37 | | G | G | — | — | |
| 36 | 38 | FR2 | W | W | W | W | |
| 37 | 39 | | I | I | V | V | packing - bacmutate in v1 |
| 38 | 40 | | R | R | R | R | |
| 39 | 41 | | Q | Q | Q | Q | packing |
| 40 | 42 | | P | A | A | A | |
| 41 | 43 | | S | P | P | P | |
| 42 | 44 | | G | G | G | G | |
| 43 | 45 | | K | K | K | K | |
| 44 | 46 | | G | G | G | G | |
| 45 | 47 | | L | L | L | L | packing |
| 46 | 48 | | E | E | E | E | |
| 47 | 49 | | W | W | W | W | packing |
| 48 | 50 | | L | L | V | V | vernier (underneath H2) - backmutate in v1 |
| 49 | 51 | | A | A | A | A | |
| 50 | 52 | CDR2 | H | H | V | V | |
| 51 | 53 | | I | I | I | I | |
| 52 | 54 | | W | W | S | S | |
| 53 | 55 | | W | W | Y | Y | |
| 54 | 56 | | D | D | D | D | |
| 55 | 57 | | D | D | G | G | |
| | | | — | — | S | S | |
| 56 | 58 | | D | D | N | N | |
| 57 | 59 | | K | K | K | K | |
| 58 | 60 | | Y | Y | Y | Y | |
| 59 | 61 | | Y | Y | Y | Y | |
| 60 | 62 | | N | N | A | A | |
| 61 | 63 | | P | P | D | D | |
| 62 | 64 | | S | S | S | S | |
| 63 | 65 | | L | L | V | V | |
| 64 | 66 | | K | K | K | K | |
| 65 | 67 | | S | S | G | G | |
| 66 | 68 | FR3 | R | R | R | R | |

TABLE 9-continued

Key to Kabat Numbering for 12A11 Heavy Chain

| KAB # | # | TYPE | Mouse 12A11 VH | HUM 12A11 VHv1 | AAA 69734 | 567123 Germline | Comment |
|---|---|---|---|---|---|---|---|
| 67 | 69 | | L | L | F | F | vernier (underneath H2, possibly interacting with L63) - backmutate in v1 |
| 68 | 70 | | T | T | T | T | |
| 69 | 71 | | I | I | I | I | |
| 70 | 72 | | S | S | S | S | |
| 71 | 73 | | K | K | R | R | canonical for H2 - backmutate in v1 |
| 72 | 74 | | D | D | D | D | |
| 73 | 75 | | T | T | N | N | vernier (edge of binding site, possibly interacting with S30) - backmutate in v1 |
| 74 | 76 | | S | S | S | S | |
| 75 | 77 | | R | K | K | K | |
| 76 | 78 | | N | N | N | N | |
| 77 | 79 | | Q | T | T | T | |
| 78 | 80 | | V | V | L | L | vernier (buried under H1, possibly interacting with V35A) - backmutate in v1 |
| 79 | 81 | | F | Y | Y | Y | |
| 80 | 82 | | L | L | L | L | |
| 81 | 83 | | K | Q | Q | Q | |
| 82 | 84 | | I | M | M | M | |
| 82A | 85 | | T | N | N | N | |
| 82B | 86 | | S | S | S | S | |
| 82C | 87 | | V | L | L | L | |
| 83 | 88 | | D | R | R | R | |
| 84 | 89 | | T | A | A | A | |
| 85 | 90 | | A | E | E | E | |
| 86 | 91 | | D | D | D | D | |
| 87 | 92 | | T | T | T | T | |
| 88 | 93 | | A | A | A | A | |
| 89 | 94 | | T | V | V | V | |
| 90 | 95 | | Y | Y | Y | Y | |
| 91 | 96 | | Y | Y | Y | Y | packing |
| 92 | 97 | | C | C | C | C | |
| 93 | 98 | | A | A | A | A | packing |
| 94 | 99 | | R | R | R | R | canonical |
| | | | — | — | D | D | |
| 95 | 100 | CDR3 | R | R | R | — | |
| 96 | 101 | | T | T | H | — | |
| 97 | 102 | | T | T | S | — | |
| 98 | 103 | | T | T | S | — | |
| 99 | 104 | | A | A | S | A | |
| 100 | 105 | | D | D | W | K | |
| 100A | 106 | | Y | Y | Y | L | |
| 100B | 107 | | F | F | Y | L | |
| 101 | 108 | | A | A | G | M | |
| 102 | 109 | | Y | Y | M | L | |
| | | | — | — | D | L | |
| | | | — | — | V | I | |
| 103 | 110 | | W | W | W | S | packing |
| 104 | 111 | | G | G | G | G | |
| 105 | 112 | | Q | Q | Q | A | |
| 106 | 113 | | G | G | G | K | |
| 107 | 114 | FR4 | T | T | T | G | |
| 108 | 115 | | T | T | T | Q | |
| 109 | 116 | | L | V | V | W | |
| 110 | 117 | | T | T | T | S | |
| 111 | 118 | | V | V | V | P | |
| 112 | 119 | | S | S | S | S | |
| 113 | 120 | | S | S | S | L | |

The humanized antibodies preferably exhibit a specific binding affinity for Aβ of at least $10^7$, $10^8$, $10^9$ or $10^{10}$ $M^{-1}$. Usually the upper limit of binding affinity of the humanized antibodies for Aβ is within a factor of three, four or five of that of 12A11 (i.e., ~$10^9$ $M^{-1}$). Often the lower limit of binding affinity is also within a factor of three, four or five of that of 12A11.

Assembly and Expression of Humanized 12A11 VH and VL, Version 1

PCR-mediated assembly was used to generate h12A11 v1 using appropriate oligonucleotide primers. The nucleotide sequences of humanized 12A11VL (version 1) (SEQ ID NO:34) and 12A11VH (version 1) (SEQ ID NO: 35) are listed below in Tables 10 and 11, respectively.

TABLE 10

Nucleotide sequence of humanized 12A11VLv1.

atgaggctccctgctcagctcctggggctgctgatgctctgggtctctggctccagtgggGATGTTGTGAT (SEQ ID NO:34)
GACCCAATCTCCACTCTCCCTGCCTGTCACTCCTGGAGAGCCAGCCTCCATCTCTTGCAGATCTAGTCAGA
GCATTGTGCATAGTAATGGAAACACCTACCTGGAATGGTACCTGCAGAAACCAGGCCAGTCTCCACAGCTC
CTGATCTACAAAGTTTCCAACCGATTTTCTGGGGTCCCAGACAGGTTCAGTGGCAGTGGATCAGGGACAGA
TTTCACACTCAAGATCAGCAGAGTGGAGGCTGAGGATGTGGGAGTTTATTACTGCTTTCAAAGTTCACATG
TTCCTCTCACCTTCGGTCAGGGGACCAAGCTGGAGATCAAA (uppercase VL segment only) leader peptide encoded by A19 germline seq derived from x63397 leader peptide

TABLE 11

Nucleotide sequence of humanized 12A11VHv1 atggagtttgggctgagctgggttttcctcgttgctcttctgagaggtgtccagtgtCAAGTTCAGCTGGT (SEQ ID NO:35)
GGAGTCTGGCGGCGGGGTGGTGCAGCCCGGACGGTCCCTCAGGCTGTCTTGTGCTTTCTCTGGGTTTTCAC
TGAGCACTTCTGGTATGAGTGTGGGCTGGATTCGTCAGGCTCCAGGGAAGGGTCTGGAGTGGCTGGCACAC
ATTTGGTGGGATGATGATAAGTACTATAACCCATCCCTGAAGAGCCGGCTCACAATCTCCAAGGATACCTC
CAAAAACACCGTGTACCTCCAGATGAACAGTCTGCGGGCTGAAGATACTGCCGTGTACTACTGTGCTCGAA
GAACTACTACCGCTGACTACTTTGCCTACTGGGGCCAAGGCACCACTGTCACAGTCTCCTCA Leader peptide (lower case) derived from VH donor seq accession M34030.1/aaa69734/M72

The amino acid sequences of humanized 12A11 VL (version 1) (SEQ ID NO:7) and 12A11 VH (version 1) (SEQ ID NO: 10) are depicted in FIGS. 5A and 5B, respectively.

B. Humanized 12A11 Antibodies—Versions 2, 2.1 and 3

The vernier residues (e.g., S28T, V48L, F67L, L78V) contribute indirectly to CDR conformation and were postulated to be of least significance for conformational perturbation. The targeted residues were mutated by site-directed mutagenesis using a kit by Strategene and h12A11VHv1 in a pCRS plasmid as the mutagenesis template to arise at clones corresponding to version 2. A sequenced verified V-region insert of version 2 was subcloned into the BamHI/HindIII sites of the heavy chain expression vector pCMV-Cgamma1 to produce recombinant h12A11v2 antibody. A version 2.1 antibody was similarly created having each of the above vernier residue mutations (i.e., elimination of backmutations) in addition to mutation at position T73N. A version 3 antibody likewise had each of the above mutations, S28T, L48V, L67F, V78L, T73N in addition to a mutation at position K71R.

C. Humanized 12A11 Antibodies—Versions 4 to 6

Additional humanized 12A11 versions were designed which retained backmutations at canonical and packing residues but eliminated backmutations at one (versions 4.1 to 4.4), two (versions 5.1 to 5.6) or three (versions 6.1 to 6.4) vernier residues. Site-directed mutagenesis and clone construction was performed as described in subpart C, above. Recombinant antibodies were expressed in COS cells and purified from COS cell supernatants. Additional versions may include combinations of the above, for example, human residues at 1, 2, 3, 4 or 5 vernier residues in combination with at least one packing and/or canonical residue (e.g., human residues at positions 28, 37, 48, 67, 71 and 78 or human residues at positions 28, 37, 48, 67, 71, 73 and 78).

D. Humanized 12A11 Antibodies—Versions 7 and 8

A seventh version of humanized 12A11 is created having each of the backmutations indicated for version 1, except for the T→S backmutation at residue 28 (vernier), and the V→I backmutation at residue 37 (packing). An eighth version of humanized 12A11 is created having each of the backmutations indicated for version 1, except for the N→T backmutation at residue 73 (vernier). The amino acid sequences of humanized 12A11 version 7 and 8 heavy chains are set forth as SEQ ID NOs: 30 and 31 respectively.

As compared to version 1, version 7 contains only 7 backmutations. The T28S backmutation is conservative and is eliminated in version 7 of the heavy chain. The backmutation at packing residue V37I is also eliminated in version 7. As compared to version 1, version 7 contains only 8 backmutations. In version 8, the N73T (vernier) backmutation is eliminated.

Additional versions may include combinations of the above, for example, human residues (e.g., elimination of backmutations) at 1, 2, 3, 4 (or 5) residues selected from positions 28, 48, 78 and 73, optionally in combination with elimination of backmutation at least one packing residue (e.g., position 37) and/or at least one canonical residue.

Example VI

Functional Testing of Humanized 12A11 Antibodies

Humanized 12A11 version 1 was cloned as described in Example V. Humanized 12A11 was produced by transient expression in COS cells, and purified according to art-recognized methodologies. The binding activity of the humanized antibody was first demonstrated by a qualitative ELISA assay (data not shown). Humanized 12A11 version 1 was further compared to its murine and chimeric counterparts for two properties: antigen binding (quantitative Aβ ELISA) and relative affinity. The binding activity of h12A11v1 was demonstrated in the quantitative Aβ ELISA and found to be identical with murine and chimeric forms of 12A11 (see FIG. 7).

The affinity of h12A11 v1 antibody was also compared with murine and chimeric 12A11 antibodies by a competitive Aβ ELISA. For the competitive binding assay, a biotin conjugated recombinant mouse 12A11Cγ2a (isotype switched 12A11) was used. The binding activity of the biotinylated m12A11Cγ2a for aggregate Aβ1-42 was confirmed by an ELISA assay using strepavidin-HRP as reporter. A direct comparison of Aβ binding by the two isoforms of 12A11 (Cγ1, Cγ2a), using HRP conjugated goat anti-mouse HRP as reporter, confirmed that the biotin conjugated recombinant 12A11Cγ2a is comparable to the original Cγ1 mouse antibody.

Competition binding study employed the biotin conjugated ml 2A11Cγ2a at a fixed concentration and competing with a range of concentrations of test antibodies as indicated in FIG. 8. FIG. 8 shows the result of h12A11v1 competitive assay comparing h12A11v1 with chimeric and murine forms. The humanized 12A11v1 competed within 2×IC50 value with its murine and chimeric counterparts. This data is consistent with affinity determination using Biacore technology (data not shown), which indicated KD values of 38 nM and 23 nM for the murine Cγ2a and h12A11v1, respectively. In summary, the findings suggest h12A11 v1 retains the antigen binding properties and affinity of its original murine counterpart.

COS cells were transiently transfected with different combinations of humanized 12A11VH and h12A11VLv1. The conditioned media was collected 72 hours post-transfection. Antibody concentration in conditioned media from transfected COS cells was determined by a quantitative human IgG ELISA. Quantitative Aβ (1-42) aggregate binding assay confirmed that h12A11v2, v2.1 and v3 are comparable to h12A11v1 and to chimeric 12A11 for antigen binding. Moreover, versions 5.1-5.6 and 6.1-6.3 exhibit similar binding activities when tested in this binding assay. Version 6.4 showed some loss of activity in the assay but activity was notably restored in v2.

Binding properties for murine 12A11 and h12A11v1 were also compared using BIAcore technology. Murine 12A11 and h12A11v1 exhibited similar binding profiles when exposed to either low- or high-density immobilized Aβ peptide (bio-DAE peptide). Kinetic analysis of murine 12A11 versus h12A11v1 was also performed. In these studies the BIAcore technology was used to measure the binding of soluble antibody to solid phase bound biotinylated DAE peptide. The peptide was immobilized on streptavidin biosensor chips then, varying concentrations of each antibody were applied in triplicates and the binding was measured as a function of time. The kinetic data was analyzed using BIAevaluation software applied to a bivalent model. The apparent dissociation ($k_d$) and association ($k_a$) rate constants were calculated from the appropriate regions of the sensorgrams using a global analysis. The affinity constant of the interaction between bio-DAE10 and the antibodies was calculated from the kinetic rate constants. From these measurements the apparent dissociation (kd) and association (ka) rate constants were derived and used to calculate a $K_D$ value for the interaction. Table 12 includes a summary of kinetic analysis of Aβ binding of 12A11 antibodies as determined by BIAcore analysis.

TABLE 12

Bivalent Model (global analysis)

| Antibody | $K_a$ (1/Ms) | $K_d$ (1/s) | KA (1/M) | KD (nM) | Chi2 |
|---|---|---|---|---|---|
| m12A11 | 1.05E+05 | 3.98E-03 | 2.64E+07 | 38.00 | 0.247 |
| h12A11v1 | 1.47E+05 | 3.43E-03 | 4.29E+07 | 23.30 | 0.145 |

The data indicate that humanized 12A11v1 has a similar affinity for Aβ peptide when compare with parental murine 12A11.

Example VII

Prevention and Treatment of Human Subjects

A single-dose phase I trial is performed to determine safety in humans. A therapeutic agent is administered in increasing dosages to different patients starting from about 0.01 the level of presumed efficacy, and increasing by a factor of three until a level of about 10 times the effective mouse dosage is reached.

A phase II trial is performed to determine therapeutic efficacy. Patients with early to mid Alzheimer's Disease defined using Alzheimer's disease and Related Disorders Association (ADRDA) criteria for probable AD are selected. Suitable patients score in the 12-26 range on the Mini-Mental State Exam (MMSE). Other selection criteria are that patients are likely to survive the duration of the study and lack complicating issues such as use of concomitant medications that may interfere. Baseline evaluations of patient function are made using classic psychometric measures, such as the MMSE, and the ADAS, which is a comprehensive scale for evaluating patients with Alzheimer's Disease status and function. These psychometric scales provide a measure of progression of the Alzheimer's condition. Suitable qualitative life scales can also be used to monitor treatment. Disease progression can also be monitored by MRI. Blood profiles of patients can also be monitored including assays of immunogen-specific antibodies and T-cells responses.

Following baseline measurements, patients begin receiving treatment. They are randomized and treated with either therapeutic agent or placebo in a blinded fashion. Patients are monitored at least every six months. Efficacy is determined by a significant reduction in progression of a treatment group relative to a placebo group.

A second phase II trial is performed to evaluate conversion of patients from non-Alzheimer's Disease early memory loss, sometimes referred to as age-associated memory impairment (AAMI) or mild cognitive impairment (MCI), to probable Alzheimer's disease as defined as by ADRDA criteria. Patients with high risk for conversion to Alzheimer's Disease are selected from a non-clinical population by screening reference populations for early signs of memory loss or other difficulties associated with pre-Alzheimer's symptomotology, a family history of Alzheimer's Disease, genetic risk factors, age, sex, and other features found to predict high-risk for Alzheimer's Disease. Baseline scores on suitable metrics including the MMSE and the ADAS together with other metrics designed to evaluate a more normal population are collected. These patient populations are divided into suitable groups with placebo comparison against dosing alternatives with the agent. These patient populations are followed at intervals of about six months, and the endpoint for each patient is whether or not he or she converts to probable Alzheimer's Disease as defined by ADRDA criteria at the end of the observation.

Although the foregoing invention has been described in detail for purposes of clarity of understanding, it will be obvious that certain modifications may be practiced within the scope of the appended claims. All publications and patent documents cited herein, as well as text appearing in the figures and sequence listing, are hereby incorporated by reference in their entirety for all purposes to the same extent as if each were so individually denoted.

From the foregoing it will be apparent that the invention provides for a number of uses. For example, the invention provides for the use of any of the antibodies to Aβ described above in the treatment, prophylaxis or diagnosis of amyloidogenic disease, or in the manufacture of a medicament or diagnostic composition for use in the same.

We claim:

1. A purified humanized antibody which specifically binds beta amyloid peptide (Aβ), or antigen-binding fragment of said humanized antibody, the humanized antibody or antigen-binding fragment comprising a humanized light chain comprising three complementarity determining regions (CDR1, CDR2 and CDR3) from the monoclonal antibody 12A11 light chain variable region sequence set forth as SEQ ID NO:2, and wherein L2 is occupied by V, L4 is occupied by M, L36 is occupied by Y, L38 is occupied by Q, L40 is occupied by P, L44 is occupied by P, L46 is occupied by L, L47 is occupied by L, L48 is occupied by I, L49 is occupied by Y, L64 is occupied by G, L66 is occupied by G, L68 is occupied by G, L69 is occupied by T, L71 is occupied by F, L87 is occupied by Y, and L98 is occupied by F (Kabat numbering convention) and a humanized heavy chain comprising three complementarity determining regions (CDR1, CDR2 and CDR3) from the monoclonal antibody 12A11 heavy chain variable region sequence and wherein at least three variable region framework residues and amino acids occupying them are selected from the group consisting of H24 occupied by F, H28 occupied by S, H29 occupied by L, H37 occupied by I, H48 occupied by L, H67 occupied by L, H71 occupied by K, H73 occupied by T, and H78 occupied by V (Kabat numbering convention).

2. The humanized antibody of claim 1, wherein at least six heavy chain variable region framework residues and amino acids occupying them are selected from the group consisting of H24 occupied by F, H28 occupied by S, H29 occupied by L, H37 occupied by I, H48 occupied by L, H67 occupied by L, H71 occupied by K, H73 occupied by T, and H78 occupied by V.

3. The humanized antibody of claim 2, wherein H24 is occupied by F, H28 is occupied by S, H29 is occupied by L, H37 is occupied by I, H48 is occupied by L, H67 is occupied by L, H71 is occupied by K, H73 is occupied by T, and H78 is occupied by V.

4. The humanized antibody of claim 1, wherein the humanized light chain variable region has an amino acid sequence of SEQ ID NO:7.

5. The immunoglobulin or antigen binding fragment of any one of claims 1-4 which specifically binds to beta amyloid peptide (Aβ) with a binding affinity of at least $10^7$ M$^{-1}$.

6. The immunoglobulin or antigen binding fragment of any one of claims 1-4, wherein the heavy chain isotype is gamma 1.

7. The immunoglobulin or antigen binding fragment of any one of claims 1-4, which mediates phagocytosis of beta amyloid peptide (Aβ).

8. The immunoglobulin of any one of claims 1-4, which comprises an Fc region having altered binding to Fc receptors or complement proteins.

9. The antigen binding fragment of any one of claims 1-4, wherein said fragment is selected from the group consisting of Fab, Fab', F(ab')$_2$, Fabc, Fv, and single-chain antibody.

10. A purified immunoglobulin which specifically binds to beta amyloid peptide (Aβ), or antigen-binding fragment of said immunoglobulin, comprising a heavy chain variable region sequence as set forth in SEQ ID NO:10 and a light chain variable region sequence as set forth in SEQ ID NO:7, and constant regions from IgG1.

11. A purified immunoglobulin which specifically binds to beta amyloid peptide (Aβ), or antigen-binding fragment of said immunoglobulin, comprising a light chain variable region sequence set as forth in SEQ ID NO:7 and a heavy chain variable region sequence selected from the group consisting of: SEQ ID NO:10, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, and SEQ ID NO:31.

12. The immunoglobulin or antigen-binding fragment thereof of claim 11, wherein the heavy chain variable region sequence is as set forth in SEQ ID NO:13.

13. The immunoglobulin or antigen-binding fragment thereof of claim 11, wherein the heavy chain variable region sequence is as set forth in SEQ ID NO:14.

14. The immunoglobulin or antigen-binding fragment thereof of claim 11, wherein the heavy chain variable region sequence is as set forth in SEQ ID NO:15.

15. The immunoglobulin or antigen-binding fragment thereof of claim 11, wherein the heavy chain variable region sequence is as set forth in SEQ ID NO:16.

16. The immunoglobulin or antigen-binding fragment thereof of claim 11, wherein the heavy chain variable region sequence is as set forth in SEQ ID NO:17.

17. The immunoglobulin or antigen-binding fragment thereof of claim 11, wherein the heavy chain variable region sequence is as set forth in SEQ ID NO:18.

18. The immunoglobulin or antigen-binding fragment thereof of claim 11, wherein the heavy chain variable region sequence is as set forth in SEQ ID NO:19.

19. The immunoglobulin or antigen-binding fragment thereof of claim 11, wherein the heavy chain variable region sequence is as set forth in SEQ ID NO:20.

20. The immunoglobulin or antigen-binding fragment thereof of claim 11, wherein the heavy chain variable region sequence is as set forth in SEQ ID NO:21.

21. The immunoglobulin or antigen-binding fragment thereof of claim 11, wherein the heavy chain variable region sequence is as set forth in SEQ ID NO:22.

22. The immunoglobulin or antigen-binding fragment thereof of claim 11, wherein the heavy chain variable region sequence is as set forth in SEQ ID NO:23.

23. The immunoglobulin or antigen-binding fragment thereof of claim 11, wherein the heavy chain variable region sequence is as set forth in SEQ ID NO:24.

24. The immunoglobulin or antigen-binding fragment thereof of claim 11, wherein the heavy chain variable region sequence is as set forth in SEQ ID NO:25.

25. The immunoglobulin or antigen-binding fragment thereof of claim 11, wherein the heavy chain variable region sequence is as set forth in SEQ ID NO:26.

26. The immunoglobulin or antigen-binding fragment thereof of claim 11, wherein the heavy chain variable region sequence is as set forth in SEQ ID NO:27.

27. The immunoglobulin or antigen-binding fragment thereof of claim 11, wherein the heavy chain variable region sequence is as set forth in SEQ ID NO:28.

28. The immunoglobulin or antigen-binding fragment thereof of claim 11, wherein the heavy chain variable region sequence is as set forth in SEQ ID NO:29.

29. The immunoglobulin or antigen-binding fragment thereof of claim 11, wherein the heavy chain variable region sequence is as set forth in SEQ ID NO:30.

30. The immunoglobulin or antigen-binding fragment thereof of claim 11, wherein the heavy chain variable region sequence is as set forth in SEQ ID NO:31.

31. A purified immunoglobulin which specifically binds to beta amyloid peptide (Aβ), or antigen-binding fragment of said immunoglobulin, comprising a heavy chain variable region sequence as set forth in SEQ ID NO:10 and a light chain variable region sequence as set forth in SEQ ID NO:7.

32. A pharmaceutical composition comprising the immunoglobulin, or antigen binding fragment thereof of any one of claims 31-10 and 1-4 and a pharmaceutical carrier.

* * * * *

UNITED STATES PATENT AND TRADEMARK OFFICE
CERTIFICATE OF CORRECTION

| | | |
|---|---|---|
| PATENT NO. | : 7,871,615 B2 | Page 1 of 1 |
| APPLICATION NO. | : 10/858855 | |
| DATED | : January 18, 2011 | |
| INVENTOR(S) | : Basi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 18 days.

Signed and Sealed this
Twenty-sixth Day of July, 2011

David J. Kappos
*Director of the United States Patent and Trademark Office*

SEQUENCE LISTING

```
<160> NUMBER OF SEQ ID NOS: 35

<210> SEQ ID NO 1
<211> LENGTH: 393
<212> TYPE: DNA
<213> ORGANISM: Murine
<220> FEATURE:
<221> NAME/KEY: CDS
<222> LOCATION: (1)...(393)
<220> FEATURE:
<221> NAME/KEY: sig_peptide
<222> LOCATION: (1)...(57)

<400> SEQUENCE: 1 atg aag ttg cct gtt agg ctg ttg gtg ctg atg ttc tgg att cct gct        48
Met Lys Leu Pro Val Arg Leu Leu Val Leu Met Phe Trp Ile Pro Ala
            -15                 -10                 -5 tcc agc agt gat gtt ttg atg acc caa act cca ctc tcc ctg cct gtc        96
Ser Ser Ser Asp Val Leu Met Thr Gln Thr Pro Leu Ser Leu Pro Val
             1                  5                  10 agt ctt gga gat caa gcc tcc atc tct tgc aga tct agt cag agc att       144
Ser Leu Gly Asp Gln Ala Ser Ile Ser Cys Arg Ser Ser Gln Ser Ile
        15                  20                  25 gta cat agt aat gga aac acc tac tta gaa tgg tac ctg cag aaa cca       192
Val His Ser Asn Gly Asn Thr Tyr Leu Glu Trp Tyr Leu Gln Lys Pro
 30                  35                  40                  45 ggc cag tct cca aag ctc ctg atc tac aaa gtt tcc aac cga ttt tct       240
Gly Gln Ser Pro Lys Leu Leu Ile Tyr Lys Val Ser Asn Arg Phe Ser
                 50                  55                  60 ggg gtc cca gac agg ttc agt ggc agt gga tca ggg aca gat ttc aca       288
Gly Val Pro Asp Arg Phe Ser Gly Ser Gly Ser Gly Thr Asp Phe Thr
             65                  70                  75 ctc aag atc agc aga gtg gag gct gag gat ctg gga att tat tac tgc       336
Leu Lys Ile Ser Arg Val Glu Ala Glu Asp Leu Gly Ile Tyr Tyr Cys
         80                  85                  90 ttt caa agt tca cat gtt cct ctc acg ttc ggt gct ggg acc aag ctg       384
Phe Gln Ser Ser His Val Pro Leu Thr Phe Gly Ala Gly Thr Lys Leu
     95                 100                 105 gag ctg aaa                                                            393
Glu Leu Lys
110

<210> SEQ ID NO 2
<211> LENGTH: 131
<212> TYPE: PRT
<213> ORGANISM: Murine
<220> FEATURE:
<221> NAME/KEY: SIGNAL
<222> LOCATION: (1)...(19)

<400> SEQUENCE: 2

Met Lys Leu Pro Val Arg Leu Leu Val Leu Met Phe Trp Ile Pro Ala
            -15                 -10                 -5

Ser Ser Ser Asp Val Leu Met Thr Gln Thr Pro Leu Ser Leu Pro Val
             1                  5                  10

Ser Leu Gly Asp Gln Ala Ser Ile Ser Cys Arg Ser Ser Gln Ser Ile
        15                  20                  25
```

```
Val His Ser Asn Gly Asn Thr Tyr Leu Glu Trp Tyr Leu Gln Lys Pro
 30                  35                  40                  45

Gly Gln Ser Pro Lys Leu Leu Ile Tyr Lys Val Ser Asn Arg Phe Ser
             50                  55                  60

Gly Val Pro Asp Arg Phe Ser Gly Ser Gly Ser Gly Thr Asp Phe Thr
         65                  70                  75

Leu Lys Ile Ser Arg Val Glu Ala Glu Asp Leu Gly Ile Tyr Tyr Cys
     80                  85                  90

Phe Gln Ser Ser His Val Pro Leu Thr Phe Gly Ala Gly Thr Lys Leu
     95                 100                 105

Glu Leu Lys
110

<210> SEQ ID NO 3
<211> LENGTH: 417
<212> TYPE: DNA
<213> ORGANISM: Murine
<220> FEATURE:
<221> NAME/KEY: CDS
<222> LOCATION: (1)...(417)
<220> FEATURE:
<221> NAME/KEY: sig_peptide
<222> LOCATION: (1)...(57)

<400> SEQUENCE: 3 atg gac agg ctt act act tca ttc ctg ctg ctg att gtc cct gca tat      48
Met Asp Arg Leu Thr Thr Ser Phe Leu Leu Leu Ile Val Pro Ala Tyr
                -15                 -10                  -5 gtc ttg tcc caa gtt act cta aaa gag tct ggc cct ggg ata ttg aag      96
Val Leu Ser Gln Val Thr Leu Lys Glu Ser Gly Pro Gly Ile Leu Lys
             1               5                  10 ccc tca cag acc ctc agt ctg act tgt tct ttc tct ggg ttt tca ctg     144
Pro Ser Gln Thr Leu Ser Leu Thr Cys Ser Phe Ser Gly Phe Ser Leu
     15                  20                  25 agc act tct ggt atg agt gta ggc tgg att cgt cag cct tca ggg aag     192
Ser Thr Ser Gly Met Ser Val Gly Trp Ile Arg Gln Pro Ser Gly Lys
 30                  35                  40                  45 ggt ctg gag tgg ctg gca cac att tgg tgg gat gat gat aag tac tat     240
Gly Leu Glu Trp Leu Ala His Ile Trp Trp Asp Asp Asp Lys Tyr Tyr
             50                  55                  60 aac cca tcc ctg aag agc cgg ctc aca atc tcc aag gat acc tcc aga     288
Asn Pro Ser Leu Lys Ser Arg Leu Thr Ile Ser Lys Asp Thr Ser Arg
         65                  70                  75 aac cag gta ttc ctc aag atc acc agt gtg gac act gca gat act gcc     336
Asn Gln Val Phe Leu Lys Ile Thr Ser Val Asp Thr Ala Asp Thr Ala
     80                  85                  90 act tac tac tgt gct cga aga act act acg gct gac tac ttt gcc tac     384
Thr Tyr Tyr Cys Ala Arg Arg Thr Thr Thr Ala Asp Tyr Phe Ala Tyr
 95                 100                 105 tgg ggc caa ggc acc act ctc aca gtc tcc tca                         417
Trp Gly Gln Gly Thr Thr Leu Thr Val Ser Ser
110                 115                 120

<210> SEQ ID NO 4
<211> LENGTH: 139
<212> TYPE: PRT
<213> ORGANISM: Murine
<220> FEATURE:
<221> NAME/KEY: SIGNAL
<222> LOCATION: (1)...(19)

<400> SEQUENCE: 4
```

```
Met Asp Arg Leu Thr Thr Ser Phe Leu Leu Leu Ile Val Pro Ala Tyr
            -15                 -10                 -5
Val Leu Ser Gln Val Thr Leu Lys Glu Ser Gly Pro Gly Ile Leu Lys
             1               5                  10
Pro Ser Gln Thr Leu Ser Leu Thr Cys Ser Phe Ser Gly Phe Ser Leu
         15              20                  25
Ser Thr Ser Gly Met Ser Val Gly Trp Ile Arg Gln Pro Ser Gly Lys
 30              35                  40                  45
Gly Leu Glu Trp Leu Ala His Ile Trp Trp Asp Asp Lys Tyr Tyr
             50                  55                  60
Asn Pro Ser Leu Lys Ser Arg Leu Thr Ile Ser Lys Asp Thr Ser Arg
             65                  70                  75
Asn Gln Val Phe Leu Lys Ile Thr Ser Val Asp Thr Ala Asp Thr Ala
             80                  85                  90
Thr Tyr Tyr Cys Ala Arg Arg Thr Thr Thr Ala Asp Tyr Phe Ala Tyr
             95                 100                 105
Trp Gly Gln Gly Thr Thr Leu Thr Val Ser Ser
110                 115                 120
```

```
<210> SEQ ID NO 5
<211> LENGTH: 429
<212> TYPE: DNA
<213> ORGANISM: Artificial Sequence
<220> FEATURE:
<223> OTHER INFORMATION: synthetic

<400> SEQUENCE: 5
cmgmaagctt gccgccacca tgaagttgcc tgttaggctg ttggtgctga tgttctggat     60
tcctgcttcc agcagtgatg tttttgatga ccaaactcca ctctccctgc ctgtcagtct    120
tggagatcaa gcctccatct cttgcagatc tagtcagagc attgtacata gtaatggaaa    180
cacctactta gaatggtacc tgcagaaacc aggccagtct ccaaagctcc tgatctacaa    240
agtttccaac cgattttctg ggtcccaga caggttcagt ggcagtggat cagggacaga    300
tttcacactc aagatcagca gagtggaggc tgaggatctg gaatttatt actgctttca    360
aagttcacat gttcctctca cgttcggtgc tgggaccaag ctggagctga acgtgagtg    420
gatcctmgr                                                            429
```

```
<210> SEQ ID NO 6
<211> LENGTH: 445
<212> TYPE: DNA
<213> ORGANISM: Artificial Sequence
<220> FEATURE:
<223> OTHER INFORMATION: synthetic

<400> SEQUENCE: 6
aagcttgccg ccaccatgga caggcttact acttcattcc tgctgctgat tgtccctgca     60
tatgtcttgt cccaagttac tctaaaagag tctggccctg gatattgaa gccctcacag    120
accctcagtc tgacttgttc tttctctggg ttttcactga gcacttctgg tatgagtgta    180
ggctggattc gtcagccttc agggaagggt ctggagtggc tggcacacat tggtgggat    240
gatgataagt actataaccc atccctgaag agccggctca aatctccaa ggatacctcc    300
agaaaccagg tattcctcaa gatcaccagt gtggacactg cagatactgc cacttactac    360
tgtgctcgaa gaactactac ggctgactac tttgcctact ggggccaagg caccactctc    420
acagtctcct caggtgagtg gatcc                                          445
```

```
<210> SEQ ID NO 7
<211> LENGTH: 112
<212> TYPE: PRT
<213> ORGANISM: Artificial Sequence
<220> FEATURE:
<223> OTHER INFORMATION: synthetic h12A11v1 - VL region

<400> SEQUENCE: 7
```

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ser
                85                  90                  95

Ser His Val Pro Leu Thr Phe Gly Gln Gly Thr Lys Leu Glu Ile Lys
            100                 105                 110

```
<210> SEQ ID NO 8
<211> LENGTH: 134
<212> TYPE: PRT
<213> ORGANISM: Homo sapiens
<220> FEATURE:
<221> NAME/KEY: SIGNAL
<222> LOCATION: (1)...(22)

<400> SEQUENCE: 8
```

Met Lys Tyr Leu Leu Pro Thr Ala Ala Ala Gly Leu Leu Leu Leu Ala
            -20                 -15                 -10

Ala Gln Pro Ala Met Ala Asp Val Val Met Thr Gln Ser Pro Leu Ser
     -5                   1               5                  10

Leu Pro Val Thr Pro Gly Glu Pro Ala Ser Ile Ser Cys Arg Ser Ser
                15                  20                  25

Gln Ser Leu Leu His Ser Asn Gly Tyr Asn Tyr Leu Asp Trp Tyr Leu
            30                  35                  40

Gln Lys Pro Gly Gln Ser Pro Gln Leu Leu Ile Tyr Leu Gly Ser Asn
        45                  50                  55

Arg Ala Ser Gly Val Pro Asp Arg Phe Ser Gly Ser Gly Ser Gly Thr
    60                  65                  70

Asp Phe Thr Leu Lys Ile Ser Arg Val Glu Ala Glu Asp Val Gly Val
 75                  80                  85                  90

Tyr Tyr Cys Met Gln Ala Leu Gln Thr Pro Tyr Thr Phe Gly Gln Gly
                95                  100                 105

Thr Lys Leu Glu Ile Lys
            110

```
<210> SEQ ID NO 9
<211> LENGTH: 120
<212> TYPE: PRT
<213> ORGANISM: Homo sapiens
<220> FEATURE:
<221> NAME/KEY: SIGNAL
<222> LOCATION: (1)...(20)

<400> SEQUENCE: 9
```

```
Met Arg Leu Pro Ala Gln Leu Leu Gly Leu Leu Met Leu Trp Val Ser
-20                 -15                 -10                  -5

Gly Ser Ser Gly Asp Ile Val Met Thr Gln Ser Pro Leu Ser Leu Pro
              1                   5                  10

Val Thr Pro Gly Glu Pro Ala Ser Ile Ser Cys Arg Ser Ser Gln Ser
         15                  20                  25

Leu Leu His Ser Asn Gly Tyr Asn Tyr Leu Asp Trp Tyr Leu Gln Lys
     30                  35                  40

Pro Gly Gln Ser Pro Gln Leu Leu Ile Tyr Leu Gly Ser Asn Arg Ala
 45                  50                  55                  60

Ser Gly Val Pro Asp Arg Phe Ser Gly Ser Gly Ser Gly Thr Asp Phe
                 65                  70                  75

Thr Leu Lys Ile Ser Arg Val Glu Ala Glu Asp Val Gly Val Tyr Tyr
             80                  85                  90

Cys Met Gln Ala Leu Gln Thr Pro
         95                 100
```

<210> SEQ ID NO 10
<211> LENGTH: 120
<212> TYPE: PRT
<213> ORGANISM: Artificial Sequence
<220> FEATURE:
<223> OTHER INFORMATION: h12A11v1 - VH region

<400> SEQUENCE: 10

```
Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Ser Leu Ser Thr Ser
             20                  25                  30

Gly Met Ser Val Gly Trp Ile Arg Gln Ala Pro Gly Lys Gly Leu Glu
         35                  40                  45

Trp Leu Ala His Ile Trp Trp Asp Asp Lys Tyr Tyr Asn Pro Ser
 50                  55                  60

Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
             85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120
```

<210> SEQ ID NO 11
<211> LENGTH: 141
<212> TYPE: PRT
<213> ORGANISM: Homo sapiens
<220> FEATURE:
<221> NAME/KEY: SIGNAL
<222> LOCATION: (1)...(19)

<400> SEQUENCE: 11

```
Met Glu Phe Gly Leu Ser Trp Val Phe Leu Val Ala Leu Leu Arg Gly
                 -15                 -10                  -5

Val Gln Cys Gln Val Gln Leu Val Glu Ser Gly Gly Gly Val Val Gln
              1                   5                  10

Pro Gly Arg Ser Leu Arg Leu Ser Cys Ala Ala Ser Gly Phe Thr Phe
         15                  20                  25
```

```
Ser Ser Tyr Ala Met His Trp Val Arg Gln Ala Pro Gly Lys Gly Leu
 30              35                  40                  45

Glu Trp Val Ala Val Ile Ser Tyr Asp Gly Ser Asn Lys Tyr Tyr Ala
                 50                  55                  60

Asp Ser Val Lys Gly Arg Phe Thr Ile Ser Arg Asp Asn Ser Lys Asn
             65                  70                  75

Thr Leu Tyr Leu Gln Met Asn Ser Leu Arg Ala Glu Asp Thr Ala Val
         80                  85                  90

Tyr Tyr Cys Ala Arg Asp Arg His Ser Ser Trp Tyr Tyr Gly Met
     95                 100                 105

Asp Val Trp Gly Gln Gly Thr Thr Val Thr Val Ser Ser
110                 115                 120

<210> SEQ ID NO 12
<211> LENGTH: 137
<212> TYPE: PRT
<213> ORGANISM: Homo sapiens
<220> FEATURE:
<221> NAME/KEY: SIGNAL
<222> LOCATION: (1)...(19)

<400> SEQUENCE: 12

Met Glu Phe Gly Leu Ser Trp Val Phe Leu Val Ala Leu Leu Arg Gly
                -15                 -10                  -5

Val Gln Cys Gln Val Gln Leu Val Glu Ser Gly Gly Gly Val Val Gln
             1                   5                  10

Pro Gly Arg Ser Leu Arg Leu Ser Cys Ala Ala Ser Gly Phe Thr Phe
         15                  20                  25

Ser Ser Tyr Ala Met His Trp Val Arg Gln Ala Pro Gly Lys Gly Leu
 30              35                  40                  45

Glu Trp Val Ala Val Ile Ser Tyr Asp Gly Ser Asn Lys Tyr Tyr Ala
                 50                  55                  60

Asp Ser Val Lys Gly Arg Phe Thr Ile Ser Arg Asp Asn Ser Lys Asn
             65                  70                  75

Thr Leu Tyr Leu Gln Met Asn Ser Leu Arg Ala Glu Asp Thr Ala Val
         80                  85                  90

Tyr Tyr Cys Ala Arg Asp Ala Lys Leu Leu Met Leu Leu Ile Ser Gly
     95                 100                 105

Ala Lys Gly Gln Trp Ser Pro Ser Leu
110                 115

<210> SEQ ID NO 13
<211> LENGTH: 120
<212> TYPE: PRT
<213> ORGANISM: Artificial Sequence
<220> FEATURE:
<223> OTHER INFORMATION: synthetic h12A11v2

<400> SEQUENCE: 13

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
             20                  25                  30

Gly Met Ser Val Gly Trp Ile Arg Gln Ala Pro Gly Lys Gly Leu Glu
         35                  40                  45

Trp Val Ala His Ile Trp Trp Asp Asp Asp Lys Tyr Tyr Asn Pro Ser
     50                  55                  60

Leu Lys Ser Arg Phe Thr Ile Ser Lys Asp Thr Ser Lys Asn Thr Leu
```

```
                65                  70                  75                  80
Tyr Leu Gln Met Asn Ser Leu Arg Ala Glu Asp Thr Ala Val Tyr Tyr
                    85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 14
<211> LENGTH: 120
<212> TYPE: PRT
<213> ORGANISM: Artificial Sequence
<220> FEATURE:
<223> OTHER INFORMATION: synthetic h12A11v2.1

<400> SEQUENCE: 14

Gln Val Gln Leu Val Glu Ser Gly Gly Gly Val Val Gln Pro Gly Arg
  1               5                  10                  15

Ser Leu Arg Leu Ser Cys Ala Phe Ser Gly Phe Thr Leu Ser Thr Ser
                 20                  25                  30

Gly Met Ser Val Gly Trp Ile Arg Gln Ala Pro Gly Lys Gly Leu Glu
             35                  40                  45

Trp Val Ala His Ile Trp Trp Asp Asp Lys Tyr Tyr Asn Pro Ser
         50                  55                  60

Leu Lys Ser Arg Phe Thr Ile Ser Lys Asp Asn Ser Lys Asn Thr Leu
 65                  70                  75                  80

Tyr Leu Gln Met Asn Ser Leu Arg Ala Glu Asp Thr Ala Val Tyr Tyr
                    85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 15
<211> LENGTH: 120
<212> TYPE: PRT
<213> ORGANISM: Artificial Sequence
<220> FEATURE:
<223> OTHER INFORMATION: synthetic h12A11v3

<400> SEQUENCE: 15

Gln Val Gln Leu Val Glu Ser Gly Gly Gly Val Val Gln Pro Gly Arg
  1               5                  10                  15

Ser Leu Arg Leu Ser Cys Ala Phe Ser Gly Phe Thr Leu Ser Thr Ser
                 20                  25                  30

Gly Met Ser Val Gly Trp Ile Arg Gln Ala Pro Gly Lys Gly Leu Glu
             35                  40                  45

Trp Val Ala His Ile Trp Trp Asp Asp Lys Tyr Tyr Asn Pro Ser
         50                  55                  60

Leu Lys Ser Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                    85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120
```

```
<210> SEQ ID NO 16
<211> LENGTH: 120
<212> TYPE: PRT
<213> ORGANISM: Artificial Sequence
<220> FEATURE:
<223> OTHER INFORMATION: synthetic h12A11v4.1

<400> SEQUENCE: 16

Gln Val Gln Leu Val Glu Ser Gly Gly Gly Val Val Gln Pro Gly Arg
  1               5                  10                  15

Ser Leu Arg Leu Ser Cys Ala Phe Ser Gly Phe Thr Leu Ser Thr Ser
             20                  25                  30

Gly Met Ser Val Gly Trp Ile Arg Gln Ala Pro Gly Lys Gly Leu Glu
         35                  40                  45

Trp Leu Ala His Ile Trp Trp Asp Asp Lys Tyr Tyr Asn Pro Ser
     50                  55                  60

Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 17
<211> LENGTH: 120
<212> TYPE: PRT
<213> ORGANISM: Artificial Sequence
<220> FEATURE:
<223> OTHER INFORMATION: synthetic h12A11v4.2

<400> SEQUENCE: 17

Gln Val Gln Leu Val Glu Ser Gly Gly Gly Val Val Gln Pro Gly Arg
  1               5                  10                  15

Ser Leu Arg Leu Ser Cys Ala Phe Ser Gly Phe Ser Leu Ser Thr Ser
             20                  25                  30

Gly Met Ser Val Gly Trp Ile Arg Gln Ala Pro Gly Lys Gly Leu Glu
         35                  40                  45

Trp Val Ala His Ile Trp Trp Asp Asp Lys Tyr Tyr Asn Pro Ser
     50                  55                  60

Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: synthetic h12A11v4.3

<400> SEQUENCE: 18

Gln Val Gln Leu Val Glu Ser Gly Gly Gly Val Val Gln Pro Gly Arg
```

-continued

```
                1               5                   10                  15
Ser Leu Arg Leu Ser Cys Ala Phe Ser Gly Phe Ser Leu Ser Thr Ser
                    20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                    100                 105                 110

Gly Thr Thr Val Thr Val Ser Ser
            115                 120
```

<210> SEQ ID NO 19
<211> LENGTH: 120
<212> TYPE: PRT
<213> ORGANISM: Artificial Sequence
<220> FEATURE:
<223> OTHER INFORMATION: synthetic h12A11v4.4

<400> SEQUENCE: 19

```
Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
                    20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
                    100                 105                 110

Gly Thr Thr Val Thr Val Ser Ser
            115                 120
```

<210> SEQ ID NO 20
<211> LENGTH: 120
<212> TYPE: PRT
<213> ORGANISM: Artificial Sequence
<220> FEATURE:
<223> OTHER INFORMATION: synthetic h12A11v5.1

<400> SEQUENCE: 20

```
Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                    20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
    50                  55                  60
```

```
Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 21
<211> LENGTH: 120
<212> TYPE: PRT
<213> ORGANISM: Artificial Sequence
<220> FEATURE:
<223> OTHER INFORMATION: synthetic h12A11v5.2

<400> SEQUENCE: 21

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
                 20                  25                  30

Gly Met Ser Val Gly Trp Ile Arg Gln Ala Pro Gly Lys Gly Leu Glu
             35                  40                  45

Trp Leu Ala His Ile Trp Trp Asp Asp Lys Tyr Tyr Asn Pro Ser
 50                  55                  60

Leu Lys Ser Arg Phe Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 22
<211> LENGTH: 121
<212> TYPE: PRT
<213> ORGANISM: Artificial Sequence
<220> FEATURE:
<223> OTHER INFORMATION: synthetic h12A11v5.3

<400> SEQUENCE: 22

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
                 20                  25                  30

Gly Met Ser Val Gly Trp Ile Arg Gln Ala Pro Gly Lys Gly Leu Glu
             35                  40                  45

Trp Leu Ala His Ile Trp Trp Asp Asp Lys Tyr Tyr Asn Pro Ser
 50                  55                  60

Leu Lys Ser Arg Leu Thr Ile Ser Lys Asp Thr Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser Val
        115                 120
```

<210> SEQ ID NO 23
<211> LENGTH: 121
<212> TYPE: PRT
<213> ORGANISM: Artificial Sequence
<220> FEATURE:
<223> OTHER INFORMATION: synthetic h12A11v5.4

<400> SEQUENCE: 23

```
Gln Val Gln Leu Val Glu Ser Gly Gly Gly Val Val Gln Pro Gly Arg
  1               5                  10                  15

Ser Leu Arg Leu Ser Cys Ala Phe Ser Gly Phe Ser Leu Ser Thr Ser
             20                  25                  30

Gly Met Ser Val Gly Trp Ile Arg Gln Ala Pro Gly Lys Gly Leu Glu
         35                  40                  45

Trp Val Ala His Ile Trp Trp Asp Asp Lys Tyr Tyr Asn Pro Ser
 50                  55                  60

Leu Lys Ser Arg Phe Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser Val
            115                 120
```

<210> SEQ ID NO 24
<211> LENGTH: 120
<212> TYPE: PRT
<213> ORGANISM: Artificial Sequence
<220> FEATURE:
<223> OTHER INFORMATION: synthetic h12A11v5.5

<400> SEQUENCE: 24

```
Gln Val Gln Leu Val Glu Ser Gly Gly Gly Val Val Gln Pro Gly Arg
  1               5                  10                  15

Ser Leu Arg Leu Ser Cys Ala Phe Ser Gly Phe Ser Leu Ser Thr Ser
             20                  25                  30

Gly Met Ser Val Gly Trp Ile Arg Gln Ala Pro Gly Lys Gly Leu Glu
         35                  40                  45

Trp Val Ala His Ile Trp Trp Asp Asp Lys Tyr Tyr Asn Pro Ser
 50                  55                  60

Leu Lys Ser Arg Leu Thr Ile Ser Lys Asp Thr Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120
```

<210> SEQ ID NO 25
<211> LENGTH: 120
<212> TYPE: PRT
<213> ORGANISM: Artificial Sequence
<220> FEATURE:
<223> OTHER INFORMATION: synthetic h12A11v5.6

<400> SEQUENCE: 25

```
Gln Val Gln Leu Val Glu Ser Gly Gly Gly Val Val Gln Pro Gly Arg
 1               5                   10                  15

Ser Leu Arg Leu Ser Cys Ala Phe Ser Gly Phe Ser Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120
```

<210> SEQ ID NO 26
<211> LENGTH: 120
<212> TYPE: PRT
<213> ORGANISM: Artificial Sequence
<220> FEATURE:
<223> OTHER INFORMATION: synthetic h12A11 6.1

<400> SEQUENCE: 26

```
Gln Val Gln Leu Val Glu Ser Gly Gly Gly Val Val Gln Pro Gly Arg
 1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120
```

<210> SEQ ID NO 27
<211> LENGTH: 120
<212> TYPE: PRT
<213> ORGANISM: Artificial Sequence
<220> FEATURE:
<223> OTHER INFORMATION: synthetic h12A11v6.2

<400> SEQUENCE: 27

```
Gln Val Gln Leu Val Glu Ser Gly Gly Gly Val Val Gln Pro Gly Arg
 1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Asp Lys Tyr Tyr Asn Pro Ser
    50                  55                  60
```

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 28
<211> LENGTH: 120
<212> TYPE: PRT
<213> ORGANISM: Artificial Sequence
<220> FEATURE:
<223> OTHER INFORMATION: synthetic h12A11v6.3

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 29
<211> LENGTH: 120
<212> TYPE: PRT
<213> ORGANISM: Artificial Sequence
<220> FEATURE:
<223> OTHER INFORMATION: synthetic h12A11v6.4

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser

<210> SEQ ID NO 30
<211> LENGTH: 120
<212> TYPE: PRT
<213> ORGANISM: Artificial Sequence
<220> FEATURE:
<223> OTHER INFORMATION: synthetic h12A11v7

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Val Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 31
<211> LENGTH: 120
<212> TYPE: PRT
<213> ORGANISM: Artificial Sequence
<220> FEATURE:
<223> OTHER INFORMATION: synthetic h12A11v8

<400> SEQUENCE: 31

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 32
<211> LENGTH: 5
<212> TYPE: PRT
<213> ORGANISM: Artificial Sequence
<220> FEATURE:
<223> OTHER INFORMATION: synthetic igg hinge region -continued

```
<400> SEQUENCE: 32

Leu Leu Gly Gly Pro
1               5

<210> SEQ ID NO 33
<211> LENGTH: 5
<212> TYPE: PRT
<213> ORGANISM: Artificial Sequence
<220> FEATURE:
<223> OTHER INFORMATION: synthetic igg hinge region

<400> SEQUENCE: 33

Leu Glu Gly Gly Pro
1               5

<210> SEQ ID NO 34
<211> LENGTH: 396
<212> TYPE: DNA
<213> ORGANISM: Artificial Sequence
<220> FEATURE:
<223> OTHER INFORMATION: humanized 12A11 v1 VL sequence
<220> FEATURE:
<221> NAME/KEY: sig_peptide
<222> LOCATION: (1)...(60)

<400> SEQUENCE: 34
atgaggctcc ctgctcagct cctggggctg ctgatgctct gggtctctgg ctccagtggg     60
gatgttgtga tgacccaatc tccactctcc ctgcctgtca ctcctggaga gccagcctcc    120
atctcttgca gatctagtca gagcattgtg catagtaatg aaacaccta cctggaatgg     180 tacctgcaga aaccaggcca gtctccacag ctcctgatct acaaagtttc caaccgattt    240
tctggggtcc cagacaggtt cagtggcagt ggatcaggga cagatttcac actcaagatc    300
agcagagtgg aggctgagga tgtgggagtt tattactgct ttcaaagttc acatgttcct    360
ctcaccttcg gtcaggggac caagctggag atcaaa                              396

<210> SEQ ID NO 35
<211> LENGTH: 417
<212> TYPE: DNA
<213> ORGANISM: Artificial Sequence
<220> FEATURE:
<223> OTHER INFORMATION: humanized 12A11 v1 NH sequence
<220> FEATURE:
<221> NAME/KEY: sig_peptide
<222> LOCATION: (1)...(57)

<400> SEQUENCE: 35
atggagtttg ggctgagctg ggttttcctc gttgctcttc tgagaggtgt ccagtgtcaa     60
gttcagctgg tggagtctgg cggcggggtg gtgcagcccg gacggtccct caggctgtct    120
tgtgctttct ctgggttttc actgagcact tctggtatga gtgtgggctg gattcgtcag    180
gctccaggga agggtctgga gtggctggca cacatttggt gggatgatga taagtactat    240
aacccatccc tgaagagccg gctcacaatc tccaaggata cctccaaaaa caccgtgtac    300
ctccagatga acagtctgcg ggctgaagat actgccgtgt actactgtgc tcgaagaact    360
actaccgctg actactttgc ctactggggc caaggcacca ctgtcacagt ctcctca       417
```